United States Patent
Segelstein et al.

(10) Patent No.: US 7,241,798 B2
(45) Date of Patent: Jul. 10, 2007

(54) NK1 ANTAGONISTS

(75) Inventors: Barbara E. Segelstein, Gales Ferry, CT (US); Travis T. Wager, New London, CT (US); Willard M. Welch, Mystic, CT (US)

(73) Assignee: Pfizer Inc., New York, NY (US)

( * ) Notice: Subject to any disclaimer, the term of this patent is extended or adjusted under 35 U.S.C. 154(b) by 85 days.

(21) Appl. No.: 11/147,602

(22) Filed: Jun. 7, 2005

(65) Prior Publication Data

US 2005/0272800 A1 Dec. 8, 2005

Related U.S. Application Data

(60) Provisional application No. 60/577,972, filed on Jun. 8, 2004.

(51) Int. Cl.
*C07D 209/52* (2006.01)
*A61K 31/403* (2006.01)

(52) U.S. Cl. ...................... 514/412; 548/452

(58) Field of Classification Search ............... 548/452; 546/158; 514/412
See application file for complete search history.

(56) References Cited

U.S. PATENT DOCUMENTS 6,329,394 B1  12/2001  Hagan et al.

FOREIGN PATENT DOCUMENTS

EP   0528495   2/1993
EP   1120723   8/2001

OTHER PUBLICATIONS

Michels et al. Chemische Berichte. 1988, 121(10), 1775-83. * Indicates that the CAS Abstract and structure are attached.*
Kris, M. G. Journal of Clinical Oncology, vol. 21 (22), 2003, 4077-4080.*
Ramadan et al. Current Medical Research and Opinion, 17(1s), 2001, s71-s80. * Indicates only one chapter of article is provided.*
Tverezovsky V.V. et al., "Synthesis of (2S,3R,4S)-3,4-Methanoproline and Analogues by Cyclopropylidnene Insertion", *Tetrahedron*, Elsevier Science Publishers, Amsterdam NL, vol. 53, No. 43 Oct. 27, 1997 pp. 14773-14792.
Bonnaud, Bernard et al., "Stereoselective synthesis of cis and trans 2-substituted 1-phenyl-3-azabicyclo '3.10!hexanes", *Journal of Heterocyclic Chem.*, vol. 30, No. 2, p. 505.
Search Report, PCT/IB2005/001757, May 26, 2005.

* cited by examiner

*Primary Examiner*—Joseph K. McKane
*Assistant Examiner*—Jason M. Nolan
(74) *Attorney, Agent, or Firm*—Steve Zelzon; Jolene W. Appleman

(57) ABSTRACT

The invention is to compounds exhibiting neurokinin inhibitory properties, pharmaceutical compositions comprising same and methods of treatment for neurokinin-mediated conditions.

11 Claims, No Drawings

NK1 ANTAGONISTS

The entire disclosure of parent application 60/577,972 filed Jun. 8, 2004 is fully incorporated herein by reference thereto.

FIELD OF THE INVENTION

The invention pertains to compounds which are antagonists to tachykinins, including substance P and other neurokinins (NK); to pharmaceutical compositions comprising the same; and methods of treating neurokinin-mediated diseases, among others.

BACKGROUND OF THE INVENTION

The mammalian peptide Neurokinin B (NKB) belongs to the Tachykinin (TK) peptide family which also includes Substance P (SP) and Neurokinin A (NKA). Pharmacological and molecular biological evidence has shown the existence of three subtypes of TK receptor (NK-1, NK-2 and NK-3). Substance P (also known as NK-1) is a naturally occurring undecapeptide so named due to its prompt stimulatory action on smooth muscle tissue. More specifically, substance P is a pharmacologically active neuropeptide produced in mammals and possessing a characteristic amino acid sequence as illustrated in U.S. Pat. No. 4,680,283. NK-1 antanosists have been previously reported in EP528495A1.

SUMMARY OF THE INVENTION

In one practice, the invention relates to a compound having Formula I:

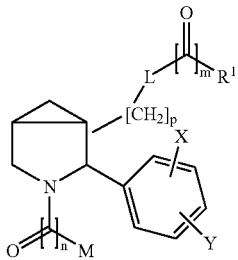

or pharmaceutically acceptable salts or solvates thereof, wherein:

m is 0 or 1;
n is 0 or 1;
p is 0 or 1;
L is —O—, —C(=O)N($R^5$)— or —N($R^5$)—;
M is $R^2$, —$NR^2R^3$, or —$NR^2R^4$;
$R^1$ and $R^2$ are each independently H, —($C_1$-$C_6$)alkyl, —($C_1$-$C_6$)aryl,
—($C_1$-$C_6$)heterocycloalkyl, —$NR^1$—($C_1$-$C_6$)aryl or —($C_1$-$C_6$)heteroaryl, wherein each of said
—($C_1$-$C_6$)alkyl, —($C_1$-$C_6$)aryl, —($C_1$-$C_6$)heterocycloalkyl, —$NR^1$—($C_1$-$C_6$)aryl or —($C_1$-$C_6$)heteroaryl is optionally substituted with 1-3 moieties independently selected from X', Y' or Z';
$R^3$, $R^4$ and $R^5$ are each independently selected from H, $CH_3$, or —($C_1$-$C_6$)alkyl; and X, Y, X', Y' and Z' are each independently selected from H, $CH_3$, —($C_1$-$C_6$)alkyl, $CF_3$, OH, $OCH_3$, —O—($C_1$-$C_6$) alkyl, halogen, and CN.

Another practice of the invention relates to a pharmaceutical composition for antagonizing the effect of NK-1 at their receptor sites in a mammal comprising an NK-1 receptor antagonizing amount of a compound of Formula I, or a pharmaceutically acceptable salt or solvate thereof, and a pharmaceutically acceptable carrier.

Another practice of the invention relates to a pharmaceutical composition for treating a condition or disorder associated with the activity, preferably the overactivity, of NK-1 receptors in a mammal, comprising an amount of a compound of Formula I, or a pharmaceutically acceptable salt or solvate thereof, and a pharmaceutically acceptable carrier, wherein the amount of said compound of Formula I is effective in (1) antagonizing the NK-1 receptor, and/or (2) treating said condition or disorder. The "activity" of NK-1 receptors refers to overactivity, underactivity or normal activity of these receptors.

Another practice of the invention relates to a pharmaceutical composition for treating in a mammal a condition or disorder selected from the group consisting of sleep disorders, autism, pervasive development disorder, rheumatoid arthritis, osteoarthritis, fibromyalgia, human immunodeficiency virus (HIV) infections, emesis, major depressive disorders, dissociative disorders, anorexia, bulimia, ulcerative colitis, Crohn's disease, irritable bowel syndrome, functional abdominal pain, chronic fatigue syndrome, sudden infant death syndrome (SIDS), overactive bladder, chronic cystitis, chemotherapy induced cystitis, cough, angiotensin converting enzyme (ACE) induced cough, itch, hiccups, premenstrual syndrome, premenstrual dysphoric disorder, schizophrenia, schizoaffective disorder, delusional disorder, substance-induced psychotic disorder, brief psychotic disorder, shared psychotic disorder, psychotic disorder due to a general medical condition, schizophreniform disorder, amenorrheic disorders such as desmenorrhea, obesity, epilepsy, primary movement disorders, spasticities, Scott's syndrome, Tourette's syndrome, palsys, amyolateral sclerosis (ALS), akinetic-rigid disorders, akinesias, dyskinesias, restless leg syndrome, movement disorders associated with Parkinson's disease or Huntington's disease, mastalgia syndromes, motion sickness, immune dysfunctions, generalized anxiety disorder, panic disorder, social phobia, agoraphobia, specific phobias, obsessive-compulsive disorder, post-traumatic stress disorder, major depression, single episode depression, recurrent depression, child abuse induced depression, postpartum depression, dysthemia, cyclothymia, bipolar disorder, neurocardiac syncope, neurogenic syncope, hypersensitive Carotid sinus, neurovascular syndrome, arrythmias, addiction disorders involving addictions to behaviors, HIV-1 associated dementia, AIDS dementia complex, HIV encephalopathy, HIV related neuralgias, AIDS related neuralgias, epilepsy, attention deficit hyperactivity disorder, a somatoform disorder selected from the group consisting of somitization disorder, hypochondriasis, somatoform pain disorder and undifferentiated somatoform disorder, and somatic symptoms selected from the group consisting of loss of appetite, insomnia, interrupted sleep, early morning awakening, tired awakening, loss of libido, restlessness, fatigue, constipation, dyspepsia, heart palpitations, headache, neck pain, back pain, limb pain, joint pain, abdominal pain, dizziness, nausea, heartburn, nervousness, tremors, burning and tingling sensations, morning stiffness, abdominal pain, abdominal distention, gurgling, diarrhea, and the symptoms associated with generalized anxiety disorder, comprising an amount of a compound of Formula I, or a pharmaceutically acceptable salt or solvate thereof, and a pharmaceutically acceptable carrier, wherein the amount of said compound of Formula I is effective in (1) antagonizing an NK-1 receptor, and/or (2) treating said condition or disorder.

Another practice of the invention relates to a method of antagonizing an NK-1 receptor in a mammal comprising administering to said mammal an NK-1 antagonizing amount of a compound of Formula I, or a pharmaceutically acceptable salt or solvate thereof.

Another practice of the invention relates to a method of treating a condition or disorder associated with the activity, preferably the overactivity, of NK-1 receptors in a mammal comprising administering to said mammal an amount of a compound of Formula I, or a pharmaceutically acceptable salt or solvate thereof, wherein the amount of said compound of Formula I is effective in (1) antagonizing the NK-1 receptor, and/or (2) treating said condition or disorder, wherein said mammal is in need of said treatment.

Another practice of the invention relates to a method of treating in a mammal a condition or disorder selected from the group consisting of sleep disorders, autism, pervasive development disorder, rheumatoid arthritis, emesis, major depressive disorders, osteoarthritis, fibromyalgia, human immunodeficiency virus (HIV) infections, dissociative disorders, anorexia, bulimia, ulcerative colitis, Crohn's disease, irritable bowel syndrome, functional abdominal pain, chronic fatigue syndrome, sudden infant death syndrome (SIDS), overactive bladder, chronic cystitis, chemotherapy induced cystitis, cough, angiotensin converting enzyme (ACE) induced cough, itch, hiccups, premenstrual syndrome, premenstrual dysphoric disorder, schizophrenia, schizoaffective disorder, delusional disorder, substance-induced psychotic disorder, brief psychotic disorder, shared psychotic disorder, psychotic disorder due to a general medical condition, schizophreniform disorder, amenorrheic disorders such as desmenorrhea, obesity, epilepsy, primary movement disorders, spasticities, Scott's syndrome, Tourette's syndrome, palsys, amyolateral sclerosis (ALS), akinetic-rigid disorders, akinesias, dyskinesias, restless leg syndrome, movement disorders associated with Parkinson's disease or Huntington's disease, mastalgia syndromes, motion sickness, immune dysfunctions, generalized anxiety disorder, panic disorder, social phobia, agoraphobia, specific phobias, obsessive-compulsive disorder, post-traumatic stress disorder, major depression, single episode depression, recurrent depression, child abuse induced depression, postpartum depression, dysthemia, cyclothymia, bipolar disorder, neurocardiac syncope, neurogenic syncope, hypersensitive Carotid sinus, neurovascular syndrome, arrythmias, addiction disorders involving addictions to behaviors, HIV-1 associated dementia, AIDS dementia complex, HIV encephalopathy, HIV related neuralgias, AIDS related neuralgias, epilepsy, attention deficit hyperactivity disorder, a somatoform disorder selected from the group consisting of somitization disorder, hypochondriasis, somatoform pain disorder and undifferentiated somatoform disorder, and somatic symptoms selected from the group consisting of loss of appetite, insomnia, interrupted sleep, early morning awakening, tired awakening, loss of libido, restlessness, fatigue, constipation, dyspepsia, heart palpitations, headache, neck pain, back pain, limb pain, joint pain, abdominal pain, dizziness, nausea, heartburn, nervousness, tremors, burning and tingling sensations, morning stiffness, abdominal pain, abdominal distention, gurgling, diarrhea, and the symptoms associated with generalized anxiety disorder, comprising administering to said mammal an amount a compound of Formula I, or a pharmaceutically acceptable salt or solvate thereof, wherein the amount of said compound of Formula I is effective in (1) antagonizing an NK-1 receptor and/or (2) treating said condition or disorder, wherein said mammal is in need of said treatment.

In another aspect, the compound of Formula I is used in an assay of NK-1 binding wherein said compound exhibits a Ki of about 5 nM or less, preferably 2 nM or less, more preferably about 0.1 nM or less.

DETAILED DESCRIPTION OF THE INVENTION

The present invention relates to a compound (that in various practices comprises piperidine, pyrrolidine, and diazepane derivatives) which is an antagonist of tachykinins, including substance P and other neurokinins (NK), such as NK-1, and is thus useful for the treatment of neurokinin-mediated conditions, among other things.

In a preferred embodiment, the compound of the invention has Formula I, above, including pharmaceutically acceptable salts thereof, e.g. acid addition salts, base addition salts, and prodrugs and solvates thereof. Without limitation, examples of pharmaceutically acceptable acid addition salts of the compounds of Formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malate, di-p-toluoyl tartaric acid, lactic acid, acetic acid, trifluoroacetic acid, mandelic acid.

The compound of Formula I can have optical centers and thus occur in different enantiomeric configurations. The invention includes all enantiomers, diastereomers, and other stereoisomers and optical isomers of such compound of Formula I, as well as racemic and other mixtures thereof. For example, the compound of Formula I includes (R) and (S) enantiomers and cis and trans isomers. The present invention further includes all radiolabelled forms of the compound of Formula I. Preferred radiolabelled compounds are those wherein the radiolabels are selected from as $^3$H, $^{11}$C, $^{14}$C, $^{18}$F, $^{123}$I and $^{125}$I. Such radiolabelled compounds are useful as research and diagnostic tools in metabolism pharmacokinetics studies and in binding assays in animals and man.

As appreciated by the artisan, the use of Formula I is a convenience and the invention is understood to envision and embrace each and every species thereunder as though individually identified and set forth herein. Thus the present invention severally contemplates each species separately and any and all combinations and permutations of species falling within Formula I.

In a first preferred practice of the compound of Formula I, L is O, M is —NR$^2$R$^3$, p is 0 or 1, m is 0 or 1; n is 1; R$^1$ and R$^2$ are each independently selected from H, (C$_1$-C$_6$) alkyl, benzyl,
—CH$_2$-heterocycloalkyl, and —CH$_2$-heteroaryl, wherein each of said benzyl, —CH$_2$-heterocycloalkyl, and —CH$_3$-heteroaryl are optionally substituted with 1-3 moieties independently selected from X', Y' and Z'; R$^3$, is H, or (C$_1$-C$_8$) alkyl; and X, Y, X', Y' and Z' are each independently selected from H, (C$_1$-C$_6$)alkyl, CF$_3$, OH, —O(C$_1$-C$_6$)alky), halogen, and CN. In one embodiment of this practice, R$^3$ and R$^4$ are each methyl. Nonlimiting examples of compounds in this preferred practice include:

1-hydroxy-2-phenyl-3-aza-bicyclo[3.1.0]hexane-3-carboxylicacid[1-(3,5-bis-trifluoromethyl-phenyl)-ethyl]-methyl-amide;

1-hydroxy-2-phenyl-3-aza-bicyclo[3.1.0]hexane-3-carboxylicacid[1-(3,5-bis-trifluoromethyl-phenyl)-ethyl]-methyl-amide;

or pharmaceutically acceptable salts or solvates thereof.

In a second preferred practice of the compound of Formula I, L is O, M is $R^2$, p is 1, m is 0 or 1; n is 0 or 1; $R^1$ and $R^2$ are each independently selected from H, $CH_3$, $(C_1-C_6)$alkyl, benzyl, —$CH_2$-heterocycloalkyl, and —$CH_2$-heteroaryl, wherein each of said benzyl, —$CH_2$-heterocycloalkyl, and —$CH_2$-heteroaryl is optionally substituted with 1-3 moieties independently selected from X', Y' and Z'; and X, Y, X', Y' and Z' are each independently selected from H, $(C_1-C_6)$alkyl, $CF_3$, OH, —O$(C_1-C_6)$alkyl, halogen, and CN. Non-limiting examples of this preferred practice include:

1-(3,5-bis-trifluoromethyl-benzyloxymethyl)-2-phenyl-3-aza-bicyclo[3.1.0]hexane;

{5-[1-(3,5-bis-trifluoromethyl-benzyloxymethyl)-2-phenyl-3-aza-bicyclo[3.1.0]hex-3-ylmethyl]-1H-[1,2,3]triazol-4-ylmethyl}-dimethyl-amine;

1-(3,5-bis-trifluoromethyl-benzyloxymethyl)-2-phenyl-3-aza-bicyclo[3.1.0]hexane-3-carboxylicacid[1-(3,5-bis-trifluoromethyl-phenyl)-ethyl]-methyl-amide;

1-hydroxymethyl-2-phenyl-3-aza-bicyclo[3.1.0]hexane-3-carboxylicacid[1-(3,5-bis-trifluoromethyl-phenyl)-ethyl]-methyl-amide;

2-(4-fluoro-2-methyl-phenyl)-1-hydroxymethyl-3-aza-bicyclo[3.1.0]hexane-3-carboxylicacid[1-(3,5-bis-trifluoromethyl-phenyl)-ethyl]-methyl-amide;

2-(4-fluoro-2-methyl-phenyl)-1-hydroxymethyl-3-aza-bicyclo[3.1.0]hexane-3-carboxylicacid[1-(3,5-bis-trifluoromethyl-phenyl)-ethyl]-methyl-amide;

or pharmaceutically acceptable salts or solvates thereof.

In a third preferred practice of the compound of Formula I, L is $NR^5$, M is $R^2$, p is 1, m is 0 or 1; n is 0 or 1; $R^1$ and $R^2$ are each independently selected from H, $(C_1-C_6)$alkyl, benzyl, —$CH_2$-heterocycloalkyl, and —$CH_2$-heteroaryl, wherein each of said benzyl, —$CH_2$-heterocycloalkyl, and —$CH_2$-heteroaryl is optionally substituted with 1-3 moieties independently selected from X', Y' and Z'; $R^5$ is H, $CH_3$, or $(C_1-C_6)$alkyl; and X, Y, X', Y' and Z' are each independently selected from H, $CH_3$, $(C_1-C_6)$alkyl, $CF_3$, OH, —O$(C_1-C_6)$alkyl), halogen, and CN. Nonlimiting examples of this preferred practice include:

6-methoxy-3-methyl-5-[(2-phenyl-3-aza-bicyclo[3.1.0]hex-1-ylamino)-methyl]-1,1a,3,7b-tetrahydro-3-aza-cyclopropa[a]naphthalen-2-one;

6-methoxy-3-methyl-5-{[(2-phenyl-3-aza-bicyclo[3.1.0]hex-1-ylmethyl)-amino]-methyl}-1,1a,3,7b-tetrahydro-3-aza-cyclopropa[a]naphthalen-2-one;

(6-methoxy-1-methyl-1-trifluoromethyl-isochroman-7-ylmethyl)-(2-phenyl-3-aza-bicyclo[3.1.0]hex-1-ylmethyl)-amine;

1-methylaminomethyl-2-phenyl-3-aza-bicyclo[3.1.0]hexane-3-carboxylicacid[1-(3,5-bis-trifluoromethyl-phenyl)-ethyl]-methyl-amide;

1-aminomethyl-2-phenyl-3-aza-bicyclo[3.1.0]hexane-3-carboxylicacid[1-(3,5-bis-trifluoromethyl-phenyl)-ethyl]-methyl-amide;

or pharmaceutically acceptable salts or solvates thereof.

In a fourth preferred practice of the compound of Formula I, L is O, M is $R^2$, p is 0, m is 0 or 1; n is 0 or 1; $R^1$ and $R^2$ are each independently selected from H, $(C_1-C_6)$alkyl, benzyl, —$CH_3$-heterocycloalkyl and —$CH_2$-heteroaryl, wherein each of said benzyl, —$CH_2$-heterocycloalkyl, and —$CH_2$-heteroaryl is optionally substituted with 1-3 moieties independently selected from X', Y' and Z'; and X, Y, X', Y' and Z' are each independently selected from H, $CH_3$, $(C_1-C_6)$alkyl, $CF_3$, OH, —O$(C_1-C_6)$alkyl, halogen, and CN. Non-limiting examples of this preferred practice include:

5-[1-(3,5-bis-trifluoromethyl-benzyloxy)-2-phenyl-3-aza-bicyclo[3.1.0]hex-3-ylmethyl]-2,4-dihydro-[1,2,4]triazol-3-one;

5-[1-(3,5-bis-trifluoromethyl-benzyloxy)-2-phenyl-3-aza-bicyclo[3.1.0]hex-3-ylmethyl]-2,4-dihydro-[1,2,4]triazol-3-one;

{5-[1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

{5-[1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

1-(3,5-bis-trifluoromethyl-benzyloxy)-2-phenyl-3-aza-bicyclo[3.1.0]hexane;

1-(3,5-Bis-trifluoromethyl-benzyloxy)-2-phenyl-3-aza-bicyclo[3.1.0]hexane;

or pharmaceutically acceptable salts or solvates thereof.

In a fifth preferred practice of the compound of Formula I, L=—$NR^5$, M=—$NR^2R^4$, p is 1, m is 0 or 1; n is 1; $R^1$ and $R^2$ are each independently H, $CH_3$, $(C_1-C_6)$alkyl, benzyl, —$CH_3$-heterocycloalkyl, or —$CH_3$-heteroaryl, wherein each of said benzyl, —$CH_3$-heterocycloalkyl, or —$CH_3$-heteroaryl is optionally substituted with 1-3 moieties independently selected from X', Y' and Z'; $R^4$ and $R^5$ are each independently selected from H, $CH_3$, and $(C_1-C_6)$alkyl; and X, Y, X', Y' and Z' are each independently selected from H, $CH_3$, $(C_1-C_6)$alkyl, $CF_3$, OH, —O$(C_1-C_6)$alkyl, halogen, and CN. Non-limiting examples of this preferred practice include:

1-amino-2-phenyl-3-aza-bicyclo[3.1.0]hexane-3-carboxylicacid[1-(3,5-bis-trifluoromethyl-phenyl)-ethyl]-methyl-amide;

1-aminomethyl-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

or pharmaceutically acceptable salts or solvates thereof.

In a sixth preferred practice of the compound of Formula I, L is —$NR^5$, M is $R^2$, p is 0, m is 0 or 1; n is 0 or 1; $R^1$ and $R^2$ are each independently selected from H, $CH_3$, $(C_1-C_6)$alkyl, benzyl, —$CH_2$-heterocycloalkyl, and —$CH_2$-heteroaryl, wherein each of said benzyl, —$CH_2$-heterocycloalkyl, and —$CH_2$-heteroaryl is optionally substituted with 1-3 moieties independently selected from X', Y' and Z'; $R^5$ is H, $CH_3$, or $(C_1-C_6)$alkyl; and X, Y, X', Y' and Z' are each independently selected from H, $CH_3$, $(C_1-C_6)$alkyl, $CF_3$, OH, $OCH_3$, —O$(C_1-C_6)$alkyl), halogen, and CN. Non-limiting examples of this preferred practice include:

6-methoxy-3-methyl-5-[(2-phenyl-3-aza-bicyclo[3.1.0]hex-1-ylamino)-methyl]-1,1a,3,7b-tetrahydro-3-aza-cyclopropa[a]naphthalen-2-one;

(5-tert-butyl-2-methoxy-benzyl)-(2-phenyl-3-aza-bicyclo[3.1.0]hex-1-yl)-amine;

6-methoxy-1-methyl-1-trifluoromethyl-isochroman-7-yl-methyl)-(2-phenyl-3-aza-bicyclo[3.1.0]hex-1-yl)-amine;

or pharmaceutically acceptable salts or solvates thereof.

In a seventh preferred practice of the compound of Formula I, L is O, M is —$NR^2R^3$, p is 1, m is 0 or 1; n is 0 or 1; $R^1$ and $R^2$ are each independently selected from H, $CH_3$, ($C_1$-$C_6$)alkyl, benzyl, —$CH_2$-heterocycloalkyl, and —$CH_3$-heteroaryl, wherein each of said benzyl, —$CH_2$-heterocycloalkyl, and —$CH_2$-heteroaryl is optionally substituted with 1-3 moieties independently selected from X', Y' and Z'; $R^3$ is H, $CH_3$, or $C_{1-6}$alkyl; and X, Y, X', Y' and Z' are each independently selected from H, ($C_1$-$C_6$)alkyl, $CF_3$, OH, $OCH_3$, —O($C_1$-$C_6$)alkyl, halogen, and CN. Non-limiting examples of this preferred practice include:

2-phenyl-3-aza-bicyclo[3.1.0]hexane-1-carboxylicacid [1-(3,5-bis-trifluoromethyl-phenyl)-ethyl]-methyl-amide;

3-benzyl-2-phenyl-3-aza-bicyclo[3.1.0]hexane-1-carboxylicacid[1-(3,5-bis-trifluoromethyl-phenyl)-ethyl]-methyl-amide;

or pharmaceutically acceptable salts or solvates thereof.

Preferred compounds that are listed above include:

5-[1-(3,5-bis-trifluoromethyl-benzyloxy)-2-phenyl-3-aza-bicyclo[3.1.0]hex-3-ylmethyl]-2,4-dihydro-[1,2,4]triazol-3-one;

5-[1-(3,5-bis-trifluoromethyl-benzyloxy)-2-phenyl-3-aza-bicyclo[3.1.0]hex-3-ylmethyl]-2,4-dihydro-[1,2,4]triazol-3-one;

{5-[1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

{5-[1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

1-(3,5-bis-trifluoromethyl-benzyloxy)-2-phenyl-3-aza-bicyclo[3.1.0]hexane;

1-(3,5-Bis-trifluoromethyl-benzyloxy)-2-phenyl-3-aza-bicyclo[3.1.0]hexane;

1-amino-2-phenyl-3-aza-bicyclo[3.1.0]hexane-3-carboxylicacid[1-(3,5-bis-trifluoromethyl-phenyl)-ethyl]-methyl-amide;

1-aminomethyl-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

2-phenyl-3-aza-bicyclo[3.1.0]hexane-1-carboxylicacid [1-(3,5-bis-trifluoromethyl-phenyl)-ethyl]-methyl-amide;

3-benzyl-2-phenyl-3-aza-bicyclo[3.1.0]hexane-1-carboxylicacid[1-(3,5-bis-trifluoromethyl-phenyl)-ethyl]-methyl-amide;

or pharmaceutically acceptable salts or solvates thereof.

The present invention also relates to a method of treating one or more disorders or conditions such as sleep disorders (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders); pervasive development disorder; rheumatoid arthritis; osteoarthritis; fibromyalgia; human immunodeficiency virus (HIV) infections; dissociative disorders such as body dysmorphic disorders; eating disorder such as anorexia and bulimia, ulcerative colitis; Crohn's disease; irritable bowel syndrome; functional abdominal pain; chronic fatigue syndrome; sudden infant death syndrome (SIDS); overactive bladder; chronic cystitis; chemotherapy induced cystitis; cough, angiotensin converting enzyme (ACE) induced cough; itch; hiccups; premenstrual syndrome: premenstrual dysphoric disorder; schizophrenia; schizoaffective disorder; delusional disorder; substance-induced psychotic disorder; brief psychotic disorder; shared psychotic disorder; psychotic disorder due to a general medical condition; schizophreniform disorder; amenorrheic disorders such as desmenorrhea; obesity; epilepsy: movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease; mastalgia syndromes; motion sickness; immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, and human-animal interaction stress in dogs); generalized anxiety disorder; panic disorder; phobias, including social phobia, agoraphobia, and specific phobias; obsessive-compulsive disorder; emesis; post-traumatic stress disorder; depressive disorders including major depressive disorder, single episode depression, recurrent depression, child abuse induced depression, postpartum depression and dysthymia; cyclothymia; bipolar disorder; neurocardiac disorders such as neurocardiac syncope, neurogenic syncope, hypersensitive Carotid sinus, neurovascular syndrome and arrythmias including arrythmias secondary to gastrointestinal disturbances; addiction disorders involving addictions to behaviors (e.g., addictions to gambling and other addictive behaviors); HIV-1 associated dementia; HIV encephalopathy; AIDS dementia complex (ADC); HIV related neuralgias; AIDS related neuralgias; epilepsy; and attention deficit hyperactivity disorder in a mammal, comprising administering to said mammal an amount of a compound of Formula I, or a pharmaceutically acceptable salt or solvate thereof, that is effective in antagonizing the effect of substance P at its receptor site, wherein said mammal is in need of said treatment.

Other more specific methods of this invention include any of the above methods wherein the disorder or condition that is being treated is selected from movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease.

Other more specific methods of this invention include the above methods wherein the disorder or condition that is being treated is major depressive disorder.

Other more specific methods of this invention include the above methods wherein the disorder or condition that is being treated is major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is somatic major depressive disorder.

Other more specific methods of this invention include the above methods wherein the disorder or condition that is being treated is somatic major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is irritable bowel syndrome.

Other more specific methods of this invention include the above methods wherein the disorder or condition that is being treated is an HIV infection.

Other more specific methods of this invention include the above methods wherein the disorder or condition that is being treated is selected from HIV-1 associated dementia, AIDS dementia complex (ADC), HIV encephalopathy, and HIV related neuralgias.

Other more specific methods of this invention include the above methods wherein the disorder or condition that is being is immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, or human-animal interaction stress in dogs).

Other more specific methods of this invention include the above methods wherein the disorder or condition that is being treated is neurocardiac disorders such as neurocardiac syncope, neurogenic syncope, hypersensitive Carotid sinus, neurovascular syndrome or arrythmias including arrythmias secondary to gastrointestinal disturbances.

Other more specific methods of this invention include the above methods wherein the disorder or condition that is being treated is major depression, single episode depression, recurrent depression, child abuse induced depression, post-partum depression, dysthymia, cyclothymia or bipolar disorder.

Other more specific methods of this invention include the above methods wherein the disorder or condition that is being treated is major depression, single episode depression, recurrent depression, child abuse induced depression, post-partum depression, dysthymia, cyclothymia or bipolar disorder, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is body dysmorphic disorders and eating disorders such as anorexia and bulimia.

Other more specific methods of this invention include the above methods wherein the disorder or condition that is being treated is schizophrenia, schizoaffective disorder, delusional disorder, substance-induced psychotic disorder, brief psychotic disorder, shared psychotic disorder, psychotic disorder due to a general medical condition, or schizophreniform disorder.

Other more specific methods of this invention include the above methods wherein the disorder or condition that is being treated is premenstrual syndrome, premenstrual dysphoric disorder, and amenorrheic disorders such as desmenorrhea.

Other more specific methods of this invention include the above methods wherein the disorder or condition that is being treated is premenstrual syndrome, premenstrual dysphoric disorder, or amenorrheic disorders such as desmenorrhea, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is Crohn's disease, irritable bowel syndrome or functional abdominal pain.

Other more specific methods of this invention include the above methods wherein the disorder or condition that is being treated is selected from autism, pervasive development disorder, or attention deficit hyperactivity disorder.

Other more specific method of this invention include the above methods wherein the disorder or condition that is being treated is selected from chronic fatigue syndrome, sudden infant death syndrome (SIDS), obesity, or epilepsy.

Other more specific methods of this invention include the above methods wherein the disorder or condition that is being treated is generalized anxiety disorder, panic disorder, obsessive-compulsive disorder, post-traumatic stress disorder, or phobias, including social phobia, agoraphobia, and specific phobias.

Other more specific methods of this invention include the above methods wherein the disorder or condition that is being treated is generalized anxiety disorder, panic disorder, obsessive-compulsive disorder, post-traumatic stress disorder, and phobias, including social phobia, agoraphobia, or specific phobias, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is cough, angiotensin converting enzyme (ACE) induced cough, itch, or hiccups.

Other more specific methods of this invention include the above methods wherein the disorder or condition that is being treated is overactive bladder; chronic cystitis or chemotherapy induced cystitis.

Other more specific methods of this invention include the above methods wherein the disorder or condition that is being treated is attention deficit hyperactivity disorder.

Other more specific methods of this invention include the above methods wherein the disorder or condition that is being treated is a sleep disorder (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders).

The present invention also relates to a method of treating a disorder or condition selected from the group consisting of pain resulting from soft tissue and peripheral damage, such as acute trauma; postherpetic neuralgia, trigeminal neuralgia, segmental or intercostal neuralgia and other neuralgias; pain associated with osteoarthritis and rheumatoid arthritis; musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, neuropathic lower back pain, HIV related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain in a mammal, comprising administering to said mammal an amount of a compound of Formula I as defined above, or a pharmaceutically acceptable salt or solvate thereof, that is effective in treating such disorder or condition.

The present invention also relates to a method of treating a disorder or condition selected from the group consisting of pain resulting from soft tissue and peripheral damage, such as acute trauma; postherpetic neuralgia, trigeminal neuralgia, segmental or intercostal neuralgia and other neuralgias; pain associated with osteoarthritis and rheumatoid arthritis; musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, neuropathic lower back pain, HIV related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased bladder contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain in a mammal, comprising administering to said mammal an amount of a compound of Formula I as defined above, or a pharmaceutically acceptable salt thereof, that is effective in antagonizing the effect of substance P at its receptor site.

Other more specific methods of this invention include the above methods wherein the disorder or condition that is being treated is neuropathic pain.

Other more specific methods of this invention include the above methods wherein the disorder or condition that is being treated is HIV related neuralgia.

Other more specific methods of this invention include the above methods wherein the disorder or condition that is being treated is pain associated with fibromyalgia.

Other more specific methods of this invention include the above methods wherein the disorder or condition that is being treated is neuropathic lower back pain, HIV related neuropathic pain, diabetic neuropathic pain, arachnoiditis or neuropathic and non-neuropathic pain associated with carcinoma.

Unless otherwise indicated, the following terms and related variations of same as used herein representatively have the meanings ascribed:

"Halogen" and "halo" and the like includes fluoro, chloro, bromo and iodo.

"Alkyl" including as appears in any terms such as "alkoxy" and "alkyoxycarbonyl," or in any substutuents such as —O—C$_{(1-6)}$alkyl, —O—C$_{(1-6)}$alkyl, or —C$^{(1-6)}$alkyl-C(O)—R$^6$ includes saturated monovalent hydrocarbon radicals having straight or branched moieties. Examples of alkyl groups include, but are not limited to, methyl, ethyl, n-propyl, isopropyl, and t-butyl.

"Alkoxy" is —O—C$_{(1-6)}$alkyl.

"Alkoxycarbonyl" is —C(=O)—OR$^A$ wherein R$^A$ is C$_{(1-6)}$alkyl as defined herein.

Ring system substituent" means a substituent attached to an aromatic or non-aromatic ring system which, for example, replaces an available hydrogen on the ring system. Ring system substituents can be the same or different, each being independently selected from the group consisting of alkyl, —CH$_2$—N(CH$_3$)$_2$, cycloalkyl, aryl, —O-aryl, heteroaryl, aralkyl, alkylaryl, heteroaralkyl, alkylheteroaryl, hydroxy, hydroxyalkyl, (C$_1$-C$_6$)alkoxy, aryloxy, aralkoxy, acyl, aroyl, halo, nitro, cyano, carboxy, and heterocyclyl.

"Cycloalkyl" includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl; and bicycloalkyl and tricycloalkyl groups that are non-aromatic saturated carbocyclic groups consisting of two or three rings respectively, wherein said rings share at least one carbon atom. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro [4.4]nonyl, spiro[4.3]octyl, and spiro[4.2]heptyl. An example of a tricycloalkyl group is adamantanyl. Cycloalkyl groups also include groups that are substituted with one or more oxo moieties. Examples of such groups with oxo moieties are oxocyclopentyl and oxocyclohexyl. Cycloalkyl groups can be substituted with one or more ring system substituents.

"Alkenyl" includes alkyl moieties having at least one carbon-carbon double bond wherein alkyl is as defined herein; e.g. ethenyl and propenyl.

"Acyl" is —C(=)—R$^B$ wherein R$^B$ is hydrogen, C$_{1-6}$alkyl, C$_{3-7}$cycloalkyl, C$_{5-10}$aryl and the like; e.g. formyl, acetyl, propionyl, benzoyl and the like.

"Amino" is —NR$^C$R$^D$ wherein R$^C$ and R$^D$ are each independently hydrogen or (C$_1$-C$_6$)alkyl.

"Amido" includes the groups —C(=O)—NR$^E$R$^F$ (C-amido) and —NR$^E$—C(=O)—R$^F$ (N-amido), wherein R$^E$ and R$^F$ are each independently hydrogen, C$_{1-5}$alkyl or C$_{1-6}$alkoxy.

"Aryl" refers to monocyclic and multicyclic groups which includes an organic radical derived from an aromatic hydrocarbon by removal of one hydrogen, such as phenyl, naphthyl, tetrahydonaphthyhl, indenyl, indanyl, and fluorenyl; and fused ring groups wherein at least one ring is aromatic. The aryl groups of this invention can also include ring systems substituted with one or more oxo moieties.

"Oxo" is =O.

"Heterocyclic" refers to non-aromatic monocyclic and multicyclic groups containing one or more heteroatoms, preferably from one to four heteroatoms, each selected from O, S and N. Heterocyclic groups also include ring systems substituted with one or more oxo moieties. Non-limiting examples of heterocyclic groups are aziridinyl, azetidinyl, dihydropyrolyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl. Heterocyclic groups can be substituted with one or more ring system substituents.

"Heteroaryl" refers to aromatic groups, which may be monocylcic or multicyclic, containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Non-limtiting examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroguinolyl, tetrazolyl, furyl, furanyl, thienyl, isoxazolyl, thiazolyl, chromanyl, isochromanyl, thiochromanyl, thiophenyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl; benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl. Heteroaryl groups can be substituted with one or more ring system substituents.

"Heterobicyclic" refers to non-aromatic two-ringed cyclic groups, including bridged ring systems, wherein at least one of the rings contains a heteroatom of O, S or N, including without limitation azabicyclics such as 3-azabicyclo[3.1.0] hexanyl and 3-azabicyclo[4.1.0]heptanyl. Heterobicyclic groups can be substituted with one or more ring system substituents.

The foregoing groups, as derived from the compounds listed above, can be C-attached or N-attached where such is possible. For instance, a group derived from pyrrole can be pyrrol-1-yl (N-attached) or pyrrol-3-yl (C-attached). The terms referring to the groups also encompass all possible tautomers.

"Treatment" and "treating" refers to reversing, alleviating, inhibiting the progress of, or preventing the disorder or condition to which such term applies, or one or more symptoms of such condition or disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder. The term "treatment", as used herein, refers to the act of treating, as "treating" is defined immediately above.

"Mammal" refers to any member of the class "Mammalia", including, but not limited to, humans, dogs, and cats.

"Solvates" of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$.

The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

The term "one or more substituents," as used herein, includes from one to the maximum number of substituents possible based on the number of available bonding sites.

NK-Mediated Conditions

The present invention also relates to a method of treating one or more disorders or conditions such as sleep disorders (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders); pervasive development disorder; rheumatoid arthritis; osteoarthritis; fibromyalgia; human immunodeficiency virus (HIV) infections; dissociative disorders such as body dysmorphic disorders; eating disorder such as anorexia and bulimia, ulcerative colitis; Crohn's disease; irritable bowel syndrome; functional abdominal pain; chronic fatigue syndrome; sudden infant death syndrome (SIDS); overactive bladder; chronic cystitis; chemotherapy induced cystitis; cough, angiotensin converting enzyme (ACE) induced cough; itch; hiccups; premenstrual syndrome: premenstrual dysphoric disorder; schizophrenia; schizoaffective disorder; delusional disorder; substance-induced psychotic disorder; brief psychotic disorder; shared psychotic disorder; psychotic disorder due to a general medical condition; schizophreniform disorder; amenorrheic disorders such as desmenorrhea; obesity; epilepsy: movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease; mastalgia syndromes; motion sickness; immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, and human-animal interaction stress in dogs); generalized anxiety disorder; panic disorder; phobias, including social phobia, agoraphobia, and specific phobias; obsessive-compulsive disorder; post-traumatic stress disorder; depression including major depressive disorder, single episode depression, recurrent depression, child abuse induced depression, postpartum depression and dysthymia; cyclothymia; bipolar disorder; neurocardiac disorders such as neurocardiac syncope, neurogenic syncope, hypersensitive Carotid sinus, neurovascular syndrome and arrythmias including arrythmias secondary to gastrointestinal disturbances; addiction disorders involving addictions to behaviors (e.g., addictions to gambling and other addictive behaviors); HIV-1 associated dementia; HIV encephalopathy; AIDS dementia complex (ADC); HIV related neuralgias; AIDS related neuralgias; epilepsy; and attention deficit hyperactivity disorder in a mammal, comprising administering to said mammal an amount of a compound of Formula I as defined above, or a pharmaceutically acceptable salt thereof, that is effective in antagonizing the effect of substance P at its receptor site.

Other more specific methods of this invention include any of the above methods wherein the disorder or condition that is being treated is selected from movement disorders such as primary movement disorders, spasticities, Scott's syndrome, Tourette's syndrome, palsys (e.g., Bell's palsy, cerebral palsy, birth palsy, brachial palsy, wasting palsy, ischemic palsy, progressive bulbar palsy and other palsys), amyolateral sclerosis (ALS), akinetic-rigid disorders, akinesias, dyskinesias (e.g., familial paroxysmal dyskinesia, tardive dyskinesia, tremor, chorea, myoclonus, tics and other dyskinesias) restless leg syndrome and movement disorders associated with Parkinson's disease or Huntington's disease.

Other more specific methods of this invention include the above methods wherein the disorder or condition that is being treated is major depressive disorder.

Other more specific methods of this invention include the above methods wherein the disorder or condition that is being treated is major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is somatic major depressive disorder.

Other more specific methods of this invention include the above methods wherein the disorder or condition that is being treated is somatic major depressive disorder, and wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is irritable bowel syndrome.

Other more specific methods of this invention include the above methods wherein the disorder or condition that is being treated is an HIV infection.

Other more specific methods of this invention include the above methods wherein the disorder or condition that is being treated is selected from HIV-1 associated dementia, AIDS dementia complex (ADC), HIV encephalopathy, and HIV related neuralgias.

Other more specific methods of this invention include the above methods wherein the disorder or condition that is being is immune dysfunctions (e.g., stress induced immune dysfunctions such as idiopathic immune dysfunctions, post infection immune dysfunctions, post lumpectomy immune dysfunctions, porcine stress syndrome, bovine shipping fever, equine paroxysmal fibrillation, confinement dysfunction in chicken, sheering stress in sheep, or human-animal interaction stress in dogs).

Other more specific methods of this invention include the above methods wherein the disorder or condition that is being treated is neurocardiac disorders such as neurocardiac syncope, neurogenic syncope, hypersensitive Carotid sinus, neurovascular syndrome or arrythmias including arrythmias secondary to gastrointestinal disturbances.

Other more specific methods of this invention include the above methods wherein the disorder or condition that is being treated is major depression, single episode depression, recurrent depression, child abuse induced depression, post-partum depression, dysthymia, cyclothymia or bipolar disorder.

Other more specific methods of this invention include the above methods wherein the disorder or condition that is being treated is major depression, single episode depression, recurrent depression, child abuse induced depression, post-partum depression, dysthymia, cyclothymia or bipolar disorder, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is body dysmorphic disorders and eating disorders such as anorexia and bulimia.

Other more specific methods of this invention include the above methods wherein the disorder or condition that is being treated is schizophrenia, schizoaffective disorder, delusional disorder, substance-induced psychotic disorder, brief psychotic disorder, shared psychotic disorder, psychotic disorder due to a general medical condition, or schizophreniform disorder.

Other more specific methods of this invention include the above methods wherein the disorder or condition that is being treated is premenstrual syndrome, premenstrual dysphoric disorder, and amenorrheic disorders such as desmenorrhea.

Other more specific methods of this invention include the above methods wherein the disorder or condition that is being treated is premenstrual syndrome, premenstrual dysphoric disorder, or amenorrheic disorders such as desmenorrhea, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is Crohn's disease, irritable bowel syndrome or functional abdominal pain.

Other more specific methods of this invention include the above methods wherein the disorder or condition that is being treated is selected from autism, pervasive development disorder, or attention deficit hyperactivity disorder.

Other more specific method of this invention include the above methods wherein the disorder or condition that is being treated is selected from chronic fatigue syndrome, sudden infant death syndrome (SIDS), obesity, or epilepsy.

Other more specific methods of this invention include the above methods wherein the disorder or condition that is being treated is generalized anxiety disorder, panic disorder, obsessive-compulsive disorder, post-traumatic stress disorder, or phobias, including social phobia, agoraphobia, and specific phobias.

Other more specific methods of this invention include the above methods wherein the disorder or condition that is being treated is generalized anxiety disorder, panic disorder, obsessive-compulsive disorder, post-traumatic stress disorder, and phobias, including social phobia, agoraphobia, or specific phobias, wherein the mammal being treated is a human who has not exhibited an adequate treatment response following treatment for the same disorder or condition with a selective serotonin reuptake inhibitor (SSRI). The phrase "adequate treatment response" to an SSRI, as used herein, means that the SSRI with which the human patient was treated in accordance with a treatment protocol accepted by those of skill in the art of treating the disorder or condition for which such patient was being treated did not result in a degree of amelioration of the symptoms of such disorder or condition that would cause such persons of skill in the art to consider such treatment successful.

Other more specific methods of this invention include the above methods wherein the disorder or condition that is being treated is cough, angiotensin converting enzyme (ACE) induced cough, itch, or hiccups.

Other more specific methods of this invention include the above methods wherein the disorder or condition that is being treated is overactive bladder; chronic cystitis or chemotherapy induced cystitis.

Other more specific methods of this invention include the above methods wherein the disorder or condition that is being treated is attention deficit hyperactivity disorder.

Other more specific methods of this invention include the above methods wherein the disorder or condition that is being treated is a sleep disorder (e.g., sleep apnea, insomnia, somnambulism, sleep deprivation, REM sleep disorders, hypersomnia, parasomnias, sleep-wake cycle disorders, narcolepsy, sleep disorders associated with shift work or irregular work schedules, and other sleep disorders).

Other more specific methods of this invention include the above methods wherein the disorder or condition that is being treated is neuropathic pain.

Other more specific methods of this invention include the above methods wherein the disorder or condition that is being treated is HIV related neuralgia.

Other more specific methods of this invention include the above methods wherein the disorder or condition that is being treated is pain associated with fibromyalgia.

Other more specific methods of this invention include the above methods wherein the disorder or condition that is being treated is neuropathic lower back pain, HIV related neuropathic pain, diabetic neuropathic pain, arachnoiditis or neuropathic and non-neuropathic pain associated with carcinoma.

Specific preferred methods of this invention include the above methods wherein the compound of Formula I that is employed in such method is one or more of the following NK1 antagonists:

(1aS,2R)-6-Methoxy-3-methyl-5-[((1R,2S,5S)-2-phenyl-3-aza-bicyclo[3.1.0]hex-1-ylamino)-methyl]-1,1a,3,7b-tetrahydro-3-aza-cyclopropa[a]naphthalen-2-one;

(5-tert-Butyl-2-methoxy-benzyl)-((1R,2S,5S)-2-phenyl-3-aza-bicyclo[3.1.0]hex-1-yl)-amine;

(6-Methoxy-1-methyl-1-trifluoromethyl-isochroman-7-ylmethyl)-((1R,2S,5S)-2-phenyl-3-aza-bicyclo[3.1.0]hex-1-yl)-amine;

(1R,2S,5S)-1-Methylamino-2-phenyl-3-aza-bicyclo[3.1.0]hexane-3-carboxylic acid [1-((R)-3,5-bis-trifluoromethyl-phenyl)-ethyl]-methyl-amide trifluroacetic acid salt;

(1S,2S,5R)-1-Methylamino-2-phenyl-3-aza-bicyclo[3.1.0]hexane-3-carboxylic acid [1-((R)-3,5-bis-trifluoromethyl-phenyl)-ethyl]-methyl-amide;

(1S,2R,5R)-1-Methylamino-2-phenyl-3-aza-bicyclo[3.1.0]hexane-3-carboxylic acid [1-((S)-3,5-bis-trifluoromethyl-phenyl)-ethyl]-methyl-amide trifluro acetic acid;

(1R,2S,5S)-1-Methylamino-2-phenyl-3-aza-bicyclo[3.1.0]hexane-3-carboxylic acid [1-((S)-3,5-bis-trifluoromethyl-phenyl)-ethyl]-methyl-amide trifluro acetic acid salt;

(1R,2S,5S)-1-{[((1S,7bR)-6-Methoxy-3-methyl-2-oxo-1a,2,3,7b-tetrahydro-1H-3-aza-cyclopropa[a]naphthalen-5-ylmethyl)-amino]-methyl}-2-phenyl-3-aza-bicyclo[3.1.0]hexane-3-carboxylic acid tert-butyl ester;

(6-Methoxy-1-methyl-1-trifluoromethyl-isochroman-7-ylmethyl)-((1R,2S)-2-phenyl-3-aza-bicyclo[3.1.0]hex-1-ylmethyl)-amine;

(1S,2S)-1-(3,5-Bis-trifluoromethyl-benzyloxymethyl)-2-phenyl-3-aza-bicyclo[3.1.0]hexane;

5-[(1S,2S)-1-(3,5-Bis-trifluoromethyl-benzyloxymethyl)-2-phenyl-3-aza-bicyclo[3.1.0]hex-3-ylmethyl]-2,4-dihydro-[1,2,4]triazol-3-one;

{5-[(1S,2S)-1-(3,5-Bis-trifluoromethyl-benzyloxymethyl)-2-phenyl-3-aza-bicyclo[3.1.0]hex-3-ylmethyl]-1H-[1,2,3]triazol-4-ylmethyl}-dimethyl-amine;

(1S,2S)-1-(3,5-Bis-trifluoromethyl-benzyloxymethyl)-2-phenyl-3-aza-bicyclo[3.1.0]hexane-3-carboxylic acid [(S)-1-(3,5-bis-trifluoromethyl-phenyl)-ethyl]-methyl-amide;

(1R,2S)-1-(3,5-Bis-trifluoromethyl-benzyloxy)-2-phenyl-3-aza-bicyclo[3.1.0]hexane;

(1S,2S)-1-(3,5-Bis-trifluoromethyl-benzyloxy)-2-phenyl-3-aza-bicyclo[3.1.0]hexane;

5-[(1R,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one;

5-[(1S,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one;

{5-[(1R,2S)-1-(3,5-Bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

{5-[(1S,2S)-1-(3,5-Bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

(1S,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide;

(1R,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide;

[(S)-1-(3,5-Bis-trifluoromethyl-phenyl)-ethyl]-methyl-carbamic acid (1R,2S)-2-phenyl-3-aza-bicyclo[3.1.0]hex-1-yl ester;

(1S,2S)-1-Hydroxymethyl-2-phenyl-3-aza-bicyclo[3.1.0]hexane-3-carboxylic acid [(R)-1-(3,5-bis-trifluoromethyl-phenyl)-ethyl]-methyl-amide;

(1R,2S)-1-methylaminomethyl-2-phenyl-3-aza-bicyclo[3.1.0]hexane-3-carboxylic acid [(R)-1-(3,5-bis-trifluoromethyl-phenyl)-ethyl]-methyl-amide;

(1R,2S)-1-Aminomethyl-2-phenyl-3-aza-bicyclo[3.1.0]hexane-3-carboxylic acid [(R)-1-(3,5-bis-trifluoromethyl-phenyl)-ethyl]-methyl-amide;

(1R,2R)-3-Benzyl-2-phenyl-3-aza-bicyclo[3.1.0]hexane-1-carboxylic acid [(S)-1-(3,5-bis-trifluoromethyl-phenyl)-ethyl]-methyl-amide;

(1S,2S)-2-Phenyl-3-aza-bicyclo[3.1.0]hexane-1-carboxylic acid [(S)-1-(3,5-bis-trifluoromethyl-phenyl)-ethyl]-methyl-amide;

(1S,2S)-1-methylamino-2-phenyl-3-aza-bicyclo[3.1.0]hexane-3-carboxylic acid [(S)-1-(3,5-bis-trifluoromethyl-phenyl)-ethyl]-methyl-amide;

(1S,2S)-1-Amino-2-phenyl-3-aza-bicyclo[3.1.0]hexane-3-carboxylic acid [(S)-1-(3,5-bis-trifluoromethyl-phenyl)-ethyl]-methyl-amide;

(2-Methoxy-5-trifluoromethoxy-benzyl)-((1S,2S)-2-phenyl-3-aza-bicyclo[3.1.0]hex-1-yl)-amine;

and pharmaceutically acceptable salts or solvates thereof.

Compounds of Formula I can contain chiral centers and therefore can exist in different enantiomeric and diastereomeric forms. This invention relates to all optical isomers and all stereoisomers of compounds of Formula I, including racemic mixtures and as individual enantiomers and diastereoismers, and mixtures thereof, and to all pharmaceutical compositions and methods of treatment defined above that contain or employ them, respectively. Individual isomers can be obtained by known methods, such as optical resolution, optically selective reaction, or chromatographic separation in the preparation of the final product or its intermediate.

Other more specific methods of this invention include the above methods wherein the compound of Formula I is administered to a human for the treatment of major depressive disorder and concomitant generalized anxiety disorder.

Other more specific methods of this invention include the above methods wherein the compound of Formula I is administered to a human for the treatment of major depressive disorder and concomitant irritable bowel syndrome.

Other more specific methods of this invention include the above methods wherein the compound of Formula I is administered to a human for the treatment of major depressive disorder and concomitant functional abdominal pain.

Other more specific methods of this invention include the above methods wherein the compound of Formula I is administered to a human for the treatment of major depressive disorder and concomitant neuropathic pain.

Other more specific methods of this invention include the above methods wherein the compound of Formula I is administered to a human for the treatment of major depressive disorder and concomitant premenstrual dysphoric disorder.

Other more specific methods of this invention include the above methods wherein the compound of Formula I is administered to a human for the treatment of major depressive disorder and concomitant dysthymia.

Other more specific methods of this invention include the above methods wherein the compound of Formula I is administered to a human for the treatment of major depressive disorder and concomitant fibromyalgia.

Other more specific methods of this invention include the above methods wherein the compound of Formula I is administered to a human for the treatment of major depressive disorder and a concomitant somatoform disorder such as somatization disorder, conversion disorder, body dysmorphic disorder, hypochondriasis, somatoform pain disorder or undifferentiated somatoform disorder.

Other more specific methods of this invention include the above methods wherein the compound of Formula I is administered to a human for the treatment of generalized anxiety disorder and concomitant irritable bowel syndrome.

Other more specific methods of this invention include the above methods wherein the compound of Formula I is administered to a human for the treatment of generalized anxiety disorder and concomitant functional abdominal pain.

Other more specific methods of this invention include the above methods wherein the compound of Formula I is administered to a human for the treatment of generalized anxiety disorder and concomitant neuropathic pain.

Other more specific methods of this invention include the above methods wherein the compound of Formula I is administered to a human for the treatment of generalized anxiety disorder and concomitant premenstrual dysphoric disorder.

Other more specific methods of this invention include the above methods wherein the compound of Formula I is administered to a human for the treatment of generalized anxiety disorder and concomitant dysthymia.

Other more specific methods of this invention include the above methods wherein the compound of Formula I is administered to a human for the treatment of generalized anxiety disorder and concomitant fibromyalgia.

Other more specific methods of this invention include the above methods wherein the compound of Formula I is administered to a human for the treatment of generalized anxiety disorder and a concomitant somatoform disorder selected from the group consisting of somitization disorder, conversion disorder, hypochondriasis, somatoform pain disorder (or simply "pain disorder"), body dysmorphic disorder, undifferentiated somatoform disorder, and somatoform disorder not otherwise specified. See Diagnostic and Statistical manual of Mental Disortders, Fourth Edition (DSM-IV), American Psychiatric Association, Washington, D.C., Can 1194, pp. 435-436.

Other more specific methods of this invention include the above methods wherein the compound of Formula I is administered to a human for the treatment of major depressive disorder accompanied by one or more somatic symptoms such as loss of appetite, sleep disturbances (e.g., insomnia, interrupted sleep, early morning awakening, tired awakening), loss of libido, restlessness, fatigue, constipation, dyspepsia, heart palpitations, aches and pains (e.g., headache, neck pain, back pain, limb pain, joint pain, abdominal pain), dizziness, nausea, heartburn, nervousness, tremors, burning and tingling sensations, morning stiffness, abdominal symptoms (e.g., abdominal pain, abdominal distention, gurgling, diarrhea), or the symptoms associated with generalized anxiety disorder (e.g., excessive anxiety and worry (apprehensive expectation), occurring more days than not for at least six months, about a number of events and activities, difficulty controlling the worry, etc.) See Diagnostic and Statistical manual of Mental Disorders, Fourth Edition (DSM-IV), American Psychiatric Association, Washington, D.C., Can 1194, pp. 435-436 and 445-469. This document is incorporated herein by reference in its entirety.

Other more specific methods of this invention include the above methods wherein the compound of Formula I is administered to a human for the treatment of major depressive disorder accompanied by one or more somatic symptoms such fatigue, headache, neck pain, back pain, limb pain, joint pain, abdominal pain, abdominal distention, gurgling, diarrhea nervousness, or the symptoms associated with generalized anxiety disorder (e.g., excessive anxiety and worry (apprehensive expectation), occurring more days than not for at least six months, about a number of events and activities, difficulty controlling the worry, etc. See Diagnostic and Statistical manual of Mental Disorders, Fourth Edition (DSM-IV), American Psychiatric Association, Washington, D.C., Can 1194, pp. 435-436 and 445-469.

Other more specific methods of this invention include the above methods wherein the compound of Formula I is administered to a human for the treatment of generalized anxiety disorder accompanied by one or more somatic symptoms such as loss of appetite, sleep disturbances (e.g., insomnia, interrupted sleep, early morning awakening, tired awakening), loss of libido, restlessness, fatigue, constipation, dyspepsia, heart palpitations, aches and pains (e.g., headache, neck pain, back pain, limb pain, joint pain, abdominal pain), dizziness, nausea, heartburn, nervousness, tremors, burning and tingling sensations, morning stiffness, abdominal symptoms (e.g., abdominal pain, abdominal distention, gurgling, diarrhea), or the symptoms associated with major depressive disorder (e.g., sadness, tearfulness, loss of interest, ferafulness, helplessness, hopelessness, fatique, low self esteem, obsessive ruminations, suicidal thoughts, impaired memory and concentration, loss of motivation, paralysis of will, reduced appetite, increased appetite).

Other more specific methods of this invention include the above methods wherein the compound of Formula I is administered to a human for the treatment of generalized anxiety disorder accompanied by one or more somatic symptoms such as fatigue, headache, neck pain, back pain, limb pain, joint pain, abdominal pain, abdominal distention, gurgling, diarrhea nervousness, or the symptoms associated with major depressive disorder (e.g., sadness, tearfulness, loss of interest, fearfulness, helplessness, hopelessness, low self esteem, obsessive ruminations, suicidal thoughts, fatique, impaired memory and concentration, loss of motivation, paralysis of will, reduced apetite, increased appetite).

The present invention also includes isotopically labelled compounds, which are identical to those recited in Formula I compounds, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, can be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

In another practice, the compound of Formula I can be used in conjunction with one or more other therapeutic agents, e.g. different antidepressant agents such as tricyclic antidepressants (e.g. amitriptyline, dothiepin, doxepin, trimipramine, butripyline, clomipramine, desipramine, imipramine, iprindole, lofepramine, nortriptyline or protriptyline), monoamine oxidase inhibitors (e.g. isocarboxazid, phenelzine or tranylcyclopramine) or 5-HT re-uptake inhibitors (e.g. fluvoxamine, sertraline, fluoxetine or paroxetine), and/or with antiparkinsonian agents such as dopaminergic antiparkinsonian agents (e.g. levodopa, preferably in combination with a peripheral decarboxylase inhibitor e.g. benserazide or carbidopa, or with a dopamine agonist e.g., bromocriptine, lysuride or pergolide).

In a preferred practice, the compound of Formula I is used in combination with a 5-HT re-uptake inhibitor (e.g. fluvoxamine, sertraline, fluoxetine or paroxetine), preferably sertraline (or a pharmaceutically acceptable salt or polymorph thereof as would be understood by the artisan) as psychotherapeutics and can be used in the treatment or prevention of disorders the treatment or prevention of which is facilitated by modulating serotonergic neurotransmission such as hypertension, depression (e.g. depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g. small cell lung carcinoma), chronic paroxysmal hemicrania and headache (associated with vascular disorders).

Sertraline, (1S-cis)-4-(3,4-dichlorophenyl)-1,2,3,4-tetrahydro-N-methyl-1-naphthalenamine, has the chemical Formula $C_{17}H_{17}NC_{12}$; its synthesis is described in U.S. Pat. No. 4,536,518 incorporated herein by reference. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

Administration

The compound of the invention can be administered either alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed thereby can be readily administered in a variety of dosage forms such as tablets, powders, lozenges, liquid preparations, syrups, injectable solutions and the like. These pharmaceutical compositions can optionally contain additional ingredients such as flavorings, binders, excipients and the like.

Thus the compound of the invention can be Formulated for oral, buccal, intranasal, parenteral (e.g. intravenous, intramuscular or subcutaneous), transdermal (e.g. patch) or rectal administration or in a form suitable for administration by inhalation or insufflation. E.g. for oral administration, the pharmaceutical compositions can take the form of tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets can be coated by methods known in the art. Liquid preparations for oral administration can take the form of e.g. solutions, syrups or suspensions, or they can be presented as a dry product for constitution with water or other suitable vehicle before use. Such liquid preparations can be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid). For buccal administration, the composition can take the form of tablets or lozenges Formulated in conventional manner.

The compound of the invention can be Formulated for parenteral administration by injection, including using conventional catheterization techniques or infusion. Formulations for injection can be presented in unit dosage form, e.g. in ampules or in multi-dose containers, with an added preservative. They can take such forms as suspensions, solutions or emulsions in oily or aqueous vehicles, and can contain Formulating agents such as suspending, stabilizing and/or dispersing agents. Alternatively, the active ingredient can be in powder form for reconstitution with a suitable vehicle, e.g. sterile pyrogen-free water, before use.

The compound of the invention can also be Formulated in rectal compositions such as suppositories or retention enemas, e.g. containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. The pressurized container or nebulizer can contain a solution or suspension of the active compound. Capsules and cartridges (made e.g. from gelatin) for use in an inhaler or insufflator can be Formulated containing a powder mix of a compound of the invention and a suitable powder base such as lactose or starch.

A proposed dose of the active compounds of the invention for oral, parenteral or buccal administration to the average adult human for the treatment of the conditions referred to above is about 0.1 to about 200 mg of the active ingredient per unit dose which could be administered, for example, 1 to 4 times per day.

Aerosol Formulations for treatment of the conditions referred to above in the average adult human are preferably arranged so that each metered dose or "puff" of aerosol contains about 20 mg to about 1000 mg of the compound of the invention. The overall daily dose with an aerosol will be within the range of about 100 mg to about 10 mg. Administration can be once or several times daily, e.g. 2, 3, 4 or 8 times, giving for example, 1, 2 or 3 doses each time.

In connection with the use of the compound of the invention with a 5-HT re-uptake inhibitor, preferably sertraline, for the treatment of subjects possessing any of the above conditions, it is to be noted that these can be administered either alone or in combination with pharmaceutically acceptable carriers by either of the routes previously indicated, and that such administration can be carried out in both single and multiple dosages. More particularly, the active combination can be administered in a wide variety of different dosage forms, i.e. they can be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical Formulations can be suitably sweetened and/or flavored by means of various agents of the type commonly employed for such purposes. In general, the compounds of Formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e. in amounts which are sufficient to provide the desired unit dosage.

A proposed daily dose of the compound of the invention in the combination Formulation (a Formulation containing the compound of the invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of the compound of Formula I per unit dose which could be administered, for example, 1 to 4 times per day.

A proposed daily dose of a 5-HT re-uptake inhibitor, preferably sertraline, in the combination Formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination Formulation for oral, parenteral or buccal administration to the average adult human for the treatment of the conditions referred to above is from about 0.00005 to about 20000; preferably from about 0.25 to about 2000.

Aerosol combination Formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration can be once or several times daily, e.g. 2, 3, 4 or 8 times, giving for example, 1, 2 or 3 doses each time.

Aerosol Formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration can be once or several times daily, for example 2, 3, 4 or 8 times, giving for example, 1 2 or 3 each time.

As previously indicated, a 5-HT re-uptake inhibitor, preferably sertraline, in combination with compounds of Formula I is readily adapted to therapeutic use as antidepressant agents. In general, these antidepressant compositions containing a 5-HT re-uptake inhibitor, preferably sertraline, and a compound of Formula I is normally administered in dosages ranging from about 0.01 mg to about 100 mg per kg of body weight per day of a 5-HT re-uptake inhibitor, preferably sertraline, preferably from about 0.1 mg to about 10 mg per kg of body weight per day of sertraline; with from about 0.001 mg to about 100 mg per kg of body weight per day of a compound of Formula I, preferably from about 0.01 mg to about 10 mg per kg of body weight per day of a compound of Formula I, although variations will necessarily occur depending upon the conditions of the subject being treated and the particular route of administration chosen.

Additionally, it is also possible to administer the compounds of Formula I, or their pharmaceutically acceptable salts or solvates, topically and this can preferably be done by way of creams, jellies, gels, pastes, ointments and the like, in accordance with standard pharmaceutical practice.

NK1 Assays

The activity of the compounds of Formula I, or their pharmaceutically acceptable salts or solvates, as substance P antagonists (NK1) can be determined by their ability to inhibit the binding of substance P at its receptor sites in bovine caudate tissue, employing radioactive ligands to visualize the tachykinin receptors by means of autoradiography. The substance P antagonizing activity of the herein described compounds can be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol)hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The compounds of Formula I that are basic in nature are capable of forming a wide variety of different salts with various inorganic and organic acids. Although such salts must be pharmaceutically acceptable for administration to animals, it is often desirable in practice to initially isolate a compound of Formula I or from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of Formula I that are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula I. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

General Synthetic Schemes

The following schemes are representative of methods useful in synthesizing the compound of the present invention; they are not to constrain the scope of same in any way.

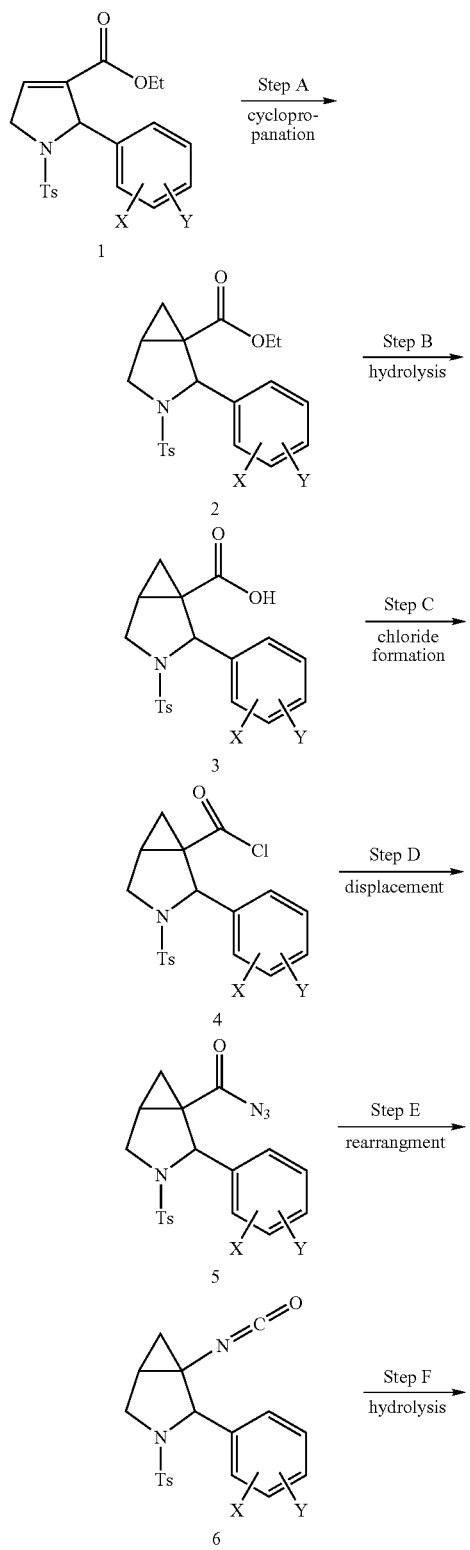

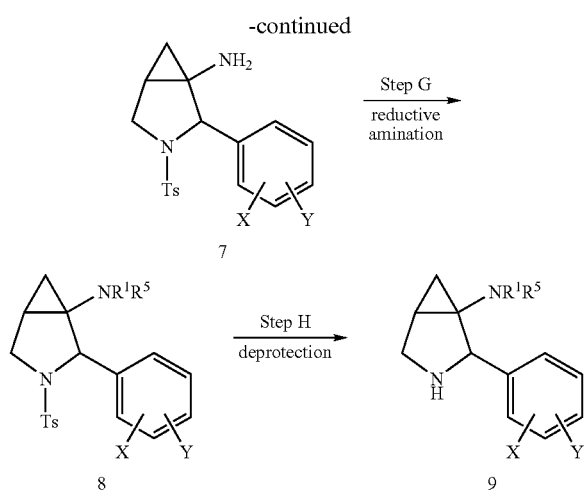

7

8

9
Formula IA

In Scheme 1, compounds of the Formula (I) are prepared as follows:

Step A

The compounds of Formula (IA) are synthesized from compound (1) which can be prepared using conditions described in J. Org. Chem. Soc. 1998, 63, 5031. Reaction of (1) with trimethylsulfoxoniumiodide in a reaction inert solvent, where THF is preferred in the presence of DMSO and a base preferable sodium hydride, or potassium hydride at reaction temperature ranging from about −78° C. to rt, where the preferred reaction temperature is from about −20° C. to rt yields the compound (2).

Step B

Compound (2) is hydrolyzed using standard conditions known in the art. The preferred method of hydrolysis is by reaction of (2) with a solution of aqueous sodium hydroxide in a protic solvent, preferably ethyl alcohol, at the reflux temperature of the solvent to yield compound (3).

Step C

Compound (3) is converted to the corresponding acid chloride using standard conditions that appear in the literature. Reaction of compound (3) with thionyl chloride in the presence of a catalytic amount of DMF in a reaction inert solvent, preferably toluene, at a reaction temperature ranging from about 0° C. to the reflux temperature of the solvent used, preferably ranging from about 0° C. to rt yields an acid chloride compound (4).

Step D

Compound (4) in a reaction inert solvent, preferably acetone, is reacted with an aqueous solution of sodium azide at a temperature ranging from about rt to about the reflux temperature of the solvent, preferably at about rt, yielding an acyl azide compound (5).

Step E

Compound (5) is heated in a reaction inert solvent preferably benzene or toluene, at a reflux temperature of the solvent employed to yield the isocyanate compound (6).

Step F

Hydrolysis of the isocyanate compound (6) can be accomplished using standard conditions found in the literature. The preferred method of hydrolysis is by reacting the isocyanate compound (6) with an inorganic acid where, aqueous HCl is preferred, in a reaction inert solvent such as THF or dioxane, at a reaction temperature ranging from about 0° C. to rt. The resulting HCl salt is free-based using aqueous sodium hydroxide to give the amine compound (7).

Step G

Reductive amination of compound (7) to give compound (8) can be accomplished by reacting compound (7) in the presence of a catalytic amount of acid, preferably acetic acid, and in the presence of a reducing reagent, preferably sodium triacetoxyborohydride, with the appropriate ketone or aldehyde at a reaction temperature of about rt to yield the amine compound (8).

Step H

Removal of the tosyl protecting group can be accomplished using known methods. A preferred method is by reaction of (8) with sodium/naphthalene in a reaction inert solvent, where dimethoxy ethane is the preferred solvent, at a reaction temperature ranging from about −78° C. to about rt, preferably at about −78° C. to give compound (9).

Exemplary compounds of Formula (I) according to the invention can be prepared by Scheme 2.

Scheme 2

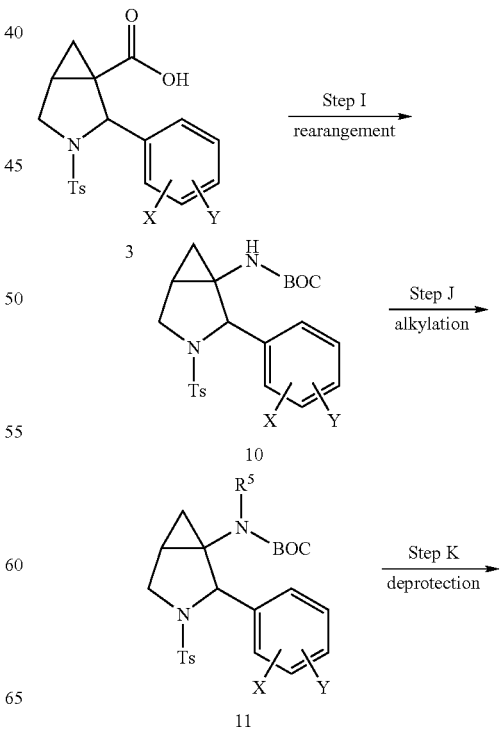

3

10

11

-continued

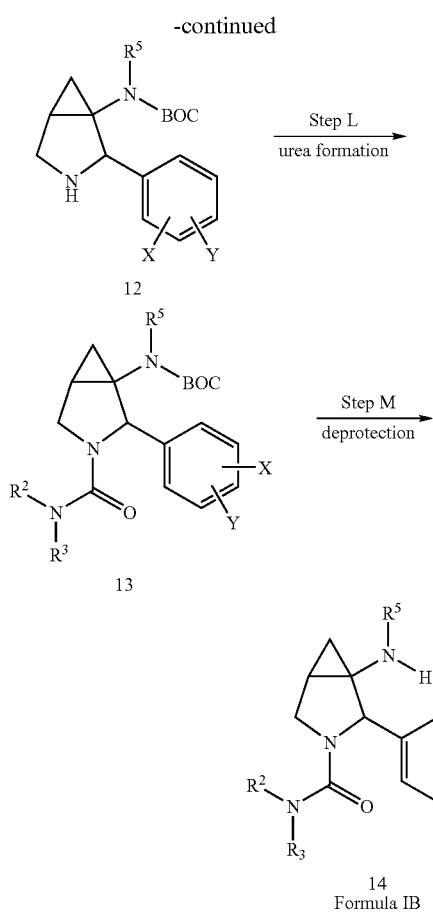

12

13

14
Formula IB

In Scheme 2, compounds of the Formula (IB) are prepared as follows.

Step I

Curtius rearrangement of compound (3) (prepared as in Scheme I above) can be accomplished using conditions known in the art. A preferred method is by reaction of compound (3) with diphenylphosphoryl azide in t-butyl alcohol in the presence of an amine base, preferably triethyl amine, at a reaction temperature ranging from about rt to about the reflux temperature of the solvent employed, preferably at about 80° C. to give the protected amine compound (10).

Step J

Reaction of compound (10) in a reaction inert solvent, preferably DMF, in the presence of an inorganic base, preferably sodium hydride, or potassium hydride, with an alkyl iodide, such as methyl iodide, ethyl iodide, n-propyl iodide or isopropyl iodide, at a reaction temperature ranging from about rt to about the reflux temperature of the solvent employed, preferably at rt, yields compound (11).

Step K

Removal of the tosyl protecting group of compound (11) can be accomplished by methods known in the art (e.g. T. W Greene; P. G. Wuts, Protective Groups in Organic Synthesis, 3$^{rd}$ edition, John Wiley & Sons Inc. New York, 1999). A preferred method of removal is by reaction of compound (11) in a protic solvent, preferable methanol, with A magnesium metal at room temperature to give compound (12). An alternative method is by reaction of compound (11) with sodium metal in ammonia at a reaction temperature of about −78° C. to give amine (12).

Step L

The coupling of an amine with compound (12) is typically performed in a reaction-inert solvent such as methylene chloride or dichloromethane, at a temperature ranging from about −78° C. to about the reflux temperature of the solvent employed, preferably at about 0 □C. to the reflux temperature of the solvent employed, more preferably at about 55° C., in the presence of a carbonyl equivalent such as phosgene, triphosgene, or carbonyldiimidazole, and in the presence of a trialkylamine base, such a triethylamine, diisopropylethylamine, to afford compound (13).

Step M

The BOC protection group of compound (13) is removed by methods known in the art (e.g. T. W Greene; P. G. Wuts, Protective Groups in Organic Synthesis, 3$^{rd}$ edition, John Wiley & Sons Inc. New York, 1999). The preferred method of BOC removal is by reaction of (13) in reaction inert solvent, preferably methylene chloride or 1,2-dichlorethane, with an acid such as hydrogen chloride, p-toluenesulfonic acid monohydrate, or TFA, preferably TFA, at a temperature ranging from about room temperature to about the reflux temperature of the solvent employed to give an amine compound (14), which is the compound of Formula (IB).

Exemplary compounds of Formula (IC) according to the invention can be prepared by Scheme 3.

Scheme 3

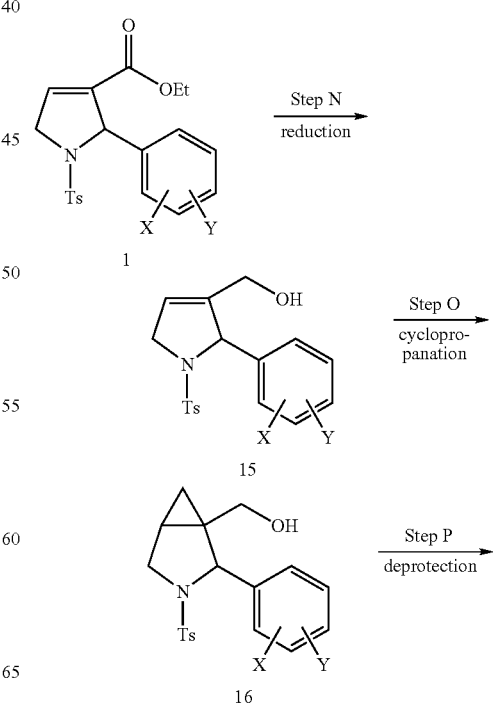

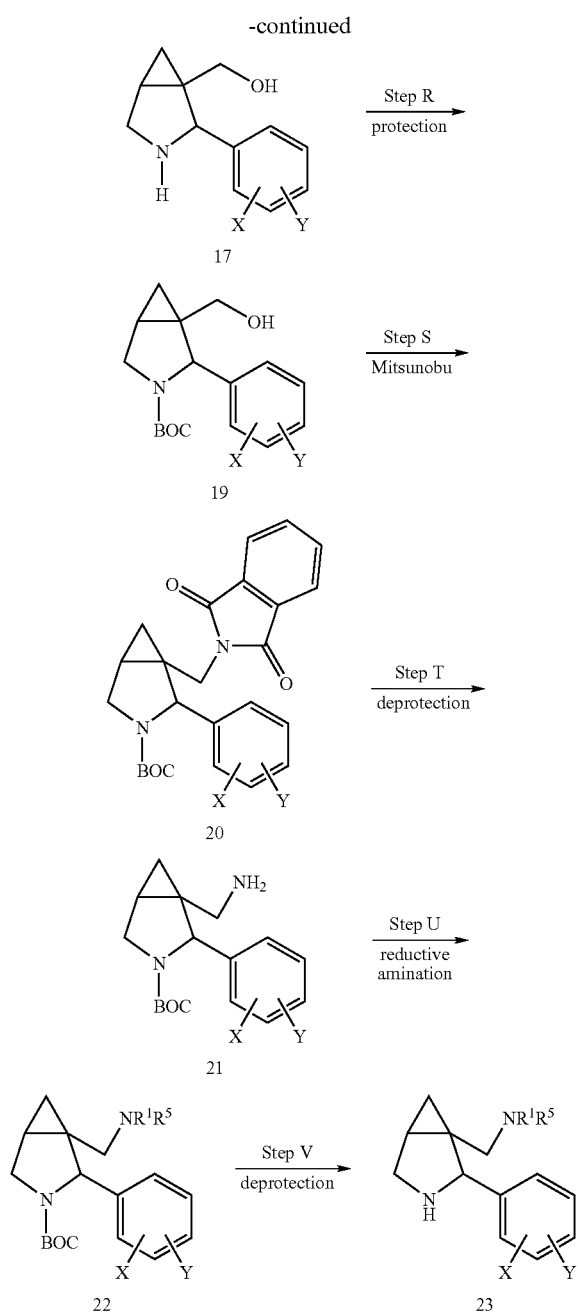

In Scheme 3, compounds of the Formula (IC) are prepared as follows:

Step N

Compound (1) (prepared as in Scheme 1 above) is reduced with an appropiate reducing reagent such as lithium aluminum hydride, sodium borohydride or aluminum trichloride, in diglyme, or diisobutyl aluminum hydride. The reaction typically takes place in an aprotic solvent, such as tetrahydrofuran or diethyl ether, at a reaction temperature ranging from about about 0° C. to the reflux temperature of the solvent employed, yielding an alcohol compound (15).

Step O

Reaction of compound (15) with trimethylsulfoxoniumiodide in a reaction inert solvent, where THF is preferred in the presence of DMSO and a base preferable sodium hydride, or potassium hydride at reaction temperature from about −78° C. to rt, where the preferred reaction temperature is from about −20 to rt yields cyclopropane (16).

Step P

Removal of a tosyl protecting group can be accomplished by methods known in the art (e.g. T. W Greene; P. G. Wuts, Protective Groups in Organic Synthesis, $3^{rd}$ edition, John Wiley & Sons Inc. New York, 1999). A preferred method of removing tosylate is by reacting compound (16) in a protic solvent, preferable methanol with magnesium metal at room temperature, to give compound (17). An alternative method is by reacting compound (16) with sodium metal in ammonia at a reaction temperature of about −78° C. to give an amine compound (17). Yet another alternative is reacting compound (16) in an inert solvent, preferably DME, with sodium/naphthalene to give compound (17).

Step R

Protection of compound (17) can be accomplished by methods known in the art (e.g. T. W Greene; P. G. Wuts, Protective Groups in Organic Synthesis, $3^{rd}$ edition, John Wiley & Sons Inc. New York, 1999). Preferably, compound (17) is reacted with di-tert-butyl dicarbonate in the presence of an amine base, preferably triethylamine, in a reaction inert solvent, preferably dichloromethane or 1,2-dichloroethane, at a reaction temperature ranging from about 0° C. to about rt to give compound (19).

Step S

Displacement of compound (19) can be accomplished under Mitsunobu conditions. Reaction of compound (19) in an inert reaction solvent, preferably tetrahydrofuran, with phthalimide in the presence of an activation reagent, preferably diethylazodicarboxylate, in the presence of triphenylphosphine at a reaction temperature ranging from about rt to about the reflux temperature of the solvent employed gives compound (20).

Step T

Selective removal of the phthalimide protecting group from compound (20) can be accomplished by methods known in the art (e.g. T. W Greene; P. G. Wuts, Protective Groups in Organic Synthesis, $3^{rd}$ edition, John Wiley & Sons Inc. New York, 1999). A preferred method of removal is by reacting compound (20) in a ($C_1$-$C_6$) alcohol solvent, preferably ethanol, with aqueous hydrazine, at a reaction temperature ranging from about rt to about the reflux temperature of the solvent employed, preferably at the reflux temperature of the solvent employed, to give the primary amine compound (21).

Step U

Reductive amination of compound (21) is accomplished by reacting compound (21) in a reaction inert solvent such as methylene chloride, dichloroethane, tetrahydrofuran, preferably methylene chloride, in the presence of an appropriate aldehyde or ketone, and in the presence of Na(OAc)$_3$BH at room temperature to give compound (22). An alternative procedure is to pre-form an imine prior to the addition of methanol and Na(OAc)$_3$BH.

Step V

Removal of the BOC protecting group from compound (22) can be accomplished using conditions described in the literature. A preferred method of protecting group removal is by reacting compound (22) in a reaction inert solvent, preferably methylene chloride, with an acid, preferably TFA, or aqueous HCl, at a reaction temperature ranging from about 0° C. to the reflux temperature of the solvent employed, preferably at about rt, to give compound (23).

Exemplary compounds of Formula (I) according to the invention can be prepared by Scheme 4.

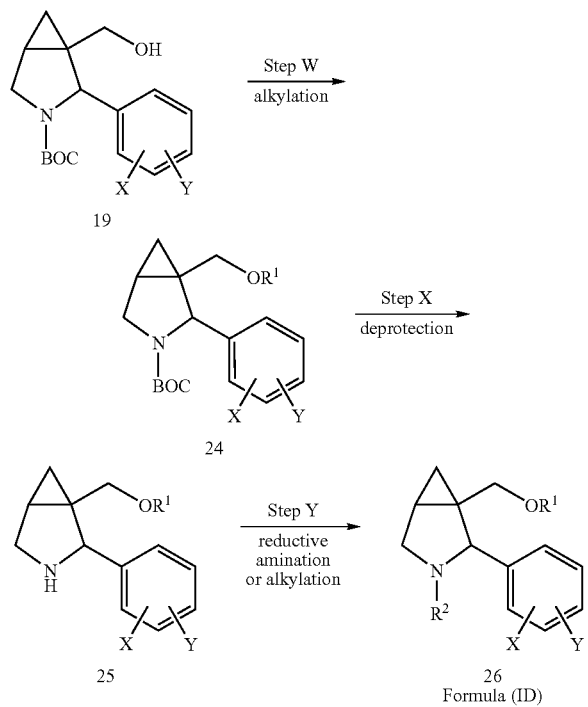

In Scheme 4, compounds of Formula (I) are prepared as follows.

Step W

The alkylation of compound (19) (prepared as in Scheme 3 above) can be accomplished by reacting compound (19) from Scheme 3 in an inert solvent such as tetrahydrofuran, with a base such as sodium hydride, potassium t-butoxide, or potassium bis(trimethylsilyl)amide, with $R^1$-halide, for example 1-idodmethyl-3,5-bis-trifluoromethyl-benzene. at a reaction temperature ranging from about −78° C. to about rt, preferably at about −78° C. to give compound (24).

Step X

Removal of the BOC protecting group from compound 24 can be accomplished using conditions described in the literature. A preferred method of protecting group removal is by reacting compound (24) in a reaction inert solvent, preferably methylene chloride, with an acid, preferably TFA or aqueous HCl, at a reaction temperature ranging from about 0° C. to about the reflux temperature of the solvent employed, preferably at about rt, to give compound (25).

Step Y

Reaction of compound (25) in DMF with an $R^2$-halide, preferably an $R^2$-chloride, $R^2$-bromide or $R^2$-iodide, at a reaction temperature ranging from about rt to about the reflux temperature of the solvent employed, gives compound (26). Alternatively, alkylation of compound (25) can be accomplished by reductive amination process. Reaction of compound (25) in a reaction inert solvent such as methylene chloride, dichloroethane, tetrahydrofuran, preferably methylene chloride, in the presence of an appropriate aldehyde or ketone, and in the presence of Na(OAc)$_3$BH at room temperature gives compound (26).

Exemplary compounds of Formula (I) according to the invention can be prepared by Scheme 5.

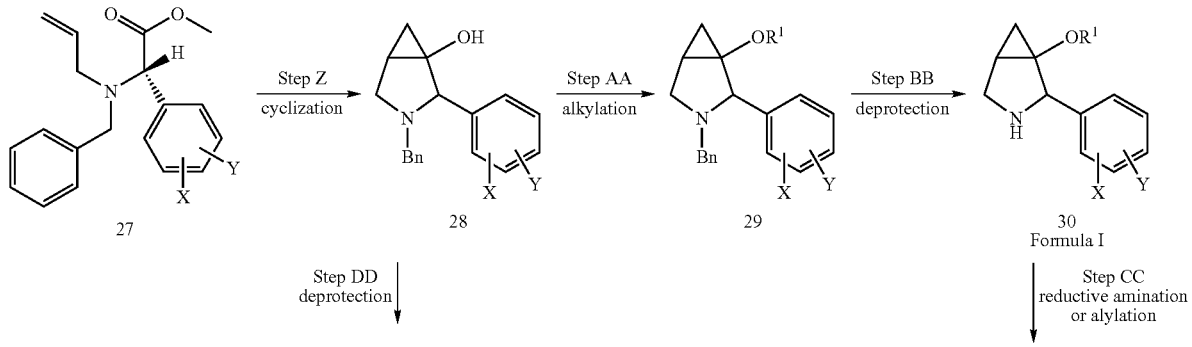

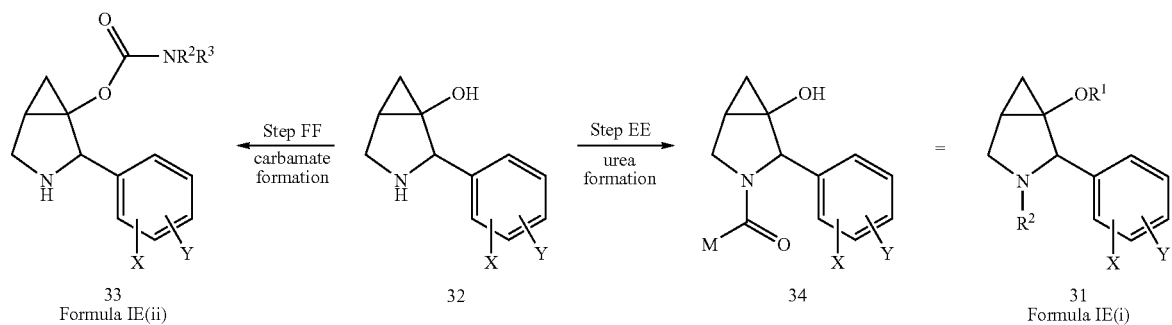

33
Formula IE(ii)

32

34

31
Formula IE(i)

In Scheme 5, compounds of the Formulae (IE)(i) and IE(ii) are prepared as follows.

Step Z

Addition of compound (27) in a reaction inert solvent, preferably tetrahydrofuran, to a solution of titanium (IV) isopropoxide in tetrahydrofuran at a reaction temperature ranging from about 0° C. to −78° C., preferably about −78° C., and in the presence of isopropylmagnesium chloride. After complete addition of compound (27), the reaction mixture is warmed to about rt to give an alcohol compound (28).

Step AA

The alkylation of compound (28) can be accomplished by reaction of compound (28) in a reaction inert solvent such as tetrahydrofuran, with a base, i.e. sodium hydride, potassium t-butoxide, or potassium bis(trimethylsilyl)amide, and with an $R^1$-halide, for example 1-bromomethyl-3,5-bis-trifluoromethyl-benzene, at a reaction temperature ranging from about −78° C. to about rt to give compound (29).

Step BB

Reaction of compound (29) in a reaction inert solvent, preferably a ($C_1$-$C_6$)alcohol solvent such as methanol or ethanol with hydrogen gas (at around 40 psi) in the presence of Pearlman's catalyst (20% palladium hydroxide on carbon), at a reaction temperature of about rt gives compound (30).

Step CC

Reaction of compound (30) in DMF with an $R^2$-halide, preferably $R^2$-chloride, $R^2$-bromide or $R^2$-iodide, at a reaction temperature ranging from about rt to about the reflux temperature of the solvent employed, gives compound (31). Alternatively, alkylation of compound (30) can be accomplished by reductive amination. Reaction of compound (30) in a reaction inert solvent such as methylene chloride, dichloroethane or tetrahydrofuran, preferably methylene chloride, in the presence of an appropriate aldehyde or ketone, and in the presence of Na(OAc)$_3$BH, at a reaction temperature of about room temperature gives compound (31).

Step DD

Reaction of compound (28) in a reaction inert solvent, preferably ($C_1$-$C_6$)-alcohol solvents such as methanol and ethanol, with hydrogen gas (at around 40 psi) in the presence of Pearlman's catalyst (20% palladium hydroxide on carbon), at a reaction temperature of about rt gives compound (32).

Step EE

The coupling of an amine, where substituted benzyl amines are preferred, with intermediate (32) is typically performed in a reaction-inert solvent such as methylene chloride or dichloromethane, at a temperature ranging from about −78° C. to about the reflux temperature of the solvent employed, preferably at about 0° C. to rt, in the presence of a carbonyl equivalent, selected from phosgene, triphosgene, or carbonyldiimidazole, and in the presence of a trialkylamine base such a triethylamine or diisopropylethylamine, affords compound (34).

Step FF

An amine, where substituted benzyl amines are preferred, is added to an inert solvent, preferably chlorinated solvents such as methylene chloride, in the presence of and amine base, preferably triethylamine, and with triphosgene at a reaction temperature ranging from about 0° C. to about rt. To this mixture is added a mixture of triethylamine and the compound (32) in acetonitrile. The reaction mixture is heated to remove methylene chloride and then refluxed at about the temperature of acetonitrile to yield the carbamate compound (33).

Exemplary compounds of Formula (IF) according to the invention can be prepared by Scheme 6.

Scheme 6

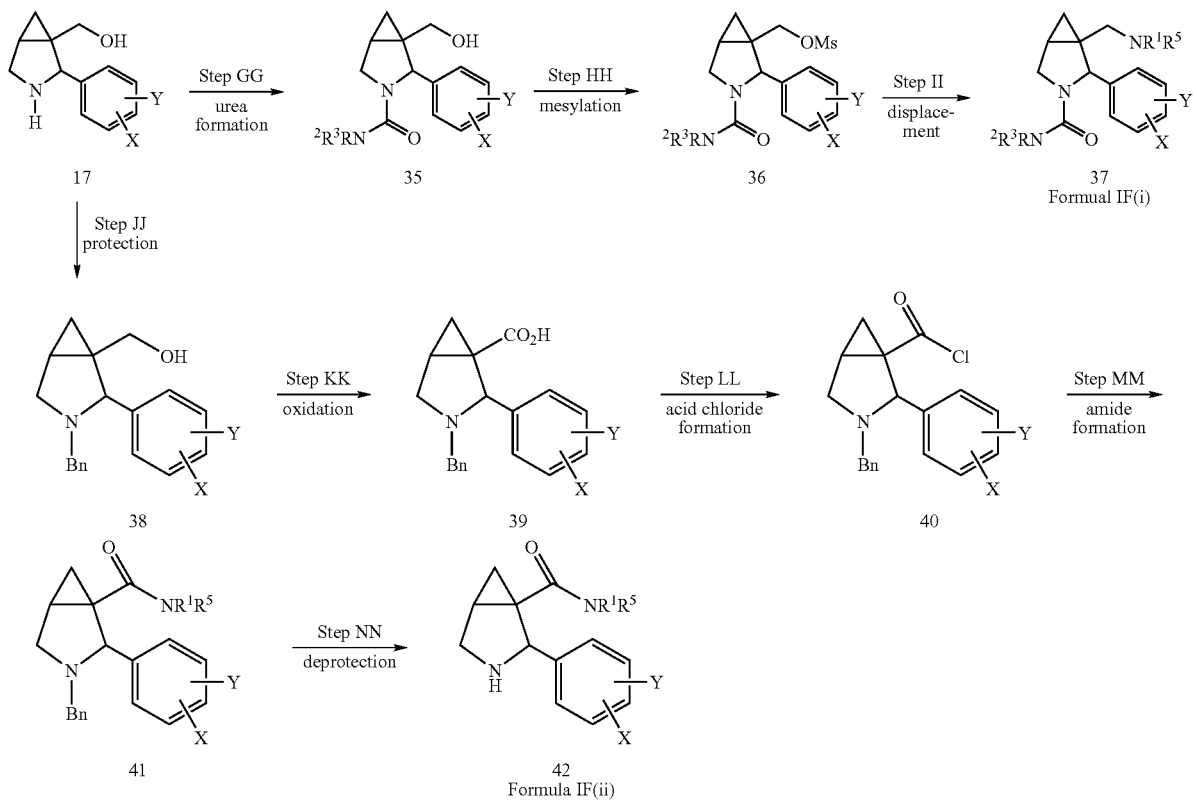

In Scheme 6, compounds of the Formulae IF(i) and IF(ii) are prepared as follows.

Step GG

The coupling of an amine (please provide list of amines), preferably a substituted benzyl amine, with compound (17) (prepared as in Scheme 3 above) is typically performed in a reaction-inert solvent such as methylene chloride or dichloromethane, at a temperature ranging from about −78° C. to about the reflux temperature of the solvent employed, preferably ranging from about 0° C. to about rt, in the presence of a carbonyl equivalent selected from phosgene, triphosgene, or carbonyldiimidazole, and in the presence of a trialkylamine base such a triethylamine or diisopropylethylamine, to afford compound (35).

Step HH

Reaction of compound (35) with a sulfonyl chloride, preferably methanesulfonyl chloride, in the presence of a base, preferably pyridine, or triethyl amine in a reaction-inert-solvent, preferably tetrahydrofuran, at a reaction temperature ranging from about 0° C. to about rt gives compound (36).

Step II

Reaction of compound (36) with an amide or an amine in a reaction-inert-solvent, preferrably dimethyl acetamide, at a reaction temperature ranging from about rt about the reflux temperature of the solvent employed, gives compound (37).

Step JJ

The protecting group for compound (17) from Scheme III can be chosen from the protective groups known in the art and described in the literature (e.g. T. W Greene; P. G. Wuts, Protective Groups in Organic Synthesis, $3^{rd}$ edition, John Wiley & Sons Inc. New York, 1999). For example, protection/alkylation of compound (17) can be accomplished by reacting of compound (17) in a ($C_1$-$C_6$) alcohol solvent, preferably methanol, with a base such as sodium bicarbonate or potassium carbonate, and with alkyl halide for example benzyl bromide at a reaction temperature at about rt to give compound (38).

Step KK

Oxidation of compound (38) can be accomplished under standard Jones oxidation conditions. The reaction of compound (38) in acetone with a solution of chromium (VI) oxide in water and sulfuric acid at a reaction temperature of about rt gives compound (39).

Step LL

Compound (39) can be converted to the corresponding acid chloride using standard conditions that appear in the literature. Reaction of compound (39) with thionyl chloride in the presence of a catalytic amount of DMF in a reaction inert solvent, preferably toluene, at a reaction temperature ranging from about 0° C. to about the reflux temperature of the solvent used, where the preferred reaction temperature ranges from about 0° C. to about rt gives the acid chloride compound (40).

Step MM

The coupling of an amine, preferably substituted benzyl amines, with compound (40) from is typically performed in a reaction-inert solvent such as methylene chloride or dichloromethane, at a temperature ranging of about room temperature in the presence of a trialkylamine base such a triethylamine or diisopropylethylamine, to afford compound (41).

Step NN

Reaction of compound (41) in a reaction inert solvent, preferably ($C_1$-$C_6$) alcohol solvents such as methanol or ethanol, with hydrogen gas (at around 40 psi) in the presence of Pearlman's catalyst (20% palladium hydroxide on carbon) at a reaction temperature of about rt gives compound (42).

Exemplary compounds of Formula (IG) according to the invention can be prepared by Scheme 7.

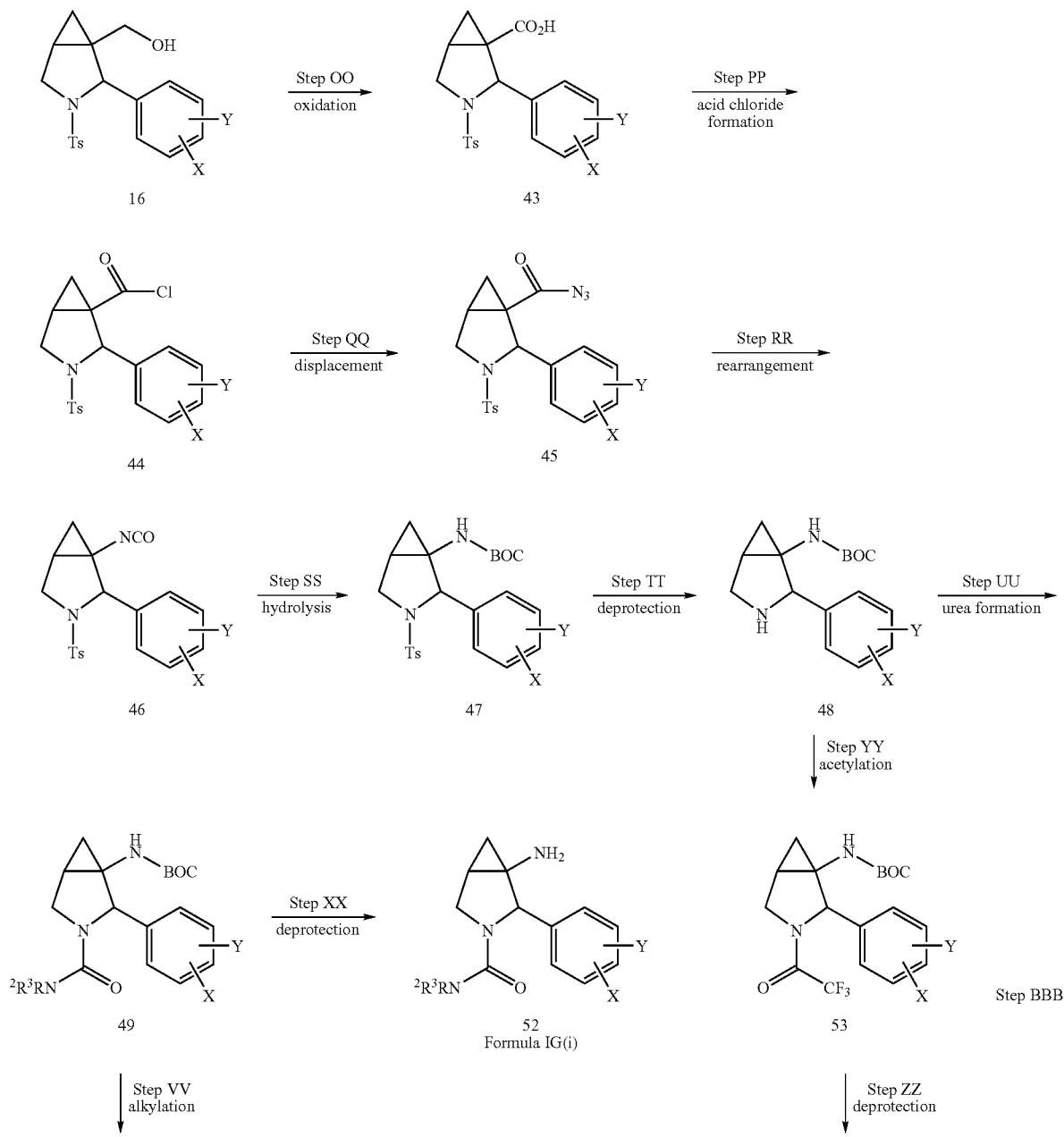

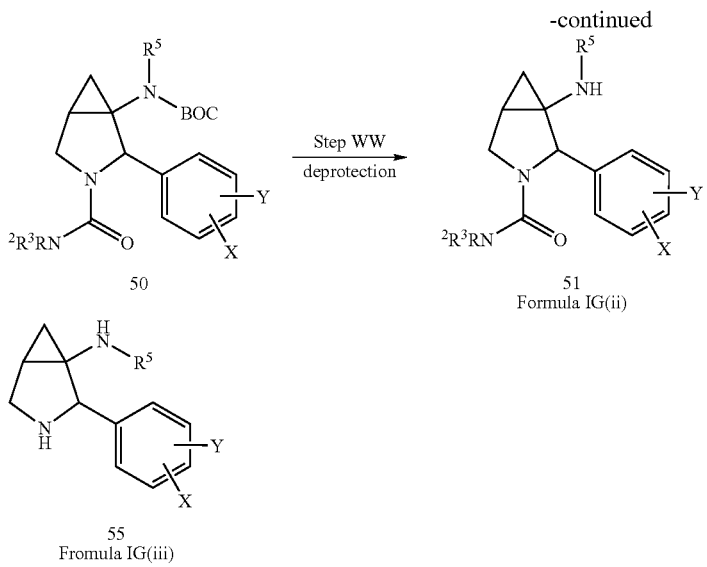

50

51
Formula IG(ii)

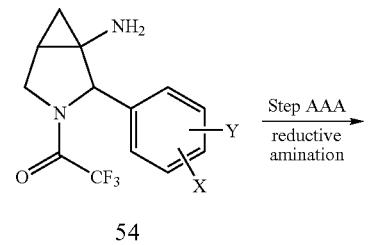

54

55
Fromula IG(iii)

In Scheme 7, compounds of the Formula (I) are prepared as follows.

Step OO

Oxidation of compound (16) (prepared as in Scheme 3 above) can be accomplished under standard Jones oxidation conditions. Reaction of compound (16) in acetone with a solution of chromium (VI) oxide in water and sulfuric acid at a reaction temperature at about rt gives compound (43).

Step PP

Compound (43) is converted to the corresponding acid chloride using standard conditions that appear in the literature. Reaction of compound (43) with thionyl chloride in the presence of a catalytic amount of DMF in a reaction inert solvent, preferably toluene, at a reaction temperature ranging from about 0° C. to about the reflux temperature of the solvent used, preferably ranging from about 0° C. to about rt gives an acid chloride compound (44).

Step QQ

Reaction of compound (44) in a reaction inert solvent, preferably acetone, with an aqueous solution of sodium azide at a temperature ranging from about rt to about the reflux temperature of the solvent employed, preferably about rt, yields an acyl azide compound (45).

Step RR

Compound (45) is heated in a reaction inert solvent, preferably benzene or toluene at around the reflux temperature of the solvent employed, to yield an isocyanate compound (46).

Step SS

Hydrolysis of compound (46) can be accomplished using standard conditions found in the literature (J. Org. Chem. 61, 1996, 2423). A preferred method of hydrolysis is by reacting compound (46) in tert-butyl alcohol with chlorotrimethylsilane in a reaction inert solvent, preferably methylene chloride, at a reaction temperature ranging from about 0° C. to about room temperature to give compound (47).

Step TT

Removal of the tosyl protecting group from compound 47 can be accomplished by methods known in the art. A preferred method is by reacting compound (47) with sodium metal in the presence of liquid ammonium in a reaction inert solvent, preferably tetrahydrofuran, at a temperature ranging from about −78° C. to give compound (48).

Step UU

The coupling of an amine, where substituted benzyl amines are preferred, with compound (48) is typically performed in a reaction-inert solvent such as methylene chloride or dichloromethane at a temperature ranging from about −78° C. to about the reflux temperature of the solvent employed, preferably at about 0° C. to rt, in the presence of a carbonyl equivalent selected from phosgene, triphosgene, or carbonyldiimidazole, and in the presence of a trialkylamine base such a triethylamine or diisopropylethylamine to afford compound (49).

Step VV

Reaction of compound (49) with an $R^5$-halide, preferably $R^5$-bromide or $R^5$-iodide such as methyl iodide, in the presence of a base, preferably sodium hydride or potassium hydride, in a reaction inert solvent, preferably DMF, at a reaction temperature ranging from about 0° C. to about the reflux temperature of the solvent employed gives compound (50).

Step WW

Removal of the BOC protecting group can be accomplished using conditions described in the literature (Please provide reference). The preferred method of protecting group removal is by reacting compound (50) in an inert solvent, preferably methylene chloride, with an acid preferably TFA or aqueous HCl, at a reaction temperature ranging from about 0° C. to about the reflux temperature of the solvent employed, preferably at about rt, to give compound (51).

Step XX

Removal of the BOC protecting group can be accomplished using conditions described in the literature. The preferred method of protecting group removal is by reaction of compound (49) in a reaction inert solvent, where methylene chloride is preferred with an acid where preferred acids are TFA, and aqueous HCl at a reaction temperature ranging from about 0° C. to about the reflux temperature of the solvent employed, where about rt is preferred to give compound (52).

Step YY

Protection of compound (48) can be accomplished by methods known in the art (e.g. T. W Greene; P. G. Wuts, Protective Groups in Organic Synthesis, $3^{rd}$ edition, John Wiley&Sons Inc. New York, 1999). Preferably, the protection of compound (48) can be accomplished by reacting compound (48) with trifluoroacetic acid in the presence of a tertiary amine base such as triethylamine or diisopropyl ethyl amine, in a reaction inert solvent, preferably chlorinated solvents such as methylene chloride, at a reaction temperature ranging from about 0° C. to about room temperature to give compound (53).

Step ZZ

Removal of the BOC protecting group can be accomplished using conditions described in the literature. The preferred method of protecting group removal is by reacting compound (53) in a reaction inert solvent, preferably methylene chloride, with an acid such as TFA and aqueous HCl at a reaction temperature ranging from about 0° C. to about the reflux temperature of the solvent employed, preferably at rt, to give compound (54).

Step AAA

Alkylation of compound (54) can be accomplished by reductive amination process. Reaction of (54) in a reaction inert solvent such as methylene chloride, dichloroethane or tetrahydrofuran, preferably methylene chloride, in the presence of an appropriate aldehyde or ketone, and in the presence of $Na(OAc)_3BH$ at room temperature gives compound (55).

Alternatively, a preferred method is by reaction of compound (54) in toluene with an appropriate aldehyde or ketone in the presence of dry molecular sieves to afford the corresponding imine that is reduced with sodium borohydride in ethanol along with concomitant removal of the protecting group to give compound (55).

In the examples below the following terms are intended to have the following, general meaning:
DIPEA: diisopropylethylamine
DMF: dimethyformamide
$MgSO_4$: magnesium sulfate
DMA: dimethyl acetamide
LRMS: low resolution mass spectrometry
° C.: degrees Celsius
calcd; calculated
d; day(s); doublet (spectral)
DCE: 1,2-dichlorethane
EtOAc: ethyl acetate
g: grams
hr; hours
Hz: hertz
J: coupling constant (in NMR)
L: liter(s)
LAH: lithium aluminum hydride
MHz: megahertz
Min: minute(s)
m/z mass to charge ratio (in mass spectrometry)
(NMR): nuclear magnetic resonance
obsd: observed
PPTs: pyridinium p-toluenesulfonate:
TsO: p-toluenesulfonate
Rf: retention factor (in chromatography)
Rt: retention time (in chromatography)
rt: room temperature
s: singlet
s: second(s)
t: triplet
TFA: trifluoroacetic acid
TFAA: trifluoroacetic anhydride
THF: tetrahydrofuran
TLC: thin layer chromatography
Ts: tosyl, p-toluenesulfonyl
TsOH: p-toluenesulfonic acid Solvents were purchased and used without purification. Yields were calculated for material judged homogenous by thin layer chromatography and NMR. Thin layer chromatography was performed on Merck Kieselgel 60 F 254 plates eluting with the solvents indicated, visualized by a 254 nm UV lamp, and stained with either an aqueous $KMnO_4$ solution or an ethanolic solution of 12-molybdophosphoric acid. Flash column chromatography was performed with using either pre-packed Biotage□ or ISCO□ columns using the size indicated. Nuclear magnetic resonance (NMR) spectra were acquired on a Unity 400 or 500 at 400 MHz or 500 MHz for $^1H$, respectively, and 100 MHz or 125 MHz for $^{13}C$ NMR, respectively. Chemical shifts for proton $^1H$ NMR spectra are reported in parts per million relative to the singlet of $CDCl_3$ at 7.24 ppm. Chemical shifts for $^{13}C$ NMR spectra are reported in parts per million downfield relative to the center line of the triplet of CDCl at 77.0 ppm. Mass spectra analyses were performed on a APCI Gilson 215, micromass ZMD (50% Acetonitrile/50% water) spectrometer.

The following examples are illustrative only; they are not restrictive.

EXAMPLES

Intermediate 2—Scheme 1

Step A

2-Phenyl-3-(toluene-4-sulfonyl)-3-aza-bicyclo[3.1.0] hexane-1-carboxylic acid ethyl ester (Racemic)

Racemic 2-phenyl-1-(toluene-4-sulfonyl)-2,5-dihydro-1H-pyrrole-3-carboxylic acid methyl ester (JOC 1998, 63, 5031-5041), (10.2 g, 27.5 mmol) and trimethylsulfoxoniumiodide (Aldrich), (6.6 9, 30.2 mmol) were dissolved in DMSO (100 mL), diluted with THF (200 mL), and cooled to −20° C. Oil free sodium hydride (0.8 g, 33.0 mmol) was added portionwise over approximately 20 minutes, the reaction was allowed to warm to room temperature and stirred 16 hours. The reaction mixture was poured into approximately 500 mL cold water and extracted with EtOAc. The EtOAc was washed with water two times and the aqueous extracts were combined and extracted with EtOAc. The last EtOAc extract was washed with water two times and the organic extracts were combined and washed with brine, dried over magnesium sulfate, and concentrated to a yellow gum. The gum was diluted with 45-50 mL Et$_2$O and cooled. Scratching induced crystallization and the resultant crystals were collected by filtration to yield 2-phenyl-3-(toluene-4-sulfonyl)-3-aza-bicyclo[3.1.0]hexane-1-carboxylic acid ethyl ester (6.23 g, 58.8% yield).

Elem. Anal.calcd for $C_{21}H_{23}NO_4S$: C, 65.43; H, 6.01; N, 3.36. Found: C, 65.26; H, 6.09; N, 3.72. m.p. 123-124° C.

Intermediate 3—Scheme 1

Step B

2-Phenyl-3-(toluene-4-sulfonyl)-3-aza-bicyclo[3.1.0]hexane-1-carboxylic acid (racemic)

A solution of racemic 2-phenyl-3-(toluene-4-sulfonyl)-3-aza-bicyclo[3.1.0]hexane-1-carboxylic acid ethyl ester (Intermediate 1) in 400 mL 10% NaOH and 80 mL ethanol was refluxed for 6 hours. The solution was allowed to cool, treated with decolorizing charcoal, and filtered thru supercel. The ethanol was evaporated at reduced pressure and the residual solution was cooled in an ice bath and acidified with concentrated HCl to pH 1. The product precipitated and was granulated for one hour, then collected by filtration to give 2-phenyl-3-(toluene-4-sulfonyl)-3-aza-bicyclo[3.1.0]hexane-1-carboxylic acid as a white solid (19.38 g, quantitative).

Intermediate 4—Scheme 1

Step C

2-Phenyl-3-(toluene-4-sulfonyl)-3-aza-bicyclo[3.1.0]hexane-1-carbonyl chloride (racemic)

To a stirring solution of racemic 2-phenyl-3-(toluene-4-sulfonyl)-3-aza-bicyclo[3.1.0]hexane-1-carboxylic acid (1.5 g, 4.2 mmol) (Intermediate 2) and one drop DMF in 10 mL of toluene at 0° C. was added thionyl chloride (8.6 mL, 11.8 mmol). The reaction was allowed to warm to room temperature and then heated to 73° C. for 2.5 hours. The solvent and excess thionyl chloride were evaporated at reduced pressure to leave 2-phenyl-3-(toluene-4-sulfonyl)-3-aza-bicyclo[3.1.0]hexane-1-carbonyl chloride (1.6 g, 100% crude yield).

$R_f$=0.45 (30% EtOAc/Hex).

Intermediate 5—Scheme 1

Step D

2-Phenyl-3-(toluene-4-sulfonyl)-3-aza-bicyclo[3.1.0]hexane-1-carbonyl azide (racemic)

To a stirred solution of sodium azide (5.63 g, 86.62 mmol) in 17 mL of water was added in a dropwise fashion to a solution of racemic 2-phenyl-3-(toluene-4-sulfonyl)-3-aza-bicyclo[3.1.0]hexane-1-carbonyl chloride (5.0 g, 13.3 mmol) (Intermediate 3) in 30 mL of acetone. 3 mL of water was then added to the reaction and the reaction mixture was stirred for 16 hours. The acetone was removed at reduced pressure and the reaction diluted with both methylene chloride and brine. The organic layer was separated, dried over sodium sulfate, filtered, and concentrated under reduced pressure to give 2-phenyl-3-(toluene-4-sulfonyl)-3-aza-bicyclo[3.1.0]hexane-1-carbonyl azide (5.1 g, 100% crude yield).

$R_f$=0.42 (30% EtOAc/Hex) LRMS m/z calcd for $C_{19}H_{18}N_4O_3S$ 382, obsd LRMS (m+1) 383.

Intermediate 6—Scheme 1

Step E

1-Isocyanato-2-Phenyl-3-(toluene-4-sulfonyl)-3-aza-bicyclo[3.1.0]hexane (racemic)

A solution of racemic 2-phenyl-3-(toluene-4-sulfonyl)-3-aza-bicyclo[3.1.0]hexane-1-carbonyl azide (5.1 g, 13.3 mmol) (Intermediate 4) in 104 mL benzene was refluxed for 16 hours. The solvent was removed at reduced pressure to leave 1-isocyanato-2-phenyl-3-(toluene-4-sulfonyl)-3-aza-bicyclo[3.1.0]hexane (4.7 g, 100% crude yield).

$R_f$=0.54 (30% EtOAc/Hex). LRMS m/z calcd for $C_{19}H_{18}N_2O_3S$ 354., obsd LRMS (m+1) 355

Intermediate 7—Scheme 1

Step F

2-Phenyl-3-(toluene-4-sulfonyl)-3-aza-bicyclo[3.1.0]hex-1-ylamine (racemic)

To a solution of racemic 1-isocyanato-2-phenyl-3-(toluene-4-sulfonyl)-3-aza-bicyclo[3.1.0]hexane Intermediate 5) in 1,4-dioxane (150 mL) was added 12% HCl aqueous (75 mL) dropwise and the reaction was allowed to stir for 16 hours at room temperature. The organic solvent was removed at reduced pressure and the flask containing the reaction residue was placed in a 0° C. bath. Methylene chloride and 2N NaOH were added until the pH of the aqueous layer was from about 9 to about 11. The layers were separated and the organic layer was washed with brine, dried over sodium sulfate, filtered, and the filtrate was concentrated to a crude weight of 3.9 g. This was adsorbed onto silica and flash chromatographed on silica with a gradient of 40% EtOAc/Hexanes to EtOAc as eluant. 2-Phenyl-3-(toluene-4-sulfonyl)-3-aza-bicyclo[3.1.0]hex-1-ylamine was obtained (2.0 g, 59% yield). The material was dissolved in hot chloroform and crystallized by adding a small amount of ether to the cooling solution.

LRMS m/z calcd for $C_{18}H_{20}N_2O_2S$ 328. obsd LRMS (m+1) 329.

Intermediate 8—Scheme 1

Step G

Mixture of diastereomers, one being (1aS,2R)-6-Methoxy-3-methyl-5-{[(1R,2S,5S)-2-phenyl-3-(toluene-4-sulfonyl)-3-aza-bicyclo[3.1.0]hex-1-ylamino]-methyl}-1,1a,3,7b-tetrahydro-3-aza-cyclopropa[a]naphthalen-2-one Into a solution of (1aR,7bS)-6-methoxy-3-methyl-2-oxo-1a,2,3,7b-tetrahydro-1H-3-aza-cyclopropa[a]naphthalene-5-carbaldehyde (0.141 g, 0.61 mmol) in methylene chloride was placed racemic Intermediate 6, one enantiomer being (1R,2S,5S)-2-phenyl-3-(toluene-4-sulfonyl)-3-aza-bicyclo[3.1.0]hex-1-ylamine (0.2 g, 0.6 mmol). The mixture was stirred for 2.0 hours. APCI mass spec showed complete imine formation (m+1: 542). Glacial acetic acid (0.038 mL, 0.7 mmol) and sodium triacetoxyborohydride (0.14 g, 0.67 mmol) was added and the reaction was allowed to stir for 16 hours. Saturated sodium bicarbonate solution was added and the phases were separated, the organic layer was washed with brine, dried over sodium sulfate, and adsorbed onto silica. Flash chromatography using a solvent gradient of 50% EtOAc/Hexanes to 7% MeOH/EtOAc gave the title compound as a colorless oil (0.19 g, 57%).

$R_f$=0.21 (30% EtOAc/Hex). LRMS m/z calcd for $C_{26}H_{28}N_2O_3S$ 448. obsd LRMS (m+1) 449.

Example 1—Scheme 1

Step H

Mixture of diastereomers, one being (1aS,2R)-6-methoxy-3-methyl-5-[((1R,2S,5S)-2-phenyl-3-aza-bicyclo[3.1.0]hex-1-ylamino)-methyl]-1,1a,3,7b-tetrahydro-3-aza-cyclopropa[a]naphthalen-2-one In a round bottomed flask were combined Intermediate 7, a mixture of diastereomers, one being one being (1aS,2R)-6-methoxy-3-methyl-5-{[(1R,2S,5S)-2-phenyl-3-(toluene-4-sulfonyl)-3-aza-bicyclo[3.1.0]hex-1-ylamino]-methyl}-1,1a,3,7b-tetrahydro-3-aza-cyclopropa[a]naphthalen-2-one (0.09 g, 0.17 mmol), methanol (5 mL), sodium hydrogen phosphate dibasic (0.24 g, 1.7 mmol), and sodium-mercury amalgam (5% sodium, 1.3 g). The mixture was refluxed under nitrogen for 15 minutes. The reaction was allowed to cool and the solvent was decanted and evaporated. The residue was partitioned between saturated sodium bicarbonate solution and methylene chloride, the organics were washed with brine, dried over sodium sulfate and flash chromatographed on silica gel using 10% Methanol/0.3% NH$_4$OH/ETOAc to give the title compound as an oil (0.032 g, 49%).

$R_f$=0.30 (15% MeOH/EtOAc w/0.2% NH$_4$OH). LRMS m/z Calcd for $C_{24}H_{27}N_3O_2$; 389. obsd LRMS (M+1)390.

Example 2

Scheme 1

Racemic mixture, one enatiomer being (5-tert-butyl-2-methoxy-benzyl)-((1R,2S,5S)-2-phenyl-3-aza-bicyclo[3.1.0]hex-1-yl)-amine Prepared as described for Example 1, Step H.

Rf=0.37 (5% MeOH/EtOAc w/0.2% NH$_4$OH); LRMS m/z Calcd for $C_{23}H_{30}N_2O$; 350. obsd LRMS (M+1)351.

Example 2—Scheme 1

Mixture of four isomers, one being (6-methoxy-1-methyl-1-trifluoromethyl-isochroman-7-ylmethyl)-((1R,2S,5S)-2-phenyl-3-aza-bicyclo[3.1.0]hex-1-yl)-amine Prepared as described in Example 1, Step H.

Rf=0.22 (5% MeOH/EtOAc w/0.2% NH$_4$OH); LRMS m/z Calcd for $C_{24}H_{27}F_3N_2O_2$; 432. obsd LRMS (M+1)433.

Intermediate 10—Scheme 2

Step I

[2-Phenyl-3-(toluene-4-sulfonyl)-3-aza-bicyclo[3.1.0]hex-1-yl]-carbamic acid tert-butyl ester (racemic)

In a round bottomed flask were combined the starting material racemic 2-phenyl-3-(toluene-4-sulfonyl)-3-aza-bicyclo[3.1.0]hexane-1-carboxylic acid (0.36 g, 1.0 mmol) and tert-butyl alcohol (5 mL). Triethylamine (0.28 mL, 2.0 mmol) and diphenylphosphoryl azide (0.3 mL, 1.4 mmol) were added and the reaction was placed in an 83° C. oil bath and allowed to reflux gently under nitrogen for 16 hours. Most of the tert-butyl alcohol was removed at reduced pressure and the residue was partitioned between saturated sodium bicarbonate solution and EtOAc. The organics were washed with brine, dried over calcium sulfate, filtered and concentrated to an oil which was flash chromatographed on silica gel using 10%-20% ETOAc/Hexanes to give [2-phenyl-3-(toluene-4-sulfonyl)-3-aza-bicyclo[3.1.0]hex-1-yl]-carbamic acid tert-butyl ester (0.14 g, 34%).

Rf=0.5 (50% EtOAc/Hex); LRMS m/z Calcd for $C_{23}H_{28}N_2O_4S$; 428. obsd LRMS (M+1) 429.

Intermediate 11—Scheme 2

Step J

Methyl-[2-phenyl-3-(toluene-4-sulfonyl)-3-aza-bicyclo[3.1.0]hex-1-yl]-carbamic acid tert-butyl ester (racemic)

The starting material, racemic [2-phenyl-3-(toluene-4-sulfonyl)-3-aza-bicyclo[3.1.0]hex-1-yl]-carbamic acid tert-butyl ester (Intermediate 8) (0.6 g, 1.4 mmol) was slurried in DMF (5 mL) and the mixture was cooled to 0° C. Sodium hydride (oil free, 0.05 g, 2.1 mmol) was added in portions and the reaction was then stirred for 0.75 hours at room temperature. Methyl iodide (0.13 mL, 2.1 mmol) was added and the reaction stirred an additional hour at room temperature. The mixture was partitioned between 1N lithium chloride solution and EtOAc. The organics were washed with brine and dried over calcium sulfate, filtered and concentrated to give methyl-[2-phenyl-3-(toluene-4-sulfonyl)-3-aza-bicyclo[3.1.0]hex-1-yl]-carbamic acid tert-butyl ester as a yellow crystalline solid (0.654 g, 105%) which contained approximately 0.33 mol % of DMF by $^1$HNMR.

Rf=0.2 (25% EtOAc/Hex); LRMS m/z Calcd for C24H30N2O4S; 442. obsd LRMS (M+1) 443.

Intermediate 12—Scheme 2

Step K

Methyl-((1R,2S,5S)-2-phenyl-3-aza-bicyclo[3.1.0]hex-1-yl)-carbamic acid tert-butyl ester (racemeic)

To a flame dried 125 mL rbf equipped with a dry ice condenser was added fresh sodium metal (0.32 g, 14.0 mmol). The flask was immersed in a −78° C. bath and ammonia gas was condensed into the flask until it was about a third full. Racemic Intermediate 11, one enantiomer being methyl-[(1R,2S,5S)-2-phenyl-3-(toluene-4-sulfonyl)-3-aza-bicyclo[3.1.0]hex-1-yl]-carbamic acid tert-butyl ester (0.62 g, 1.4 mmol) in THF (10 mL) was added to the flask in a thin constant stream and the mixture was stirred for 10 minutes until the reaction was complete. Solid ammonium chloride was added and the reaction was warmed to room temperature. The volatile solvents were allowed to evaporate and the residue was partitioned between 1N NaOH and methylene chloride. The organics were washed with brine, dried over sodium sulfate, filtered, and concentrated to give the title compound as an oil (0.40 g, quantitative yield).

To a flame dried 125 mL rbf equipped with a dry ice condenser was added fresh sodium metal (0.32 g, 14.0 mmol). The flask was immersed in a −78° C. bath and ammonia gas was condensed into the flask until it was about a third full. The starting material methyl-[2-phenyl-3-(toluene-4-sulfonyl)-3-aza-bicyclo[3.1.0]hex-1-yl]-carbamic acid tert-butyl ester (Intermediate 9) (0.62 g, 1.40 mmol) in THF (10 mL) was added to the flask in a thin constant stream and the mixture was stirred for 10 minutes at which point tlc indicated the reaction was complete. Solid ammonium chloride was added cautiously and the reaction warmed to room temperature. The volatile solvents were allowed to evaporate and the residue was partitioned between 1N NaOH and methylene chloride. The organics were washed with brine, dried over sodium sulfate, filtered, and concentrated to give methyl-(2-phenyl-3-aza-bicyclo[3.1.0]hex-1-yl)-carbamic acid tert-butyl ester as an oil (0.40 g, quantitative yield).

LRMS m/z Calcd for C17H24N2O2; 288. obsd LRMS (M+1) 289.

Intermediate 13—Scheme 2

Step L

Diastereomers one being ((1R,2S,5S)-3-{[1-((S)-3,5-Bis-trifluoromethyl-phenyl)-ethyl]-methyl-carbamoyl}-2-phenyl-3-aza-bicyclo[3.1.0]hex-1-yl)-methyl-carbamic acid tert-butyl ester and the other being ((1S,2R,5R)-3-{[1-((S)-3,5-Bis-trifluoromethyl-phenyl)-ethyl]-methyl-carbamoyl}-2-phenyl-3-aza-bicyclo[3.1.0]hex-1-yl)-methyl-carbamic acid tert-butyl ester.

To a round bottom flask was added methylene chloride (7 mL), triethylamine (0.32 mL, 2.3 mmol), and [1-(R-3,5-bis-trifluoromethyl-phenyl)-ethyl]-methyl-amine (0.21 g, 0.78 mmol). The mixture was cooled to 0° C. and triphosgene (0.087 g, 0.29 mmol) in methylene chloride (3 mL) was added dropwise. The clear solution was stirred for 4 hours at room temperature. To the reaction mixture was added racemic Intermediate 12, one enantiomer being methyl-((1R,2S,5S)-2-phenyl-3-aza-bicyclo[3.1.0]hex-1-yl)-carbamic acid tert-butyl ester (0.21 g, 0.78 mmol), diisopropyl ethyl amine (0.21 mL, 1.2 mmol), and acetonitrile (9 mL). The reaction was heated to remove the methylene chloride and then refluxed for 1 hour. The solvent was removed at reduced pressure and the residue was partitioned between saturated citric acid solution and methylene chloride, the organic phase was washed with saturated sodium bicarbonate solution, brine, dried over sodium sulfate, filtered, and concentrated to a quantitative yield of oil. This material was flash chromatographed using a gradient of 5 to 30% EtOAc/Hexanes to afford the less polar diastereomer of the title compound (0.086 g, 21% yield) as an oil and the more polar diastereomer of the title compound (0.057 g, 14% yield) also as an oil.

Rf=0.31 (40% EtOAc/Hex); LRMS m/z Calcd for C29H33F6N3O3; 585. obsd LRMS (M+1) 586.

Rf=0.39 (40% EtOAc/Hex); LRMS m/z Calcd for C24H30N2O4S; 585. obsd LRMS (M+1) 586.

Intermediate 13—Scheme 2

Alternative Step L

Diastereomers one being ((1R,2S,5S)-3-{[1-((S)-3,5-Bis-trifluoromethyl-phenyl)-ethyl]-methyl-carbamoyl}-2-phenyl-3-aza-bicyclo[3.1.0]hex-1-yl)-methyl-carbamic acid tert-butyl ester and the other being ((1S,2R,5R)-3-{[1-((S)-3,5-Bis-trifluoromethyl-phenyl)-ethyl]-methyl-carbamoyl}-2-phenyl-3-aza-bicyclo[3.1.0]hex-1-yl)-methyl-carbamic acid tert-butyl ester To a round bottom flask was added methylene chloride (7 mL), triethylamine (0.32 mL, 2.3 mmol), and [1-(S-3,5-Bis-trifluoromethyl-phenyl)-ethyl]-methyl-amine (0.21 g, 0.78 mmol. The mixture was cooled to 0° C. and triphosgene (0.087 g, 0.29 mmol) in methylene chloride (3 mL) was added dropwise. The clear solution was stirred for 4 hours at room temperature. To the reaction mixture was added racemeic Intermediate 12, one enantiomer being methyl-((1R,2S,5S)-2-phenyl-3-aza-bicyclo[3.1.0]hex-1-yl)-carbamic acid tert-butyl ester (0.20 g, 0.69 mmol), diisopropyl ethyl amine (0.21 mL, 1.2 mmol), and acetonitrile (9 mL). The reaction was heated to remove the methylene chloride and then refluxed for 1 hour. The solvent was removed at reduced pressure and the residue was partitioned between saturated citric acid solution and methylene chloride, the organic phase was washed with saturated sodium bicarbonate solution, brine, dried over sodium sulfate, filtered, and concentrated to a quantitative yield of oil. This material was flash chromatographed using a gradient of 5 to 30% EtOAc/Hexanes to afford the less polar diastereomer of the title compound (0.13 g, 32% yield) as an oil and the more polar diastereomer of the title compound (0.1 g, 25% yield) also as an oil.

Example 3—Scheme 2

Step M (1R,2S,5S)-1-Methylamino-2-phenyl-3-aza-bicyclo[3.1.0]hexane-3-carboxylic acid [1-((R)-3,5-bis-trifluoromethyl-phenyl)-ethyl]-methyl-amide trifluoroacetic acid salt A flask containing the starting material Intermediate 13, ((1R,2S,5S)-3-{[1-((R)-3,5-bis-trifluoromethyl-phenyl)-ethyl]-methyl-carbamoyl}-2-phenyl-3-aza-bicyclo[3.1.0]hex-1-yl)-methyl-carbamic acid tert-butyl ester (0.086 g, 0.15 mmol) and methylene chloride (6 mL) was immersed in a 0° C. bath, trifluoroacetic acid (0.226 mL, 2.93 mmol) was added, and the reaction stirred for 16 hours at room temperature. The solvent was removed at reduced pressure, the reaction was taken up in EtOH, and the solvent was removed at reduced pressure. The resulting oil was triturated with hexanes to give the title compound as the trifluoro acetic acid salt in quantitative yield).

LRMS m/z Calcd for C24H25F6N3O. 485; (free base). obsd LRMS (M+1) 486.

Intermediate 15—Scheme 3

Step N

[2-Phenyl-1-(toluene-4-sulfonyl)-2,5-dihydro-1H-pyrrol-3-yl]-methanol (racemic)

To racemic intermediate 1, one enantiomer being (S)-2-phenyl-1-(toluene-4-sulfonyl)-2,5-dihydro-1H-pyrrole-3-carboxylic acid ethyl ester (1.8 g, 5.0 mmol), was dissolved in methylene chloride (60 mL) in a three necked flask equipped with an addition funnel and an internal thermometer. The mixture was cooled to −25° C., DIBAL (1M/toluene, 12.5 mL, 12.5 mmol) was added dropwise and the reaction stirred for an additional 0.5 hours. Methanol was added to the cold solution until gas evolution ceased and the solvents were then removed at reduced pressure. The residue was partitioned between a saturated solution of Rochelle's salt and methylene chloride. The organics were washed with brine, dried over sodium sulfate, filtered, and concentrated. The crude product was chromatographed on silica gel using a gradient of 20% to 60% ETOAc/Hexanes to yield the title compound as a sticky foam (1.6 g, 98% yield).

Rf=0.31 (60% EtOAc/hexanes): LRMS m/z Calcd for $C_{18}H_{19}NO_3S$. 329; obsd LRMS m/z (M+1) 330.

Intermediate 16—Scheme 3

Step O

[2-Phenyl-3-(toluene-4-sulfonyl)-3-aza-bicyclo[3.1.0]hex-1-yl]-methanol

To a flask containing racemic Intermediate 15, one enantiomer being [(S)-2-phenyl-1-(toluene-4-sulfonyl)-2,5-dihydro-1H-pyrrol-3-yl]-methanol (19.0 g, 57.8 mmol), and methylene chloride (190 mL) at 0° C. and under nitrogen was added diethyl zinc (1.1M/toluene, 57.8 mL, 63.5 mmol) all at once via syringe. The reaction was stirred for twenty minutes and iodine (14.7 g, 57.7 mmol), another portion of diethyl zinc (1.1M/toluene, 57.7 mL, 63.5 mmol), and chloroiodomethane (8.8 mL, 121.3 mmol) were added in quick succession. The reaction was stirred at 0° C. for 3 hours at which point there was much white precipitate present. GC-MS analysis of an aliquot showed no product at this point. The nitrogen inlet was removed and replaced with a $CaSO_4$ drying tube, a third portion of diethyl zinc (1.1M/toluene, 2.0 mL, 1.8 mmol) was added, and the reaction allowed to stir at room temperature overnight. GC-MS analysis of an aliquot showed complete conversion to product. The reaction was diluted with saturated ammonium chloride solution and the phases were separated. The organics were washed with brine, dried with sodium sulfate, filtered, and concentrated to give the title compound as a thick oil (19.4 g, 98%).

Rf=0.22 (50% EtOAc/hexanes): LRMS m/z Calcd for $C_{19}H_{21}NO_3S$. 342; obsd LRMS m/z (M+1) 344.

Intermediate 17—Scheme 3

Step P

2-Phenyl-3-aza-bicyclo[3.1.0]hex-1-yl)-methanol 9 (racemic)

Racemic, one enantiomer being ((1S,2S,5S)-2-phenyl-3-aza-bicyclo[3.1.0]hex-1-yl)-methanol. To a flame dried 125 mL rbf equipped with a dry ice condenser was added fresh sodium metal (0.134 g, 5.8 mmol). The flask was immersed in a −78° C. bath and ammonia gas was condensed into the flask until it was about a third full. The starting Intermediate 16: General procedure 3: Step O, racemic, one enantiomer being [(1S,2S,5S)-2-Phenyl-3-(toluene-4-sulfonyl)-3-aza-bicyclo[3.1.0]hex-1-yl]-methanol (1.0 g, 2.9 mmol) in THF (8 mL total, the starting material is not very soluble in THF) was added to the flask and the mixture was stirred for 10 minutes at which point tlc indicated the reaction was complete. Solid ammonium chloride (2 g) was added cautiously and the reaction warmed to room temperature. The volatile solvents were allowed to evaporate and the residue was partitioned between 1N NaOH and methylene chloride, the organics were washed with brine, dried over sodium sulfate, filtered, and concentrated to give the title compound as an oil (0.53 g, 97% yield). This material was processed without further purification.

Intermediate 19—Scheme 3

Step R

1-Hydroxymethyl-2-phenyl-3-aza-bicyclo[3.1.0]hexane-3-carboxylic acid tert-butyl ester (racemic)

To racemic Intermediate 17, one enantiomer being ((1S,2S,5S)-2-phenyl-3-aza-bicyclo[3.1.0]hex-1-yl)-methanol (2.61 g, 13.8 mmol) dissolved in methylene chloride (20 mL) was added triethylamine (2.5 mL, 17.9 mmol). The solution was cooled to 0° C. and di-tert-butyl dicarbonate (1M/THF, 14.5 mL, 14.5 mmol) was added. The reaction was allowed to warm to room temperature and stirred for 16 hours. The solvent was removed at reduced pressure and the residue partitioned between saturated sodium bicarbonate solution and methylene chloride, the organics were washed with brine, dried over sodium sulfate, filtered, and concentrated to an oil. The material was purified by chromatography on silica using a biotage flash 40 system eluted with a gradient of 0 to 35% EtOAc/Hexanes to give the title compound as an oil (1.9 g, 48% yield).

Rf=0.06 (15% EtOAc/hexanes).

Intermediate 20—Scheme 3

Step S 1-(1,3-Dioxo-1,3-dihydro-isoindol-2-ylmethyl)-2-phenyl-3-aza-bicyclo[3.1.0]hexane-3-carboxylic acid tert-butyl ester (racemic)

To racemic Intermediate 19, one enantiomer being (1S,2S,5S)-1-hydroxymethyl-2-phenyl-3-aza-bicyclo[3.1.0]hexane-3-carboxylic acid tert-butyl ester (0.40 g, 1.4 mmol), was added anhydrous THF (5 mL), triphenylphosphine (0.43 g, 1.6 mmol), phthalimide (0.30 g, 2.1 mmol), and diethylazodicarboxylate (0.22 mL, 1.7 mmol). The reaction was allowed to stir at room temperature for 16 hours. The solvent was removed at reduced pressure and the residue partitioned between saturated sodium bicarbonate solution and methylene chloride, the organics were washed with brine, dried over sodium sulfate, filtered, and concentrated to an oil. The material was purified by chromatography on silica by elution with a gradient of 5 to 20% EtOAc/Hexanes to give the title compound as an white solid (0.56 g, 97% yield).

Rf=0.32 (30% EtOAc/hexanes).

Intermediate 21—Scheme 3

Step T

1-Aminomethyl-2-phenyl-3-aza-bicyclo[3.1.0]hexane-3-carboxylic acid tert-butyl ester (racemic)

To the starting material, 1-(1,3-dioxo-1,3-dihydro-isoindol-2-ylmethyl)-2-phenyl-3-aza-bicyclo[3.1.0]hexane-3-carboxylic acid tert-butyl ester (0.560 g, 1.34 mmol) (Intermediate 20) was added ethanol (10 mL) and hydrazine (35% in $H_2O$, 0.483 mL, 5.36 mmol). The reaction was heated to reflux, and although within a few minutes a solid precipitated that impeded stirring, the reaction was heated for a total of 80 minutes. The solvent was removed at reduced pressure and the residue partitioned between 1N NaOH solution and methylene chloride. The organics were washed with a saturated solution of citric acid two times and the methylene chloride discarded. The aqueous layer was basified with sodium bicarbonate and extracted with methylene chloride. The organics were washed with brine, dried over sodium sulfate, filtered, and concentrated to give 1-aminomethyl-2-phenyl-3-aza-bicyclo[3.1.0]hexane-3-carboxylic acid tert-butyl ester as an oil (0.268 g, 69% yield).

Intermediate 22—Scheme 3

Step U

Mixture of diastereomers, one being (1R,2S,5S)-1-{[((1aR,7bS)-6-methoxy-3-methyl-2-oxo-1a,2,3,7b-tetrahydro-1H-3-aza-cyclopropa[a]naphthalen-5-ylmethyl)-amino]-methyl}-2-phenyl-3-aza-bicyclo[3.1.0]hexane-3-carboxylic acid tert-butyl ester Racemic Intermediate 21, one enantiomer being (1R,2S,5S)-1-aminomethyl-2-phenyl-3-aza-bicyclo[3.1.0]hexane-3-carboxylic acid tert-butyl ester (0.055 g, 0.19 mmol) was combined with (1aR,7bS)-6-methoxy-3-methyl-2-oxo-1a,2,3,7b-tetrahydro-1H-3-aza-cyclopropa[a]naphthalene-5-carbaldehyde (0.046 g, 0.20 mmol) in methylene chloride (3 mL) and the mixture was stirred for 3.0 hours. APCI mass spec showed complete imine formation (m+1: 503). Methanol (1.0 mL) and sodium triacetoxyborohydride (0.053 g, 0.25 mmol) were added and the reaction allowed to stir for 16 hours. The solvent was removed at reduced pressure and the residue was partitioned between saturated sodium bicarbonate solution and methylene chloride, the organic layer was washed with brine, dried over sodium sulfate, filtered, and concentrated to give the title compound as a white foam (0.10 g, quantitative crude yield). This material was used without further purification.

Example 4A—Scheme 3

Step V

Mixture of diastereomers, one being (1R,2S,5S)-1-{[((1S,7bR)-6-methoxy-3-methyl-2-oxo-1a,2,3,7b-tetrahydro-1H-3-aza-cyclopropa[a]naphthalen-5-ylmethyl)-amino]-methyl}-2-phenyl-3-aza-bicyclo[3.1.0]hexane-3-carboxylic acid tert-butyl ester A flask containing racemic Intermediate 22, one enantiomer being (1R,2S,5S)-1-{[((1aR,7bS)-6-Methoxy-3-methyl-2-oxo-1a,2,3,7b-tetrahydro-1H-3-aza-cyclopropa[a]naphthalen-5-ylmethyl)-amino]-methyl}-2-phenyl-3-aza-bicyclo[3.1.0]hexane-3-carboxylic acid tert-butyl ester (0.19 mmol) and methylene chloride (4 mL) was immersed in a 0° C. bath, trifluoroacetic acid (0.35 mL, 4.5 mmol) was added, and the reaction stirred for 16 hours at room temperature. The solvent was removed at reduced pressure and the residue partitioned between saturated sodium bicarbonate solution and methylene chloride, the organics were washed with brine, dried over sodium sulfate, filtered, and concentrated to an oil. The material was purified by chromatography on silica by elution with a gradient of 50% EtOAc/Hexanes to 100% EtOAc then grading to 5% MeOH/0.2% $NH_4OH$/EtOAc to give the title compound as an oil (0.044 g, 57% yield).

Example 4B: Scheme 3

Step V

Mixture of four isomers (6-Methoxy-1-methyl-1-trifluoromethyl-isochroman-7-ylmethyl)-(-2-phenyl-3-aza-bicyclo[3.1.0]hex-1-ylmethyl)-amine Preparation as described in Example 4A, Scheme 3, using the appropriate starting materials.

Rf=0.25 (10% MeOH/EtOAC w/0.2% $NH_4OH$); LRMS m/z Calcd for C25H29F3N2O2; 446. obsd LRMS m/z (M+1) 447.

Intermediate 24—Scheme 4

Step W 1-(3,5-Bis-trifluoromethyl-benzyloxymethyl)-2-phenyl-3-aza-bicyclo[3.1.0]hexane-3-carboxylic acid tert-butyl ester (racemic)

To Intermediate 19, one enantiomer being (1S,2S)-1-hydroxymethyl-2-phenyl-3-aza-bicyclo[3.1.0]hexane-3-carboxylic acid tert-butyl ester (0.40 g, 1.4 mmol) in THF (10 mL) at −78° C. was added potassium bis(trimethylsilyl)amide (0.5M/toluene, 4.1 mL, 2.1 mmol) dropwise and the mixture was stirred for an additional 5 minutes. 1-Iodomethyl-3,5-bis-trifluoromethyl-benzene (0.69 g, 1.9 mmol) in THF (4 mL) was added and the reaction stirred at −78° C. for 10 minutes, then allowed to warm to room temperature and stirred for 2 hours. Water was added cautiously and the solvent removed at reduced pressure. The residue was partitioned between $H_2O$ and EtOAc, the organics were washed with brine and dried over calcium sulfate, filtered and concentrated to an oil. The crude product was purified by flash chromatography by elution with a gradient of hexanes to 20% EtOAc/Hexanes to give the title compound (0.52 g, 73% yield).

Rf=0.06 (15% EtOAc/hexanes).

Intermediate 25—Scheme 4

Step X (1S,2S)-1-(3,5-Bis-trifluoromethyl-benzyloxymethyl)-2-phenyl-3-aza-bicyclo[3.1.0]hexane (racemic)

A flask containing racemic Intermediate 24, one enantiomer being (1S,2S)-1-(3,5-bis-trifluoromethyl-benzyloxymethyl)-2-phenyl-3-aza-bicyclo[3.1.0]hexane-3-carboxylic acid tert-butyl ester (0.25 g, 0.49 mmol) and methylene chloride (10 mL) was immersed in a 0° C. bath. Trifluoroacetic acid (0.75 mL, 9.7 mmol) was added, and the reaction was stirred for 3 hours at room temperature. 20% NaOH solution was added cautiously and then saturated sodium bicarbonate solution was added until the pH=8. The phases were separated; the organics were washed with brine, dried over sodium sulfate, filtered, and concentrated to give the title compound (0.20 g, quantitative yield).

Example 5—Scheme 4

Step Y1

5-[1-(3,5-Bis-trifluoromethyl-benzyloxymethyl)-2-phenyl-3-aza-bicyclo[3.1.0]hex-3-ylmethyl]-2,4-dihydro-[1,2,4]triazol-3-one(racemic)

To racemic intermediate 25, one enantiomer being (1S, 2S)-1-(3,5-bis-trifluoromethyl-benzyloxymethyl)-2-phenyl-3-aza-bicyclo[3.1.0]hexane (0.075 g, 0.18 mmol) in DMF (1.2 mL) was added N-(1-amino-2-chloro-ethylidene)-hydrazinecarboxylic acid methyl ester (0.07 g, 0.42 mmol) and potassium carbonate (0.075 g, 0.54 mmol) and the mixture was heated to 60° C. for 1 hour then 140° C. for 2 hours. The reaction was partitioned between 1N LiCl solution and EtOAc, aqueous was re-extracted two times with EtOAc, the organics were washed with brine and dried over calcium sulfate, filtered and concentrated. The crude product was purified by flash chromatography using elution of a gradient of 50% EtOAc/Hexanes to 100% EtOAc to give the title compound. (0.039 g, 42% yield).

Example 6—Scheme 4

Step Y2

{5-[1-(3,5-Bis-trifluoromethyl-benzyloxymethyl)-2-phenyl-3-aza-bicyclo[3.1.0]hex-3-ylmethyl]-3H-[1,2,3]triazol-4-ylmethyl}-dimethyl-amine (racemic)

To racemic Intermediate 24, one enantiomer being (1S, 2S)-1-(3,5-bis-trifluoromethyl-benzyloxymethyl)-2-phenyl-3-aza-bicyclo[3.1.0]hexane (0.08 g, 0.18 mmol) in DME (1.0 mL) was added 5-dimethylaminomethyl-1H-[1,2,3]triazole-4-carbaldehyde (~50% pure, 0.14 g, 0.91 mmol) and the mixture stirred at room temperature for 3 hours. To the reaction flask was added sodium triacetoxyborohydride (0.08 g, 0.36 mmol) and stirring was continued for 16 hours. To the reaction flask was added 1 N HCl (2 mL) and the mixture stirred for 2 hours. 1 N NaOH solution was added cautiously and then saturated sodium bicarbonate solution was added until the pH=8. The reaction mixture was extracted with methylene chloride, the organics washed with brine, dried over sodium sulfate, filtered, and concentrated. The crude product was purified by flash chromatography using elution of a gradient of 50% EtOAc/Hexanes to 3% MeOH/EtOAc to give the title compound. (0.065 g, 66% yield).

Rf=0.13 (5% MeOH/EtOAC); LRMS m/z Calcd for C27H29F6N6O; 553. obsd LRMS m/z (M+1) 554.

Intermediate 28—Scheme 5

Step Z

Mixture of diastereomers (1R,2S)-3-benzyl-2-phenyl-3-aza-bicyclo[3.1.0]hexan-1-ol To a flame dried, 3 neck rbf equipped with an addition funnel was added THF (20 mL) and titanium(IV) isopropoxide (2.6 mL, 8.8 mmol) and the flask immersed in a −78° C. bath. To this mixture was added isopropylmagnesium chloride (2M/diethyl ether, 8.8 mL, 17.6 mmol) dropwise and stirring continued at −78° C. for 15 minutes. To the reaction flask was then added the starting material (S)-(allyl-benzyl-amino)-phenyl-acetic acid methyl ester (JACS, 19, 30, 1997, 6984) (~40% pure, 2.0 g, 2.7 mmol dropwise in THF (7 mL total) and the reaction was allowed to stir at −78° C. for 2.5 hours, warmed to −10° C., stirred for an additional 3 hours, allowed to warm to room temperature gradually and stirred for 16 hours. The reaction was poured carefully into a saturated Rochelle's Salt solution, solid sodium bicarbonate was added until the pH=8, EtOAc was added and the mixture allowed to stir for 1 hour. The phases were separated and the aqueous extracted with ETOAc, the combined organics were washed with brine and dried over calcium sulfate, filtered and concentrated. The crude product was purified on a Biotage flash 40 system eluted with a gradient of Hexanes to 12% ETOAc/Hexanes to give the title compound as an oil. (0.57 g, 32% yield).

Rf=0.20 (15% EtOAC/hexames); LRMS m/z Calcd for C18H19NO; 265. obsd LRMS m/z 265

Intermediate 29—Scheme 5

Step AA

Mixture of diastereomers, one being (1R,2S)-3-Benzyl-1-(3,5-bis-trifluoromethyl-benzyloxy)-2-phenyl-3-aza-bicyclo[3.1.0]hexane To Intermediate 28, mixture of diastereomers ((1R,2S)-3-benzyl-2-phenyl-3-aza-bicyclo[3.1.0]hexan-1-ol (0.40 g, 1.5 mmol) and tetrabutylammonium iodide (0.26 g, 0.70 mmol) in a flask was added THF (15 mL) and the mixture cooled to −78° C. Potassium bis(trimethylsilyl)amide (0.5M/toluene, 4.5 mL, 2.2 mmol) was added dropwise and the reaction was stirred for 10 minutes. 1-Bromomethyl-3,5-bis-trifluoromethyl-benzene (0.39 mL, 2.1 mmol) was added dropwise and the reaction stirred for an additional 10 minutes, then allowed to warm to room temperature. The solvent was removed at reduced pressure and the residue partitioned between H2O and EtOAc, the organics washed with brine and dried over calcium sulfate, filtered and concentrated. The crude product was purified on a Biotage flash 40 system eluted with a gradient of 1% ETOAc/Hexanes to 2% ETOAc/Hexanes to give the title compound as an oil. (0.55 g, 74% yield).

Rf=0.44, 0.37 (8% EtOAC/hexanes); LRMS m/z Calcd for C27H23F6NO; 491. obsd LRMS m/z (M+1) 492.

Example 7—Scheme 5

Step BB (1R,2S)-1-(3,5-Bis-trifluoromethyl-benzyloxy)-2-phenyl-3-aza-bicyclo[3.1.0]hexane The HCl salt of the starting material Intermediate 29 (0.6 g, 1.2 mmol), was prepared by dissolving it in an excess of 1 N HCl/MeOH and removing the solvent at reduced pressure. The salt of the starting material was then combined with palladium on carbon 20% (Pearlman's catalyst, 0.6 g) and EtOH (26 mL) and hydrogenated at 40 psi for 16 hours. The material was filtered thru celite and concentrated, then partitioned between saturated sodium bicarbonate solution and methylene chloride, the organics were washed with brine, dried over sodium sulfate, filtered, and concentrated to give the title compound as a mix of diastereomers (0.49 g, quantitative yield). A portion of this mixture (0.16 g, 0.39 mmol) was flash chromatographed on silica using a gradient of 50% ETOAc/Hexanes to 75% ETOAc/Hexanes as the eluant to give the less polar diastereomer (0.031 g), a portion of mixed diastereomers, and the more polar diastereomer (0.036 g)

Rf=0.34 (5% MeOH/EtOAC w/0.2% NH$_4$OH; LRMS m/z Calcd for C20H17F6NO; 401. obsd LRMS m/z (M+1) 402.

Example 8—Scheme 5

Step CC(i)

5-[(1R,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one To the starting material as mixture of diastereomers, Example 6 and Example 7, one being (1R,2S)-1-(3,5-Bis-trifluoromethyl-benzyloxy)-2-phenyl-3-aza-bicyclo[3.1.0] hexane, (0.100 g, 0.249 mmol), in DMF (1.2 mL) was added N-(1-amino-2-chloro-ethylidene)-hydrazinecarboxylic acid methyl ester (0.046 g, 0.28 mmol) and potassium carbonate (0.10 g, 0.75 mmol) and the mixture was heated to 60° C. for 1 hour then 140° C. for 3 hours. The reaction was partitioned between 1N LiCl solution and EtOAc, aqueous was re-extracted two times with EtOAc, the organics were washed with brine and dried over calcium sulfate, filtered and concentrated to an oil. The crude product was purified by flash chromatography using elution of a gradient of 20% EtOAc/Hexanes to 2% MeOH/EtOAc to afford the less polar diastereomer of the title compound. (0.017 g, 14% yield).

Rf=0.37 (100% EtOAc); LRMS m/z Calcd for C23H20F6N4O2; 498. obsd LRMS m/z (M+1) 499.

Example 9—Scheme 5

Step CC(ii)

5-[(1S,2S)-1-(3,5-bis-trifluoromethyl-benzyloxy)-2-phenyl-3-aza-bicyclo[3.1.0]hex-3-ylmethyl]-2,4-dihydro-[1,2,4]triazol-3-one To the starting material, a mixture of diastereomers, Example 6 and Example 7, one being (1S,2S)-1-(3,5-bis-trifluoromethyl-benzyloxy)-2-phenyl-3-aza-bicyclo[3.1.0] hexane, (0.10 g, 0.25 mmol), in DMF (1.2 mL) was added N-(1-amino-2-chloro-ethylidene)-hydrazinecarboxylic acid methyl ester (0.046 g, 0.28 mmol) and potassium carbonate (0.10 g, 0.75 mmol) and the mixture was heated to 60° C. for 1 hour then 140° C. for 3 hours. The reaction was partitioned between 1N LiCl solution and EtOAc, aqueous was re-extracted two times with EtOAc, the organics were washed with brine and dried over calcium sulfate, filtered and concentrated to an oil. The crude product was purified by flash chromatography using elution of a gradient of 20% EtOAc/Hexanes to 2% MeOH/EtOAc to afford the more polar diastereomer of the title compound (0.016 g, 13% yield).

Rf=0.25 (100% EtOAc); LRMS m/z Calcd for C23H20F6N4O2; 498. obsd LRMS m/z (M+1) 499.

Example 10—Scheme 5

Step CC(iii)

{5-[1-(3,5-Bis-trifluoromethyl-benzyloxy)-2-phenyl-3-aza-bicyclo[3.1.0]hex-3-ylmethyl-3H-[1,2,3]triazol-4-ylmethyl}-dimethyl-amine To the starting material, a mixture of diastereomers, Example 6 and Example 7, one being (1R,2S)-1-(3,5-bis-trifluoromethyl-benzyloxy)-2-phenyl-3-aza-bicyclo[3.1.0] hexane, (0.100 g, 0.249 mmol), in DME (1.0 mL) was added 5-dimethylaminomethyl-1H-[1,2,3]triazole-4-carbaldehyde (~50% pure, 0.15 g, 0.45 mmol) mmol and the mixture stirred at room temperature for 1.5 hours. To the reaction flask was added sodium triacetoxyborohydride (0.10 g, 0.50 mmol) and stirring was continued for 64 hours. The reaction flask was placed in a 0° C. bath and to the reaction flask was added 1N HCl (2 mL) and the mixture stirred for 4 hours at room temperature. 1N NaOH solution was added cautiously and then saturated sodium bicarbonate solution was added until the pH=8. The reaction mixture was extracted with methylene chloride, the organics washed with brine, dried over sodium sulfate, filtered, and concentrated to an oil. The crude product was purified by flash chromatography using elution with a gradient of 30% EtOAc/Hexanes to 100% EtOAc to give the less polar diastereomer of the title compound. (0.033 g, 25% yield).

Rf=0.19 (5% MeOH/EtOAC w/0.2% NH$_4$OH); LRMS m/z Calcd for C26H27F6N5O; 539. obsd LRMS m/z (M+1) 540.

Example 11—Scheme 5

CC(iv)

{5-[(1S,2S)-1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine To the starting material as a mixture of diastereomers, Example 6 and Example 7, one being (1S,2S)-1-(3,5-bis-trifluoromethyl-benzyloxy)-2-phenyl-3-aza-bicyclo[3.1.0] hexane, (0.10 g, 0.25 mmol) in DME (1.0 mL) was added 5-dimethylaminomethyl-1H-[1,2,3]triazole-4-carbaldehyde (~50% pure, 0.15 g, 0.45 mmol) mmol and the mixture stirred at room temperature for 1.5 hours. To the reaction flask was added sodium triacetoxyborohydride (0.10 g, 0.50 mmol) and stirring was continued for 64 hours. The reaction flask was placed in a 0° C. bath and to the reaction flask was added 1N HCl (2 mL) and the mixture stirred for 4 hours at room temperature. 1 N NaOH solution was added and then saturated sodium bicarbonate solution was added until the pH=8. The reaction mixture was extracted with methylene chloride, the organics washed with brine, dried over sodium sulfate, filtered, and concentrated to an oil. The crude product was purified by flash chromatography using elution with a gradient of 30% EtOAc/Hexanes to 100% EtOAc to give as the more polar diastereomer of the title compound. (0.034 g, 25% yield).).

Rf=0.12 (5% MeOH/EtOAC w/0.2% NH$_4$OH); LRMS m/z Calcd for C26H27F6N5O; 539. obsd LRMS m/z (M+1) 540.

Intermediate 32—Scheme 5

Step DD

Mixture of diastereomers, one being (1R,2S)-2-phenyl-3-aza-bicyclo[3.1.0]hexan-1-ol The HCl salt of the starting material Intermediate 28, mixture of diastereomers (1R,2S)-3-Benzyl-2-phenyl-3-aza-bicyclo[3.1.0]hexan-1-ol (1.2 g, 4.1 mmol), was combined with palladium on carbon 20% (Pearlman's catalyst, 0.7 g) and MeOH (35 mL) and hydrogenated at 40 psi for 16 hours. The material was filtered thru celite and concentrated to yield the title compounds as a mixture of diastereomers (0.88 g, quantitative yield).

LRMS m/z Calcd for C11H13NO; 175. obsd LRMS m/z (M+1) 176.

Example 12—Scheme 5

Step EE(i)

(1S,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide To a round bottom flask was added methylene chloride (12 mL), triethylamine (0.55 mL, 3.9 mmol), and [(S)-1-(3,5-Bis-trifluoromethyl-phenyl)-ethyl]-methyl-amine (0.35 g, 1.3 mmol. The mixture was cooled to 0° C. and triphosgene (0.15 g, 0.50 mmol) in methylene chloride (4 mL) was added dropwise. The clear solution was stirred for 16 hours at room temperature. To the reaction mixture was added Intermediate 32, mixture of diastereomers, one being (1S,2S)-2-phenyl-3-aza-bicyclo[3.1.0]hexan-1-ol HCl salt (0.25 g, 1.2 mmol), diisopropyl ethyl amine (0.41 mL, 2.4 mmol), and acetonitrile (10 mL). The reaction was heated to remove the methylene chloride and then refluxed for 1 hour. The solvent was removed at reduced pressure and the residue partitioned between 0.25N HCl and methylene chloride, the organic phase was washed with saturated sodium bicarbonate solution, brine, dried over sodium sulfate, filtered, and concentrated to a quantitative yield of oil. This material was flash chromatographed on silica using a gradient of 20 to 40% EtOAc/Hexanes and the first eluted spot was rechromatographed two times using prep tlc eluted with 5% MeOH/CHCl3 to afford the less polar diastereomer of the title compound (0.027 g, 4.8% yield).

Rf=0.36 (50% EtOAc/hexanes); LRMS m/z Calcd for C23H22F6N2O2; 472. obsd LRMS m/z 472.

Example 13—Scheme 5

Step EE

(1R,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide To a round bottom flask was added methylene chloride (12 mL), triethylamine (0.55 mL, 3.9 mmol), and [(S)-1-(3,5-Bis-trifluoromethyl-phenyl)-ethyl]-methyl-amine (0.35 g, 1.3 mmol. The mixture was cooled to 0° C. and triphosgene (0.15 g, 0.50 mmol) in methylene chloride (4 mL) was added dropwise. The clear solution was stirred for 16 hours at room temperature. To the reaction mixture was added a Intermediate 32, mixture of diastereomers, one being (1R,2S)-2-phenyl-3-aza-bicyclo[3.1.0]hexan-1-ol -HCl salt (0.25 g, 1.2 mmol), diisopropyl ethyl amine (0.41 mL, 2.4 mmol), and acetonitrile (10 mL). The reaction was heated to remove the methylene chloride and then refluxed for 1 hour. The solvent was removed at reduced pressure and the residue partitioned between 0.25N HCl and methylene chloride, the organic phase was washed with saturated sodium bicarbonate solution, brine, dried over sodium sulfate, filtered, and concentrated to a quantitative yield of oil. This material was flash chromatographed on silica using a gradient of 20 to 40% EtOAc/Hexanes to give the more polar diastereomer of the title compound (0.05 g, 8.9% yield).

Rf=0.25 (50% EtOAc/hexanes); LRMS m/z Calcd for C23H22F6N2O2; 472. obsd LRMS m/z 472.

Example 14—Scheme 5

Step FF

A mixture of diastereomers, one [(S)-1-(3,5-Bis-trifluoromethyl-phenyl)-ethyl]-methyl-carbamic acid (1R,2S)-2-phenyl-3-aza-bicyclo[3.1.0]hex-1-yl ester To a round bottom flask was added methylene chloride (12 mL), triethylamine (0.55 mL, 3.9 mmol), and [(S)-1-(3,5-bis-trifluoromethyl-phenyl)-ethyl]-methyl-amine (0.35 g, 1.3 mmol). The mixture was cooled to 0° C. and triphosgene (0.15 g, 0.50 mmol) in methylene chloride (4 mL) was added dropwise. The clear solution was stirred for 16 hours at room temperature. To the reaction mixture was added (2-phenyl-3-aza-bicyclo[3.1.0]hex-1-yl)-methanol (0.25 g, 1.2 mmol), diisopropyl ethyl amine (0.41 mL, 2.4 mmol), and acetonitrile (10 mL). The reaction was heated to remove the methylene chloride and then refluxed for 1 hour. The solvent was removed at reduced pressure and the residue partitioned between 0.25N HCl and methylene chloride, the organic phase was washed with saturated sodium bicarbonate solution, brine, dried over sodium sulfate, filtered, and concentrated to a quantitative yield of oil. This material was flash chromatographed on silica using a gradient of 20 to 40% EtOAc/Hexanes and the first eluted (Rf=0.39 (50% EtOAc/hexanes) spot was rechromatographed using prep TLC eluting with 5% MeOH/CHCl3 to afford the title compound as a mixture of diasteomers (0.031 g, 5.5% yield) and as an oil.

Rf mixture of diastereomers=0.39 (50% EtOAc/hexanes); LRMS m/z Calcd for C23H22F6N2O2; 472. obsd LRMS m/z (M+1) 473.

Intermediate 35—Scheme 6

Step GG

1-Hydroxymethyl-2-phenyl-3-aza-bicyclo[3.1.0]hexane-3-carboxylic acid[1-(3,5-bis-trifluoromethyl-phenyl)-ethyl]-methyl-amide Mixture of 4 isomers, one being (1S,2S)-1-hydroxymethyl-2-phenyl-3-aza-bicyclo[3.1.0]hexane-3-carboxylic acid [(R)-1-(3,5-bis-trifluoromethyl-phenyl)-ethyl]-methyl-amide. To a round bottom flask was added methylene chloride (8 mL), triethylamine (0.63 mL, 5.0 mmol), and [1-(3,5-bis-trifluoromethyl-phenyl)-ethyl]-methyl-amine (0.36 g, 1.2 mmol). The mixture was cooled to 0° C. and triphosgene (0.13 g, 0.49 mmol) in methylene chloride (3 mL) was added dropwise. The slurry was stirred for 16 hours at room temperature. To the mixture was added racemic Intermediate 17 ((1S,2S)-2-phenyl-3-aza-bicyclo

[3.1.0]hex-1-yl)-methanol (0.20 g, 1.1 mmol) and diisopropyl ethyl amine (0.19 mL, 1.2 mmol) in acetonitrile (8 mL). The reaction was heated to remove the methylene chloride and then refluxed for 2 hours. The solvent was removed at reduced pressure and the residue partitioned between 1N HCl and methylene chloride, the organic phase was washed with brine, dried over sodium sulfate, filtered, and concentrated to an oil. The crude product was purified on a Biotage Flash 40 system eluted with 20% ETOAc/Hexanes to give the title compound as an oil which is a 1:1 mix of racemic diastereomers (0.29 g, 57% yield).

Rf (mixture of racemic diastereomers)=0.28 (50% EtOAc/hexanes); LRMS m/z Calcd for C24H24F6N2O2; 486. obsd LRMS m/z (M+1) 487.

Intermediate 36—Scheme 6

Step HH

Mixture of 4 isomers, one being methanesulfonic acid (1S,2S)-3-{[(R)-1-(3,5-bis-trifluoromethyl-phenyl)-ethyl]-methyl-carbamoyl}-2-phenyl-3-aza-bicyclo[3.1.0]hex-1-ylmethyl ester To a stirred solution of Intermediate 35, 4 isomers, one being (1S,2S)-1-Hydroxymethyl-2-phenyl-3-aza-bicyclo[3.1.0]hexane-3-carboxylic acid [(R)-1-(3,5-bis-trifluoromethyl-phenyl)-ethyl]-methyl-amide (0.28 g, 0.57 mmol) and triethylamine (0.13 mL, 0.96 mmol) in methylene chloride (6 mL) at 0° C. was added methanesulfonyl chloride (0.06 mL, 0.79 mmol). The reaction was allowed to warm to room temperature and stir for 2 hours. The reaction was washed with cold 0.5N HCl and the phases separated. The methylene chloride was washed with cold 0.5N NaOH, washed with brine, and dried over sodium sulfate, filtered and concentrated to give the title compound as a pink foam (0.32 g, quantitative yield). This material was processed without further purification.

Rf=0.29 (50% EtOAc/hexanes); ); LRMS m/z Calcd for C25H26F6N2O4S; 564. obsd LRMS m/z (M+1) 565.

Example 15—Scheme 6

Step II(i)

Mixture of four isomers, one being (1R,2S)-1-methylaminomethyl-2-phenyl-3-aza-bicyclo[3.1.0]hexane-3-carboxylic acid [(R)-1-(3,5-bis-trifluoromethyl-phenyl)-ethyl]-methyl-amide To a stirred solution of Intermediate 36, mixture of 4 isomers, one being methanesulfonic acid (1S,2S)-3-{[(R)-1-(3,5-bis-trifluoromethyl-phenyl)-ethyl]-methyl-carbamoyl}-2-phenyl-3-aza-bicyclo[3.1.0]hex-1-ylmethyl ester (0.16 g, 0.27 mmol) in THF (6 mL) at 0° C. was added methylamine gas via a pipette as a stream of constant bubbles under the surface of the reaction. The reaction was allowed to warm to room temperature and stirr for 16 hours. The solvent was removed at reduced pressure and the residue partitioned between saturated sodium bicarbonate solution and methylene chloride. The organics were washed with brine, dried over sodium sulfate, filtered, and concentrated. The crude product was purified by prep tlc eluted with 5% MeOH, 0.1% NH4OH/EtOAc to give the title compounds (0.061 g, 44% yield).

Rf=0.22 (9% MeOH/EtOAc); LRMS m/z Calcd for C25H27F6N3O; 499. obsd LRMS m/z (M+1) 500.

Example 16—Scheme 6

Step II(ii)

Mixture of four isomers, one being (1R,2S)-1-aminomethyl-2-phenyl-3-aza-bicyclo[3.1.0]hexane-3-carboxylic acid [(R)-1-(3,5-bis-trifluoromethyl-phenyl)-ethyl]-methyl-amide To a stirred solution of Intermediate 36, mixture of 4 isomers, one being methanesulfonic acid (1S,2S)-3-{[(R)-1-(3,5-bis-trifluoromethyl-phenyl)-ethyl]-methyl-carbamoyl}-2-phenyl-3-aza-bicyclo[3.1.0]hex-1-ylmethyl ester (0.15 g, 0.27 mmol) in EtOH (6 mL) was added ammonium hydroxide (28-30% in water, 6.0 mL). The reaction was stoppered and stirred at room temperature for 18 hours. The solvent was removed at reduced pressure and the residue partitioned between saturated sodium bicarbonate solution and methylene chloride, the organics were washed with brine, dried over sodium sulfate, filtered, and concentrated to an oil. The crude products was purified by prep tlc eluted with 3% MeOH, 0.25% NH4OH/EtOAc to give the title compounds (0.034 g, 26% yield).

Rf=0.22 (5% MeOH/EtOAc); LRMS m/z Calcd for C24H25F6N3O; 485. obsd LRMS m/z (M+1) 486.

Intermediate 38—Scheme 6

Step JJ

Racemic mixture, one enantiomer being ((1S,2S)-3-benzyl-2-phenyl-3-aza-bicyclo[3.1.0]hex-1-yl)-methanol To a stirred solution of racemic Intermediate 17, one enantiomer being ((1S,2S)-2-phenyl-3-aza-bicyclo[3.1.0]hex-1-yl)-methanol (0.50 g, 2.6 mmol), in MeOH (7 mL) was added sodium carbonate (0.56 g, 5.3 mmol) then alpha-bromotoluene (0.33 mL, 2.8 mmol).

The reaction was stirred at room temperature for 16 hours. The solvent was removed at reduced pressure and the residue partitioned between water and methylene chloride, the organics were washed with brine, dried over sodium sulfate, filtered, and concentrated to give the title compound (0.69 g, 93% yield) as an oil.

LRMS m/z Calcd for C19H21NO; 279. obsd LRMS m/z (M+1) 280

Intermediate 39—Scheme 6

Step KK (1S,2S)-3-benzyl-2-phenyl-3-aza-bicyclo[3.1.0]hexane-1-carboxylic acid (racemic)

To a stirred solution of racemic Intermediate 38, one enantiomer being ((1S,2S)-3-benzyl-2-phenyl-3-aza-bicyclo[3.1.0]hex-1-yl)-methanol (0.69 g, 2.5 mmol) in acetone (20 mL) was added Jones Reagent (3 mL) dropwise with stirring. Additional acetone (50 mL) was added and the material was triturated then filtered to remove the solid. The filtrate was concentrated and partitioned between water of pH=6 and methylene chloride. The organics were washed with brine, dried over sodium sulfate, filtered, and concentrated to give the title compound (0.45 g, 62% yield).

LRMS m/z Calcd for C19H19NO2; 293. obsd LRMS m/z (M+1) 294

Intermediate 40—Scheme 6

Step LL (1S,2S)-3-Benzyl-2-phenyl-3-aza-bicyclo[3.1.0] hexane-1-carbonyl chloride (racemic)

To racemic Intermediate 39, one enantiomer being (1S, 2S)-3-benzyl-2-phenyl-3-aza-bicyclo[3.1.0]hexane-1-carboxylic acid (0.16 g, 0.56 mmol) was added thionyl chloride (2 mL) dropwise with stirring. The homogeneous solution was refluxed gently for 2 hours. The solvent was removed at reduced pressure to yield the title compound (0.17 g, quantitative yield) as an oil, which was used without further purification.

Example 17A—Scheme 6

Step MM(i)

((1R,2R)-3-Benzyl-2-phenyl-3-aza-bicyclo[3.1.0] hexane-1-carboxylic acid [(S)-1-(3,5-bis-trifluoromethyl-phenyl)-ethyl]-methyl-amide To racemic Intermediate 40, one enantiomer being (1R, 2R)-3-benzyl-2-phenyl-3-aza-bicyclo[3.1.0]hexane-1-carbonyl chloride (0.17 g, 0.56 mmol) in MC (5 mL) was added triethylamine (0.23 mL, 1.7 mmol) and (S)-1-(3,5-bis(trifluoromethyl)phenyl)-N-methylethanamine 0.15 g, 0.56 mmol) in MC (1 mL). The reaction was allowed to stir at room temperature overnight. The reaction was diluted with saturated sodium bicarbonate solution and the phases separated. The organics were washed with brine, dried over sodium sulfate, filtered, and concentrated to an oil. This material was flash chromatographed on silica using a gradient of 5 to 10% EtOAc/Hexanes to afford the title compound (0.056 g, 18% yield).

Rf=0.42 (20% EtOAc/hexanes); LRMS m/z Calcd for C30H28F6N2O; 546. obsd LRMS m/z (M+1) 547.

Example 17B—Scheme 6

Step MM(ii)

(1S,2S)-3-Benzyl-2-phenyl-3-aza-bicyclo[3.1.0] hexane-1-carboxylic acid [(S)-1-(3,5-bis-trifluoromethyl-phenyl)-ethyl]-methyl-amide To racemic Intermediate 40, one enantiomer being (1S, 2S)-3-benzyl-2-phenyl-3-aza-bicyclo[3.1.0]hexane-1-carbonyl chloride (0.17 g, 0.56 mmol) in MC (5 mL) was added triethylamine (0.24 mL, 1.7 mmol) and (S)-1-(3,5-bis(trifluoromethyl)phenyl)-N-methylethanamine 0.15 g, 0.56 mmol) in MC (1 mL). The reaction was stirred at room temperature overnight. The reaction was diluted with saturated sodium bicarbonate solution and the phases separated. The organics were washed with brine, dried over sodium sulfate, filtered, and concentrated to an oil. This material was flash chromatographed on silica using a gradient of 5 to 10% EtOAc/Hexanes to afford the title compound (0.06 g, 19% yield).

Rf=0.19 (20% EtOAc/hexanes); LRMS m/z Calcd for C30H28F6N2O; 546. obsd LRMS m/z (M+1) 547.

Example 18

Scheme 6

Step NN (1S,2S)-2-Phenyl-3-aza-bicyclo[3.1.0]hexane-1-carboxylic acid [(S)-1-(3,5-bis-trifluoromethyl-phenyl)-ethyl]-methyl-amide To Intermediate 41, the more polar isomer (1S,2S)-3-benzyl-2-phenyl-3-aza-bicyclo[3.1.0]hexane-1-carboxylic acid [(S)-1-(3,5-bis-trifluoromethyl-phenyl)-ethyl]-methyl-amide (0.06 g, 0.11 mmol) was combined with palladium on carbon 20% (Pearlman's catalyst, 0.08 g) and HOAc (8 mL) and hydrogenated at 40 psi for 16 hours. The material was filtered thru celite and concentrated, then partitioned between saturated sodium bicarbonate solution and methylene chloride, the organics were washed with brine, dried over sodium sulfate, filtered, and concentrated. The crude material was purified via prep tlc using ETOAc as the eluant to give the title compound (0.027 g, 54% yield).

Rf=0.11 (75% EtOAc/hexanes); LRMS m/z Calcd for C23H22F6N2O; 456. obsd LRMS m/z (M+1) 457.

Intermediate 43—Scheme 7

Step OO (1S,2S)-2-Phenyl-3-tosyl-3-aza-bicyclo[3.1.0]hexane-1-carboxylic acid (racemic)

To a stirred solution of racemic Intermediate 16, one enantiomer being [(1S,2S)-2-phenyl-3-(toluene-4-sulfonyl)-3-aza-bicyclo[3.1.0]hex-1-yl]-methanol I (34.5 g, 101 mmol) in acetone (1330 mL) was added Jones Reagent (104 mL) dropwise with stirring. The orange solution was stirred for another 20 minutes. MeOH (~10 mL) was added cautiously until the solution turned green. The solvent was removed at reduced pressure and the residue partitioned between water and methylene chloride. The organics were washed with brine, dried over sodium sulfate, filtered, and concentrated. This material was flash chromatographed on silica using a gradient of 10% to 80% EtOAc/Hexanes to give the title compound (23.0 g, 64% yield) as a yellow solid.

Rf=0.2 (60% EtOAc/hexanes).

Intermediate 4—Scheme 7

Step PP (1S,2S)-2-Phenyl-3-tosyl-3-aza-bicyclo[3.1.0]hexane-1-carbonyl chloride (racemic)

To racemic Intermediate 43, one enantiomer being (1S, 2S)-2-phenyl-3-(toluene-4-sulfonyl)-3-aza-bicyclo[3.1.0] hexane-1-carboxylic acid (10.0 g, 28.0 mmol) slurried in toluene (67 mL) was added DMF (3 drops). The mixture was cooled to 0° C. and thionyl chloride (5.72 mL, 78.4 mmol) was added dropwise with stirring. The homogeneous solution was heated to 73° C. for 2.5 hours. The solvent was removed at reduced pressure. The residue was brought up in toluene two times and the solvent was removed at reduced pressure each time to yield the title compounds (10.5 g, quantitative yield) as an oil.

Rf=0.23 (20% EtOAc/hexanes); LRMS m/z Calcd for C19H18ClNO3S; 375. obsd LRMS m/z (M+1) 376.

Intermediate 45—Scheme 7

Step QQ

Azido(((1S,2S)-2-Phenyl-3-tosyl-3-aza-bicyclo[3.1.0]hexan-1-yl)methanone (racemic)

To a stirred solution of sodium azide (11.83 g, 182.0 mmol) in water (37 mL) was added in a dropwise fashion a solution of racemic Intermediate 44, one enantiomer being (1S,2S)-2-phenyl-3-tosyl-3-aza-bicyclo[3.1.0]hexane-1-carbonyl chloride (10.5 g, 28.01 mmol) in acetone (60 mL). The reaction was allowed to stir for 2 hours at which time much white precipitate has formed. Stirring was continued for another 16 hours. The acetone was removed at reduced pressure and the reaction diluted with both methylene chloride and brine. The organic layer was separated, dried over sodium sulfate, filtered, and concentrated under reduced pressure to give the title compounds (10.1 g, 100% crude yield) as a tan foam.

Rf=0.23 (20% EtOAc/hexanes); LRMS m/z Calcd for C19H18N4O3S; 382. obsd LRMS m/z (M+1) 383.

Intermediate 46—Scheme 7

Step RR (1S,2S)-1-Isocyanato-2-phenyl-3-tosyl-3-aza-bicyclo[3.1.0]hexane (racemic)

A solution of racemic Intermediate 45, one enantiomer being (1S,2S)-2-phenyl-3-(toluene-4-sulfonyl)-3-aza-bicyclo[3.1.0]hexane-1-carbonyl azide (10.7 g, 28.0 mmol) in 220 mL toluene was heated to 90° C. for 16 hours. The solvent was removed at reduced pressure to leave the title compounds (9.92 g, quantitative yield), which was used without further purification.

Rf=0.27 (75% EtOAc/hexanes).

Intermediate 47—Scheme 7

Step SS tert-Butyl (1S,2S)-2-Phenyl-3-tosyl-3-aza-bicyclo]3.1.0]hexan-1ylcarbamate (racemic)

To a solution of racemic Intermediate 46, one enantiomer being (1S,2S)-1-Isocyanato-2-phenyl-3-tosyl-3-aza-bicyclo[3.1.0]hexane (1.00 g, 2.82 mmol) and tert-butyl alcohol (0.81 mL, 8.5 mmol) in MC (11.5 mL) at 0° C. was added chlorotrimethylsilane (0.57 mL, 4.5 mmol) dropwise. The reaction was allowed to warm to room temperature and stir for 16 hours. The reaction was placed in a 0° C. bath and saturated sodium bicarbonate solution (~20 mL) was added dropwise and the mixture stirred at room temperature for 1 hour. The phases were separated and the organic washed with brine, dried over sodium sulfate, filtered, and the filtrate concentrated. The crude material was purified by flash chromatography on silica using a gradient of 20% EtOAc/Hexanes to 40% EtOAc/Hexanes as eluant. The title compound was obtained as a white crystalline solid (0.90 g, 74% yield).

Rf=0.62 (50% EtOAc/hexanes); LRMS m/z Calcd for C23H28N2O4S; 428. obsd LRMS m/z (M+1) 429.

Intermediate 48—Scheme 7

Step TT

Racemic, one enantiomer being ((1S,2S)-2-Phenyl-3-aza-bicyclo[3.1.0]hex-1-yl)-carbamic acid tert-butyl ester To a flame dried 250 mL rbf equipped with a dry ice condenser was added fresh sodium metal (0.32 g, 14 mmol). The flask was immersed in a −78° C. bath and ammonia gas was condensed into the flask (~30 mL). Racemic Intermediate 47, one enantiomer being [(1S,2S)-2-phenyl-3-(toluene-4-sulfonyl)-3-aza-bicyclo[3.1.0]hex-1-yl]-carbamic acid tert-butyl ester (3.0 g, 7.0 mmol) in THF (7 mL, 2 mL rinse) was added to the flask in a fast dropwise fashion and the thick mixture was stirred for 5 minutes at which point tic indicated the reaction was complete. The reaction was warmed to room temperature and volatile solvents allowed to evaporate. The residue was partitioned between H₂O and methylene chloride, the organics were washed with brine, dried over sodium sulfate, filtered, and concentrated to give the title compound as a foam (1.9 g, quantitative yield).

Rf=0.47 (10% MeOH/EtOAc w/0.2% NH4OH); LRMS m/z Calcd for C16H22N2O2; 274. obsd LRMS m/z (M+1) 275.

Intermediate 49—Scheme 7

Step UU

Mixture of four isomers, one being ((1S,2S)-3-{[(S)-1-(3,5-Bis-trifluoromethyl-phenyl)-ethyl]-methyl-carbamoyl}-2-phenyl-3-aza-bicyclo[3.1.0]hex-1-yl)-carbamic acid tert-butyl ester To a round bottom flask was added methylene chloride (8 mL), triethylamine (0.87 mL, 6.3 mmol), and [(SR)-1-(3,5-bis-trifluoromethyl-phenyl)-ethyl]-methyl-amine (0.49 g, 1.6 mmol. The mixture was cooled to 0° C. and triphosgene (0.18 g, 0.61 mmol) in methylene chloride (3 mL) was added dropwise. The clear solution was stirred for 16 hours at room temperature. To the reaction mixture was added racemic Intermediate 48, one enantiomer being ((1S,2S)-2-phenyl-3-aza-bicyclo[3.1.0]hex-1-yl)-carbamic acid tert-butyl ester (0.40 g, 1.5 mmol), diisopropyl ethyl amine (0.25 mL, 1.5 mmol), and acetonitrile (8 mL). The reaction was heated to remove the methylene chloride and then refluxed for 2 hours. The solvent was removed at reduced pressure and the residue was partitioned between saturated citric acid solution and methylene chloride. The organic phase was washed with saturated sodium bicarbonate solution, brine, dried over sodium sulfate, filtered, and concentrated to give the title compounds as a foam (0.84 g, quantitative yield).

Rf=0.54 (50% EtOAc/hexanes); LRMS m/z Calcd for C28H31F6N3O3; 571. obsd LRMS m/z (M+1) 572.

Intermediate 50—Scheme 7

Step VV

Mixture of four isomers, one being ((1S,2S)-3-{[(S)-1-(3,5-Bis-trifluoromethyl-phenyl)-ethyl]-methyl-carbamoyl}-2-phenyl-3-aza-bicyclo[3.1.0]hex-1-yl)-methyl-carbamic acid tert-butyl ester Intermediate 49, mixture of four isomers, one being ((1S,2S)-3-{[(S)-1-(3,5-bis-trifluoromethyl-phenyl)-ethyl]-methyl-carbamoyl}-2-phenyl-3-aza-bicyclo[3.1.0]hex-1- yl)-carbamic acid tert-butyl ester (0.30 g, 0.52 mmol), was slurried in DMF (3 mL) and the mixture cooled to 0° C. Sodium hydride (oil free, 0.038 g, 1.6 mmol) was added in portions and the reaction was then stirred for 1 hour at room temperature. Methyl iodide (0.098 mL, 1.6 mmol) was added and the reaction stirred an additional 2 hours at room temperature. The mixture was partitioned between 1N lithium chloride solution and EtOAc, the organics were washed with brine and dried over calcium sulfate, filtered and concentrated. Flash chromatography on silica using a gradient of 5% EtOAc/Hexanes to 20% EtOAc/Hexanes as eluant gave the title compounds as a white foam (0.17 g, 57% yield).

Rf=0.19 (20% EtOAc/hexanes); LRMS m/z Calcd for C29H33F6N3O3; 585. obsd LRMS m/z (M+1) 586.

Example 19—Scheme 7

Step WW

Mixture of four isomers, one being (1S,2S)-1-methylamino-2-phenyl-3-aza-bicyclo[3.1.0]hexane-3-carboxylic acid [(S)-1-(3,5-bis-trifluoromethyl-phenyl)-ethyl]-methyl-amide A flask containing Intermediate 50, a mixture of four isomers, one being ((1S,2S)-3-{[(S)-1-(3,5-bis-trifluoromethyl-phenyl)-ethyl]-methyl-carbamoyl}-2-phenyl-3-aza-bicyclo[3.1.0]hex-1-yl)-methyl-carbamic acid tert-butyl ester (0.17 g, 0.30 mmol), and methylene chloride (5 mL) was immersed in a 0° C. bath. Trifluoroacetic acid (0.46 mL, 6.0 mmol) was added, and the reaction stirred for 16 hours at room temperature. The solvent was removed at reduced pressure and the residue partitioned between saturated sodium bicarbonate solution and methylene chloride, the organics were washed with brine, dried over sodium sulfate, filtered, and concentrated to give the title compound as an oil (0.15 g, quantitative yield).

Rf=0.22 (2% MeOH/EtOAc w/0.2% NH4OH); LRMS m/z Calcd for C24H25F6N3O; 486. obsd LRMS m/z (M+1) 487.

Example 20—Scheme 7

Step XX

Mixture of four isomers, one being (1S,2S)-1-Amino-2-phenyl-3-aza-bicyclo[3.1.0]hexane-3-carboxylic acid [(S)-1-(3,5-bis-trifluoromethyl-phenyl)-ethyl]-methyl-amide A flask containing Intermediate 49, a mixture of four isomers, one being ((1S,2S)-3-{[(S)-1-(3,5-bis-trifluoromethyl-phenyl)-ethyl]-methyl-carbamoyl}-2-phenyl-3-aza-bicyclo[3.1.0]hex-1-yl)-carbamic acid tert-butyl ester (0.54 g, 0.95 mmol), and methylene chloride (10 mL) was immersed in a 0° C. bath. Trifluoroacetic acid (1.5 mL, 19.2 mmol) was added dropwise, and the reaction stirred for 16 hours at room temperature. The reaction was cooled to 0° C. and 1N NaOH then saturated sodium bicarbonate solution was added until the pH~9, the phases were separated, the organics washed with brine, dried over sodium sulfate, filtered, and concentrated. Flash chromatography using the biotage flash 40 system eluted with a gradient of 25% EtOAc/Hexanes thru 100% EtOAc and finally 5% MeOH/EtOAc as eluant gave the title compounds (0.22 g, 50% yield).

Rf=0.16 (100% EtOAc); LRMS m/z Calcd for C23H23F6N3O; 471. obsd LRMS m/z (M+1) 472.

Intermediate 38—Scheme 7

Step YY

Mixture of enantiomers, one being [(1S,2S)-2-Phenyl-3-(2,2,2-trifluoro-acetyl)-3-aza-bicyclo[3.1.0] hex-1-yl]-carbamic acid tert-butyl ester To racemic Intermediate 48, one enantiomer being ((1S,2S)-2-phenyl-3-aza-bicyclo[3.1.0]hex-1-yl)-carbamic acid tert-butyl ester (3.2 g, 11.5 mmol) dissolved in methylene chloride (39 mL) was added triethylamine (2.4 mL, 17.2 mmol). The solution was cooled to 0° C. and trifluoroacetic anhydride (1.8 mL, 12.6 mmol) was added. The reaction was stirred at 0° C. for 20 minutes then allowed to warm to room temperature and stir for 3 hours. Saturated sodium bicarbonate solution was added, the phases were separated, the organics washed with brine, dried over sodium sulfate, filtered, and concentrated to give the title compound as a foam (4.4 g, quantitative yield).

Rf=0.69 (100% EtOAc).

Intermediate 54—Scheme 7

Step ZZ 1-((1S,2S)-1-amino-2-phenyl-3-aza-bicyclo[3.1.0] hexane-3-yl)-2,2,2-trifluoroethanone (racemic)

A flask containing the racemic Intermediate 53, one enatiomer being [(1S,2S)-2-phenyl-3-(2,2,2-trifluoro-acetyl)-3-aza-bicyclo[3.1.0]hex-1-yl]-carbamic acid tert-butyl ester (4.3 g, 11.5 mmol) and methylene chloride (75 mL) was immersed in a 0° C. bath, trifluoroacetic acid (8.0 mL, 103 mmol) was added dropwise, and the reaction stirred at 0° C. for 5 minutes then allowed to warm to room temperature and stir for 5 hours. The solvent was removed at reduced pressure and the material dried in vacuo to give the title compound as a trifluoroacetic acid salt. (quantitative yield).

Rf=0.31 (100% EtOAc); LRMS m/z Calcd for C13H13F3N2O; 270. obsd LRMS m/z (M+1) 271.

Example 15—Scheme 7

Step AAA (2-Methoxy-5-trifluoromethoxy-benzyl)-((1S,2S)-2-Phenyl-3-aza-bicyclo[3.1.0]hex-1-yl)-amine The starting material, racemic Intermediate 54, one enantiomer being 1-((1S,2S)-1-amino-2-phenyl-3-aza-bicyclo [3.1.0]hex-3-yl)-2,2,2-trifluoro-ethanone (0.10 g, 0.26 mmol), was combined with 5-(1,1-trifluoro-ethoxy)-2-methoxy-benzaldehyde (0.074 g, 0.34 mmol), in 3 mL CH2Cl2, 1 mL MeOH, and 15 mL toluene. The reaction vessel was fitted with a Dean Stark trap and heated to reflux for 1 hr. The reaction was cooled to rt and concentrated under reduced pressure. The crude material was taken up in methylene chloride and washed with saturated sodium bicarbonate. The organic layer was dried over Na2SO4, filtered and concentrated. The crude imine was taken up in 1,2-dichlorethane (6 mL), and 3 drops of HOAc were added, followed by sodium triacetoxy borohydride (375 mg, 1.8 mmol). After 48 hr the reaction was diluted with methylene chloride and quenched with a saturated solution of sodium bicarbonate. The organic layer was dried over Na2SO4, filtered and concentrated to yield the intermediate racemate, one enantiomer being, 2,2,2-Trifluoro-1-[(1S,2S)-1-(2-methoxy-5-trifluoromethoxy-benzylamino)-2-phenyl-3-aza-bicyclo[3.1.0]hex-3-yl]-ethanone (0.14 g). This crude material was taken up in EtOH (6 mL) and sodium borohydride (0.020 g, 0.53 mmol) was added. After 16 hr the reaction was concentrated, then diluted with methylene chloride and washed with saturated sodium bicarbonate. The organic layer was dried over Na2SO4, filtered and concentrated. Purification of this material was accomplished by flash column chromatography using a gradient of 75%, 100% EtOAc/hexanes and then 2% MeOH/EtOAc to give the title compounds (0.032 g, 33% yield over two steps)

Rf=0.2 (5% MeOH/CH2Cl2 w/0.1% NH4OH); LRMS m/z Calcd for C20H21F3N2O; 378. obsd LRMS m/z (M+1) 279.

Exemplary compounds of Formula I in accordance with the present invention are the following:

(1aS,2R)-6-Methoxy-3-methyl-5-[((1R,2S,5S)-2-phenyl-3-aza-bicyclo[3.1.0]hex-1-ylamino)-methyl]-1,1a,3,7b-tetrahydro-3-aza-cyclopropa[a]naphthalen-2-one (5-tert-Butyl-2-methoxy-benzyl)-((1R,2S,5S)-2-phenyl-3-aza-bicyclo[3.1.0]hex-1-yl)-amine (6-Methoxy-1-methyl-1-trifluoromethyl-isochroman-7-ylmethyl)-((1R,2S,5S)-2-phenyl-3-aza-bicyclo[3.1.0]hex-1-yl)-amine (1R,2S,5S)-1-Methylamino-2-phenyl-3-aza-bicyclo[3.1.0]hexane-3-carboxylic acid [1-((R)-3,5-bis-trifluoromethyl-phenyl)-ethyl]-methyl-amide trifluroacetic acid salt (1S,2S,5R)-1-Methylamino-2-phenyl-3-aza-bicyclo[3.1.0]hexane-3-carboxylic acid [1-((R)-3,5-bis-trifluoromethyl-phenyl)-ethyl]-methyl-amide (1S,2R,5R)-1-Methylamino-2-phenyl-3-aza-bicyclo[3.1.0]hexane-3-carboxylic acid [1-((S)-3,5-bis-trifluoromethyl-phenyl)-ethyl]-methyl-amide trifluro acetic acid (1R,2S,5S)-1-Methylamino-2-phenyl-3-aza-bicyclo[3.1.0]hexane-3-carboxylic acid [1-((S)-3,5-bis-trifluoromethyl-phenyl)-ethyl]-methyl-amide trifluro acetic acid salt (1R,2S,5S)-1-{[((1S,7bR)-6-Methoxy-3-methyl-2-oxo-1a,2,3,7b-tetrahydro-1H-3-aza-cyclopropa[a]naphthalen-5-ylmethyl)-amino]-methyl}-2-phenyl-3-aza-bicyclo[3.1.0]hexane-3-carboxylic acid tert-butyl ester (6-Methoxy-1-methyl-1-trifluoromethyl-isochroman-7-ylmethyl)-((1R,2S)-2-phenyl-3-aza-bicyclo[3.1.0]hex-1-ylmethyl)-amine (1S,2S)-1-(3,5-Bis-trifluoromethyl-benzyloxymethyl)-2-phenyl-3-aza-bicyclo[3.1.0]hexane 5-[(1S,2S)-1-(3,5-Bis-trifluoromethyl-benzyloxymethyl)-2-phenyl-3-aza-bicyclo[3.1.0]hex-3-ylmethyl]-2,4-dihydro-[1,2,4]triazol-3-one {5-[(1S,2S)-1-(3,5-Bis-trifluoromethyl-benzyloxymethyl)-2-phenyl-3-aza-bicyclo[3.1.0]hex-3-ylmethyl]-1H-[1,2,3]triazol-4-ylmethyl}-dimethyl-amine (1S,2S)-1-(3,5-Bis-trifluoromethyl-benzyloxymethyl)-2-phenyl-3-aza-bicyclo[3.1.0]hexane-3-carboxylic acid [(S)-1-(3,5-bis-trifluoromethyl-phenyl)-ethyl]-methyl-amide (1R,2S)-1-(3,5-Bis-trifluoromethyl-benzyloxy)-2-phenyl-3-aza-bicyclo[3.1.0]hexane (1S,2S)-1-(3,5-Bis-trifluoromethyl-benzyloxy)-2-phenyl-3-aza-bicyclo[3.1.0]hexane 5-[(1R,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one 5-[(1S,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one {5-[(1R,2S)-1-(3,5-Bis-trifluoromethyl-benzyloxy)-2-phenyl-3-aza-bicyclo[3.1.0]hex-3-ylmethyl]-3H-[1,2,3]triazol-4-ylmethyl}-dimethyl-amine {5-[(1S,2S)-1-(3,5-Bis-trifluoromethyl-benzyloxy)-2-phenyl-3-aza-bicyclo[3.1.0]hex-3-ylmethyl]-3H-[1,2,3]triazol-4-ylmethyl}-dimethyl-amine (1S,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide (1R,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide

[(S)-1-(3,5-Bis-trifluoromethyl-phenyl)-ethyl]-methyl-carbamic acid (1R,2S)-2-phenyl-3-aza-bicyclo[3.1.0]hex-1-yl ester (1S,2S)-1-Hydroxymethyl-2-phenyl-3-aza-bicyclo[3.1.0]hexane-3-carboxylic acid [(R)-1-(3,5-bis-trifluoromethyl-phenyl)-ethyl]-methyl-amide (1R,2S)-1-methylaminomethyl-2-phenyl-3-aza-bicyclo[3.1.0]hexane-3-carboxylic acid [(R)-1-(3,5-bis-trifluoromethyl-phenyl)-ethyl]-methyl-amide (1R,2S)-1-Aminomethyl-2-phenyl-3-aza-bicyclo[3.1.0]hexane-3-carboxylic acid [(R)-1-(3,5-bis-trifluoromethyl-phenyl)-ethyl]-methyl-amide (1R,2R)-3-Benzyl-2-phenyl-3-aza-bicyclo[3.1.0]hexane-1-carboxylic acid [(S)-1-(3,5-bis-trifluoromethyl-phenyl)-ethyl]-methyl-amide (1S,2S)-2-Phenyl-3-aza-bicyclo[3.1.0]hexane-1-carboxylic acid [(S)-1-(3,5-bis-trifluoromethyl-phenyl)-ethyl]-methyl-amide (1S,2S)-1-methylamino-2-phenyl-3-aza-bicyclo[3.1.0]hexane-3-carboxylic acid [(S)-1-(3,5-bis-trifluoromethyl-phenyl)-ethyl]-methyl-amide (1S,2S)-1-Amino-2-phenyl-3-aza-bicyclo[3.1.0]hexane-3-carboxylic acid [(S)-1-(3,5-bis-trifluoromethyl-phenyl)-ethyl]-methyl-amide (2-Methoxy-5-trifluoromethoxy-benzyl)-((1S,2S)-2-phenyl-3-aza-bicyclo[3.1.0]hex-1-yl)-amine Based on a reading of the present description and claims, certain modifications to the compounds, compositions and methods described herein will be apparent to one of ordinary skill in the art. The claims appended hereto are intended to encompass these modifications.

What is claimed is:

1. A compound having the Formula I:

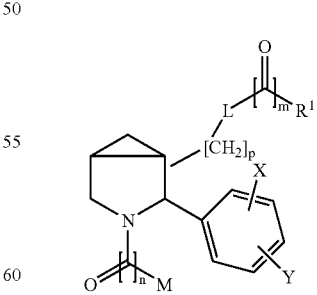

or a pharmaceutically acceptable salt or solvate thereof, wherein:

m is 0 or 1;
n is 0 or 1;
p is 0 or 1;

L is —O—, —C(=O)N(R⁵)— or —N(R⁵)—;

M is R², —NR²R³, or —NR²R⁴;

R¹ and R² are each independently H, —(C₁-C₆)alkyl, —(C₁-C₆)aryl,
—(C₁-C₆)heterocycloalkyl, —NR¹—(C₁-C₆)aryl or —(C₁-C₆)heteroaryl, wherein each of said —(C₁-C₆)alkyl, —(C₁-C₆)aryl, —(C₁-C₆)heterocycloalkyl, —NR¹—(C₁-C₆)aryl or —(C₁-C₆)heteroaryl is optionally substituted with 1-3 moieties independently selected from X', Y' and Z';

R³, R⁴ and R⁵ are each independently selected from H, CH₃, and —(C₁-C₆)alkyl; and X, Y, X', Y' and Z' are each independently selected from H, CH₃, —(C₁-C₆)alkyl, CF₃, OH, OCH₃, —O—(C₁-C₆)alkyl, halogen, and CN.

2. The compound of claim 1 wherein L is O, M is NR²R³, p is 0 or 1, m is 0 or 1; n is 1; R¹ and R² are each independently H, (C₁-C₆)alkyl, benzyl, —CH₂-heterocycloalkyl, or
—CH₂-heteroaryl, wherein each of said benzyl, —CH₂-heterocycloalkyl, or —CH₃-heteroaryl are optionally substituted with 1-3 moieties independently selected from X', Y' and Z'; R³ is H or (C₁-C₆)alkyl; and X, Y, X', Y' and Z' are each independently H, (C₁-C₆)alkyl, CF₃, OH, —O(C₁-C₆)alky), halogen, or CN.

3. The compound of claim 1 wherein L is O, M is R², p is 1, m is 0 or 1; n is 0 or 1; R¹ and R² are each independently H, CH₃, (C₁-C₆)alkyl, benzyl, —CH₂-heterocycloalkyl, or
—CH₂-heteroaryl, wherein each of said benzyl, —CH₂-heterocycloalkyl, or —CH₂-heteroaryl is optionally substituted with 1-3 moieties independently selected from X', Y' and Z'; and X, Y, X', Y' and Z' are each independently H, (C₁-C₆)alkyl, CF₃, OH, —O(C₁-C₆)alkyl, halogen, or CN.

4. The compound of claim 1 wherein L is NR⁵, M is R², p is 1, m is 0 or 1; n is 0 or 1; R¹ and R² are each independently H, (C₁-C₆)alkyl, benzyl, —CH₂-heterocycloalkyl, or
—CH₂-heteroaryl, wherein each of said benzyl, —CH₂-heterocycloalkyl, or
—CH₂-heteroaryl is optionally substituted with 1-3 moieties independently selected from X', Y' and Z'; R⁵ is H, CH₃, or (C₁-C₆)alkyl; and X, Y, X', Y' and Z' are each independently H, CH₃, (C₁-C₆)alkyl, CF₃, OH, —O(C₁-C₆)alkyl), halogen, or CN.

5. The compound of claim 1 wherein L is O, M is R², p is 0, m is 0 or 1; n is 0 or 1; R¹ and R² are each independently H, (C₁-C₆)alkyl, benzyl, —CH₃-heterocycloalkyl, or
—CH₂-heteroaryl, wherein each of said benzyl, —CH₂-heterocycloalkyl, or
—CH₂-heteroaryl is optionally substituted with 1-3 moieties independently selected from X', Y' and Z'; and X, Y, X', Y' and Z' are each independently H, CH₃, (C₁-C₆)alkyl, CF₃, OH, —O(C₁-C₆)alkyl, halogen, or CN.

6. The compound of claim 1 wherein L is —NR⁵, M is —NR²R⁴, p is 1, m is 0 or 1; n is 1; R¹ and R² are each independently H, CH₃, (C₁-C₆)alkyl, benzyl, —CH₃-heterocycloalkyl, or —CH₃-heteroaryl, wherein each of said benzyl, —CH₃-heterocycloalkyl, or —CH₃-heteroaryl is optionally substituted with 1-3 moieties independently selected from X', Y' and Z'; R⁴ and R⁵ are each independently H, CH₃, or (C₁-C₆)alkyl; and X, Y, X', Y' and Z' are each independently H, CH₃, (C₁-C₆)alkyl, CF₃, OH, —O(C₁-C₆)alkyl, halogen, or CN.

7. The compound of claim 1 wherein L is —NR⁵, M is R², p is 0, m is 0 or 1; n is 0 or 1; R¹ and R² are each independently H, CH₃, (C₁-C₆)alkyl, benzyl, —CH₂-heterocycloalkyl, or —CH₂-heteroaryl, wherein each of said benzyl, —CH₂-heterocycloalkyl, or —CH₂-heteroaryl is optionally substituted with 1-3 moieties independently selected from X', Y' and Z'; R⁵ is H, CH₃, or (C₁-C₆)alkyl; and X, Y, X', Y' and Z' are each independently H, CH₃, (C₁-C₆)alkyl, CF₃, OH, OCH₃, —O(C₁-C₆)alkyl, halogen, or CN.

8. The compound of claim 1 wherein L is O, M is NR²R³, p is 1, m is 0 or 1; n is 0 or 1; R¹ and R² are each independently H, CH₃, (C₁-C₆)alkyl, benzyl, —CH₂-heterocycloalkyl, or —CH₃-heteroaryl, wherein each of said benzyl, —CH₂-heterocycloalkyl, or —CH₂-heteroaryl is optionally substituted with 1-3 moieties independently selected from X', Y' and Z'; R³ is H, CH₃, or C₁₋₆alkyl; and X, Y, X', Y' and Z' are each independently H, (C₁-C₆)alkyl, CF₃, OH, OCH₃, —O(C₁-C₆)alkyl, halogen, or CN.

9. The compound according to claim 1 selected from the group consisting of:

(1aS,2R)-6-Methoxy-3-methyl-5-[((1R,2S,5S)-2-phenyl-3-aza-bicyclo[3.1.0]hex-1-ylamino)-methyl]-1,1a,3,7b-tetrahydro-3-aza-cyclopropa[a]naphthalen-2-one;

(5-tert-Butyl-2-methoxy-benzyl)-((1R,2S,5S)-2-phenyl-3-aza-bicyclo[3.1.0]hex-1-yl)-amine;

(6-Methoxy-1-methyl-1-trifluoromethyl-isochroman-7-ylmethyl)-((1R,2S,5S)-2-phenyl-3-aza-bicyclo[3.1.0]hex-1-yl)-amine;

(1R,2S,5S)-1-Methylamino-2-phenyl-3-aza-bicyclo[3.1.0]hexane-3-carboxylic acid [1-((R)-3,5-bis-trifluoromethyl-phenyl)-ethyl]-methyl-amide trifluoroacetic acid salt;

(1S,2S,5R)-1-Methylamino-2-phenyl-3-aza-bicyclo[3.1.0]hexane-3-carboxylic acid [1-((R)-3,5-bis-trifluoromethyl-phenyl)-ethyl]-methyl-amide;

(1S,2R,5R)-1-Methylamino-2-phenyl-3-aza-bicyclo[3.1.0]hexane-3-carboxylic acid [1-((S)-3,5-bis-trifluoromethyl-phenyl)-ethyl]-methyl-amide trifluro acetic acid;

(1R,2S,5S)-1-Methylamino-2-phenyl-3-aza-bicyclo[3.1.0]hexane-3-carboxylic acid [1-((S)-3,5-bis-trifluoromethyl-phenyl)-ethyl]-methyl-amide trifluro acetic acid salt;

(1R,2S,5S)-1-{[((1S,7bR)-6-Methoxy-3-methyl-2-oxo-1a,2,3,7b-tetrahydro-1H-3-aza-cyclopropa[a]naphthalen-5-ylmethyl)-amino]-methyl}-2-phenyl-3-aza-bicyclo[3.1.0]hexane-3-carboxylic acid tert-butyl ester;

(6-Methoxy-1-methyl-1-trifluoromethyl-isochroman-7-ylmethyl)-((1R,2S)-2-phenyl-3-aza-bicyclo[3.1.0]hex-1-ylmethyl)-amine;

(1S,2S)-1-(3,5-Bis-trifluoromethyl-benzyloxymethyl)-2-phenyl-3-aza-bicyclo[3.1.0]hexane;

5-[(1S,2S)-1-(3,5-Bis-trifluoromethyl-benzyloxymethyl)-2-phenyl-3-aza-bicyclo[3.1.0]hex-3-ylmethyl]-2,4-dihydro-[1,2,4]triazol-3-one;

{5-[(1S,2S)-1-(3,5-Bis-trifluoromethyl-benzyloxymethyl)-2-phenyl-3-aza-bicyclo[3.1.0]hex-3-ylmethyl]-1H-[1,2,3]triazol-4-ylmethyl}-dimethyl-amine;

(1S,2S)-1-(3,5-Bis-trifluoromethyl-benzyloxymethyl)-2-phenyl-3-aza-bicyclo[3.1.0]hexane-3-carboxylic acid [(S)-1-(3,5-bis-trifluoromethyl-phenyl)-ethyl]-methyl-amide;

(1R,2S)-1-(3,5-Bis-trifluoromethyl-benzyloxy)-2-phenyl-3-aza-bicyclo[3.1.0]hexane;

(1S,2S)-1-(3,5-Bis-trifluoromethyl-benzyloxy)-2-phenyl-3-aza-bicyclo[3.1.0]hexane;

5-[(1R,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one;

5-[(1S,2S)-1-(3,5-Bis-trifluoromethyl-benzyloxy)-2-phenyl-3-aza-bicyclo[3.1.0]hex-3-ylmethyl]-2,4-dihydro-[1,2,4]triazol-3-one;

{5-[(1R,2S)-1-(3,5-Bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

{5-[(1S,2S)-1-(3,5-Bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

(1S,2S)-1-Hydroxy-2-phenyl-3-aza-bicyclo[3.1.0]hexane-3-carboxylic acid [(S)-1-(3,5-bis-trifluoromethyl-phenyl)-ethyl]-methyl-amide;

(1R,2S)-1-Hydroxy-2-phenyl-3-aza-bicyclo[3.1.0]hexane-3-carboxylic acid [(S)-1-(3,5bis-trifluoromethyl-phenyl)-ethyl]-methyl-amide;

[(S)-1-(3,5-Bis-trifluoromethyl-phenyl)-ethyl]-methyl-carbamic acid (1R,2S)-2-phenyl-3-aza-bicyclo[3.1.0]hex-1-yl ester;

(1S,2S)-1-Hydroxymethyl-2-phenyl-3-aza-bicyclo[3.1.0]hexane-3-carboxylic acid [(R)-1-(3,5-bis-trifluoromethyl-phenyl)-ethyl]-methyl-amide;

(1R,2S)-1-methylaminomethyl-2-phenyl-3-aza-bicyclo[3.1.0]hexane-3-carboxylic acid[(R)-1-(3,5-bis-trifluoromethyl-phenyl)-ethyl]-methyl-amide;

(1R,2S)-1-Aminomethyl-2-phenyl-3-aza-bicyclo[3.1.0]hexane-3-carboxylic acid [(R)-1-(3,5-bis-trifluoromethyl-phenyl)-ethyl]-methyl-amide;

(1R,2R)-3-Benzyl-2-phenyl-3-aza-bicyclo[3.1.0]hexane-1-carboxylic acid [(S)-1-(3,5-bis-trifluoromethyl-phenyl)-ethyl]-methyl-amide;

(1S,2S)-2-Phenyl-3-aza-bicyclo[3.1.0]hexane-1-carboxylic acid [(S)-1-(3,5-bis-trifluoromethyl-phenyl)-ethyl]-methyl-amide;

(1S,2S)-1-methylamino-2-phenyl-3-aza-bicyclo[3.1.0]hexane-3-carboxylic acid [(S)-1-(3,5-bis-trifluoromethyl-phenyl)-ethyl]-methyl-amide;

(1S,2S)-1-Amino-2-phenyl-3-aza-bicyclo[3.1.0]hexane-3-carboxylic acid [(S)-1-(3,5-bis-trifluoromethyl-phenyl)-ethyl]-methyl-amide;

(2-Methoxy-5-trifluoromethoxy-benzyl)-((1S,2S)-2-phenyl-3-aza-bicyclo[3.1.0]hex-1-yl)-amine;

and pharmaceutically acceptable salts and solvates thereof.

10. A compound according to claim 1 selected from the group consisting of:

5-[1-(3,5-bis-trifluoromethyl-benzyloxy)-2-phenyl-3-aza-bicyclo[3.1.0]hex-3-ylmethyl]-2,4-dihydro-[1,2,4]triazol-3-one;

5-[1-(3,5-bis-trifluoromethyl-benzyloxy)-2-phenyl-3-aza-bicyclo[3.1.0]hex-3-ylmethyl]-2,4-dihydro-[1,2,4]triazol-3-one;

{5-[1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

{5-[1-(3,5-bis-trifluoromethyl-benzyloxy)-2-phenyl-3-aza-bicyclo[3.1.0]hex-3-ylmethyl]-3H-[1,2,3]triazol-4-ylmethyl}-dimethyl-amine;

1-(3,5-bis-trifluoromethyl-benzyloxy)-2-phenyl-3-aza-bicyclo[3.1.0]hexane;

1-(3,5-Bis-trifluoromethyl-benzyloxy)-2-phenyl-3-aza-bicyclo[3.1.0]hexane;

1-amino-2-phenyl-3-aza-bicyclo[3.1.0]hexane-3-carboxylicacid[1-(3,5-bis-trifluoromethyl-phenyl)-ethyl]-methyl-amide;

1-aminomethyl-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

1-methylamino-2-phenyl-3-aza-bicyclo[3.1.0]hexane-3-carboxylicacid[1-(3,5-bis-trifluoromethyl-phenyl)-ethyl]-methyl-amide;

2-phenyl-3-aza-bicyclo[3.1.0]hexane-1-carboxylicacid [1-(3,5-bis-trifluoromethyl-phenyl)-ethyl]-methyl-amide;

3-benzyl-2-phenyl-3-aza-bicyclo[3.1.0]hexane-1-carboxylicacid[1-(3,5-bis-trifluoromethyl-phenyl)-ethyl]-methyl-amide;

and pharmaceutically acceptable salts and solvates thereof.

11. A pharmaceutical composition for treating a condition or disorder associated with the activity of NK-1 receptors in a mammal, comprising an amount of a compound according to claim 1, or a pharmaceutically acceptable salt and a pharmaceutically acceptable carrier, wherein the amount of said compound is effective in treating chemotheraphy induced emesis and depression.

* * * * *